United States Patent
Wilson et al.

(10) Patent No.: US 9,827,005 B2
(45) Date of Patent: Nov. 28, 2017

(54) SYSTEMS AND METHODS FOR ENDOLUMINAL VALVE CREATION

(71) Applicant: The Board of Trustees of the Leland Stanford Junior University, Palo Alto, CA (US)

(72) Inventors: Fletcher T. Wilson, San Francisco, CA (US); Rhunjay James Yu, Mountain View, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 0 days.

(21) Appl. No.: 15/235,127

(22) Filed: Aug. 12, 2016

(65) Prior Publication Data
US 2017/0035450 A1 Feb. 9, 2017

Related U.S. Application Data

(63) Continuation of application No. 13/450,432, filed on Apr. 18, 2012.
(Continued)

(51) Int. Cl.
*A61B 17/22* (2006.01)
*A61B 17/3203* (2006.01)
(Continued)

(52) U.S. Cl.
CPC ...... *A61B 17/3203* (2013.01); *A61B 17/3209* (2013.01); *A61B 17/320016* (2013.01);
(Continued)

(58) Field of Classification Search
CPC ...... A61B 17/3478; A61B 2017/22069; A61B 17/3203; A61B 17/32037; A61B 2017/320048
See application file for complete search history.

(56) References Cited

U.S. PATENT DOCUMENTS 3,704,711 A 12/1972 Park
4,932,962 A 6/1990 Yoon et al.
(Continued)

FOREIGN PATENT DOCUMENTS

CA 1281381 C 3/1991
CN 1907243 A 2/2007
(Continued)

OTHER PUBLICATIONS

Final Office Action dated Apr. 4, 2013 for U.S. Appl. No. 13/035,752.
(Continued)

*Primary Examiner* — Gregory Anderson
*Assistant Examiner* — Sarah Simpson
(74) *Attorney, Agent, or Firm* — Vista IP Law Group, LLP

(57) ABSTRACT

The present application pertains generally to medical systems and methods for creation of an autologous tissue valves within a mammalian body. In some embodiments, a system for creating an endoluminal valve from a blood vessel wall is provided. The system includes a tubular assembly having a longitudinal axis, a proximal end, a distal portion with a distal end, and a first lumen extending from the proximal end to a distal port located proximate the distal portion. The distal portion can have a supporting surface that extends in a longitudinal direction and is offset from a surface of the tubular assembly proximal the distal port. The system can further include a tissue dissection probe disposed within the first lumen.

19 Claims, 43 Drawing Sheets

Related U.S. Application Data

(60) Provisional application No. 61/596,179, filed on Feb. 7, 2012, provisional application No. 61/483,173, filed on May 6, 2011, provisional application No. 61/477,307, filed on Apr. 20, 2011.

(51) Int. Cl.
*A61B 17/32* (2006.01)
*A61B 17/3209* (2006.01)
*A61B 17/3207* (2006.01)
*A61B 17/04* (2006.01)
*A61B 17/08* (2006.01)
*A61F 2/24* (2006.01)
*A61B 17/295* (2006.01)
*A61B 17/34* (2006.01)
*A61B 17/30* (2006.01)

(52) U.S. Cl.
CPC .. *A61B 17/320783* (2013.01); *A61B 17/0469* (2013.01); *A61B 17/08* (2013.01); *A61B 17/295* (2013.01); *A61B 17/3478* (2013.01); *A61B 2017/081* (2013.01); *A61B 2017/22069* (2013.01); *A61B 2017/306* (2013.01); *A61B 2017/320044* (2013.01); *A61B 2017/320048* (2013.01); *A61B 2017/320056* (2013.01); *A61F 2/2475* (2013.01)

(56) References Cited

U.S. PATENT DOCUMENTS

| | | |
|---|---|---|
| 5,372,601 A | 12/1994 | Lary |
| 5,443,443 A | 8/1995 | Shiber |
| 5,464,395 A | 11/1995 | Faxon et al. |
| 5,601,588 A | 2/1997 | Tonomura et al. |
| 5,695,507 A | 12/1997 | Auth et al. |
| 5,738,901 A | 4/1998 | Wang et al. |
| 5,810,847 A | 9/1998 | Laufer et al. |
| 5,836,945 A | 11/1998 | Perkins |
| 5,989,276 A | 11/1999 | Houser |
| 6,190,353 B1 | 2/2001 | Makower |
| 6,475,226 B1 | 11/2002 | Belef et al. |
| 6,506,178 B1 | 1/2003 | Schubart et al. |
| 6,514,217 B1 | 2/2003 | Selmon et al. |
| 6,685,648 B2 | 2/2004 | Flaherty et al. |
| 6,692,466 B1* | 2/2004 | Chow ............... A61M 25/0084 604/164.01 |
| 6,702,744 B2 | 3/2004 | Mandrusov |
| 6,758,836 B2 | 7/2004 | Zawacki |
| 6,902,576 B2 | 6/2005 | Drasler et al. |
| 7,008,411 B1 | 3/2006 | Mandrusov et al. |
| 7,056,325 B1 | 6/2006 | Makower et al. |
| 7,150,738 B2 | 12/2006 | Ray |
| 7,179,249 B2 | 2/2007 | Steward et al. |
| 7,273,469 B1 | 9/2007 | Chan et al. |
| 7,357,795 B2 | 4/2008 | Kaji et al. |
| 7,517,352 B2 | 4/2009 | Evans |
| 7,775,968 B2 | 8/2010 | Mathis |
| 7,780,592 B2 | 8/2010 | Tronnes |
| 7,918,870 B2 | 4/2011 | Kugler et al. |
| 7,927,305 B2 | 4/2011 | Yribarren et al. |
| 7,938,819 B2 | 5/2011 | Kugler et al. |
| 7,955,346 B2 | 6/2011 | Mauch et al. |
| 8,025,655 B2 | 9/2011 | Kugler et al. |
| 8,083,727 B2 | 12/2011 | Kugler et al. |
| 8,100,860 B2 | 1/2012 | Von Oepen et al. |
| 8,114,123 B2 | 2/2012 | Brenzel et al. |
| 8,267,947 B2 | 9/2012 | Pantages et al. |
| 8,323,261 B2 | 12/2012 | Kugler et al. |
| 8,460,316 B2 | 6/2013 | Wilson et al. |
| 9,545,289 B2* | 1/2017 | Wilson ............ A61B 17/320016 |
| 2002/0029052 A1 | 3/2002 | Evans et al. |
| 2002/0072706 A1 | 6/2002 | Hiblar et al. |
| 2002/0091362 A1 | 7/2002 | Maginot |
| 2002/0103459 A1 | 8/2002 | Sparks et al. |
| 2004/0167558 A1 | 8/2004 | Igo et al. |
| 2004/0215339 A1 | 10/2004 | Drasler et al. |
| 2005/0075665 A1 | 4/2005 | Brenzel et al. |
| 2005/0165466 A1 | 7/2005 | Morris et al. |
| 2005/0273159 A1 | 12/2005 | Opie |
| 2006/0136045 A1 | 6/2006 | Flagle et al. |
| 2006/0235449 A1 | 10/2006 | Schubart et al. |
| 2006/0271090 A1 | 11/2006 | Shaked et al. |
| 2007/0093780 A1* | 4/2007 | Kugler ................ A61B 17/221 604/510 |
| 2007/0093781 A1 | 4/2007 | Kugler et al. |
| 2008/0243065 A1 | 10/2008 | Rottenberg et al. |
| 2009/0005793 A1 | 1/2009 | Pantages et al. |
| 2009/0112059 A1 | 4/2009 | Nobis |
| 2009/0182192 A1 | 7/2009 | Shiono et al. |
| 2009/0209910 A1 | 8/2009 | Kugler et al. |
| 2009/0254051 A1 | 10/2009 | Von Oepen et al. |
| 2010/0152682 A1 | 6/2010 | Mauch et al. |
| 2010/0152843 A1 | 6/2010 | Mauch et al. |
| 2010/0256599 A1 | 10/2010 | Kassab et al. |
| 2011/0264127 A1 | 10/2011 | Mauch et al. |
| 2012/0289987 A1 | 11/2012 | Wilson et al. |

FOREIGN PATENT DOCUMENTS

| | | |
|---|---|---|
| CN | 1957861 A | 5/2007 |
| JP | 2003033357 | 2/2003 |
| JP | 20020072706 | 9/2003 |
| JP | 2009165822 | 7/2009 |
| JP | 2009183516 | 8/2009 |
| RU | 2108751 C1 | 4/1998 |
| RU | 2160057 | 10/2000 |
| WO | WO 9900059 A1 | 1/1999 |
| WO | WO 2010074853 | 7/2010 |
| WO | WO 2011106735 A1 | 9/2011 |

OTHER PUBLICATIONS

Final Office Action dated Sep. 19, 2014 for U.S. Appl. No. 13/035,752.
Final Office Action dated Sep. 15, 2015 for U.S. Appl. No. 13/035,752.
Non-Final Office Action dated May 19, 2014 for U.S. Appl. No. 13/035,752.
Non-Final Office Action dated Oct. 16, 2012 for U.S. Appl. No. 13/035,752.
Lugli, M., et al., Neovalve construction in the deep venous incompetence, Twentieth Annual Meeting of the American Venous Forum, Charleston, SC, Feb. 20-23, 2008.
Non-Final Office Action dated Apr. 8, 2015 for U.S. Appl. No. 13/035,752.
Non-Final Office Action dated Feb. 19, 2014 for U.S. Appl. No. 13/450,432.
Non-Final Office Action dated Sep. 9, 2014 for U.S. Appl. No. 13/450,432.
Final Office Action dated Jun. 24, 2015 for U.S. Appl. No. 13/450,432.
Non-Final Office Action dated Oct. 24, 2014 for U.S. Appl. No. 13/926,886.
International Preliminary Report dated Sep. 7, 2012 for PCT Appln. No. PCT/US11/26370.
International Search Report dated Jul. 7, 2011 for PCT Application No. PCT/US2011/026370.
International Search Report & Written Opinion dated Aug. 10, 2012 for PCT Application No. PCT/US12/34138.
Non-Final Office Action dated Sep. 14, 2012 for U.S. Appl. No. 13/035,818.
Notice of Allowance dated Feb. 22, 2013 for U.S. Appl. No. 13/035,818.
Extended European Search Report dated Sep. 26, 2014 for Application No. 12774651.9.
International Search Report and Written Opinion dated Apr. 25, 2013 for PCT Appln. No. PCT/US2013/025196.

(56) References Cited

OTHER PUBLICATIONS

Foreign Office Action dated Oct. 22, 2014 for Japanese Application No. 2012-555202.
Extended Search Report dated Mar. 10, 2015 for EP Appln. No. 11748204.2.
Non-Final Office Action dated Sep. 2, 2015 for U.S. Appl. No. 13/926,886.
Final Office Action dated May 6, 2015 for U.S. Appl. No. 13/926,886.
Foreign Office Action dated Jun. 19, 2015 for Australian Appln. No. 2011220402.
Foreign Office Action dated Aug. 25, 2015 for Application No. 12774651.9.
Foreign Office Action dated Oct. 1, 2015 for Japanese Application No. 2012-555202.
Foreign Office Action dated Aug. 28, 2015 for Chinese Appln. No. 201280030278.2.
Foreign Office Action dated Jun. 14, 2016 for Chinese Appln. No. 201280030278.2.
Examiner's Answer to Appeal Brief dated Oct. 27, 2016 for U.S. Appl. No. 13/450,432.
Non-Final Office Action dated Sep. 14, 2016 for U.S. Appl. No. 13/035,752.
Final Office Action dated Aug. 16, 2016 for U.S. Appl. No. 13/926,886.
Notice of Allowance dated Nov. 30, 2016 for U.S. Appl. No. 13/035,752.
Foreign Office Action dated Nov. 18, 2016 for Canadian Appln. No. 2787496.
Non-Final Office Action dated Feb. 2, 2017 for U.S. Appl. No. 15/235,136.
Notice of Allowance dated Apr. 13, 2017 for U.S. Appl. No. 13/926,886.
Notice of Refusal dated Jan. 10, 2017 for Japanese Appln. No. 2016-017546.
Notice of Allowance dated Sep. 13, 2017 for U.S. Appl. No. 13/926,886.
Final Office Action dated Aug. 25, 2017 for U.S. Appl. No. 15/235,136.

* cited by examiner

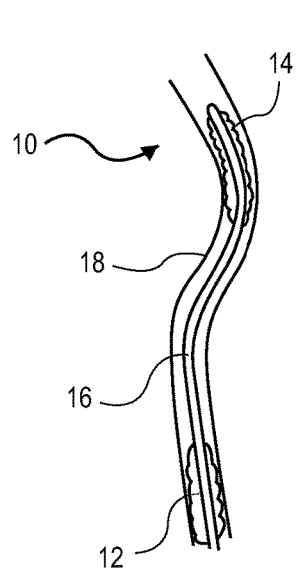
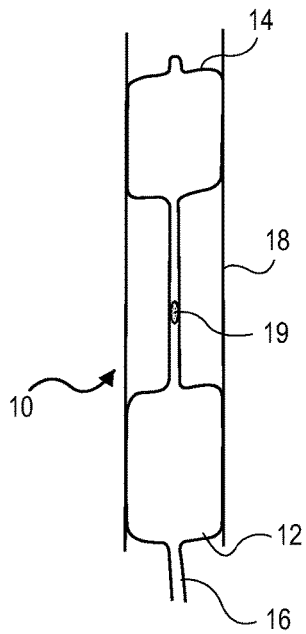
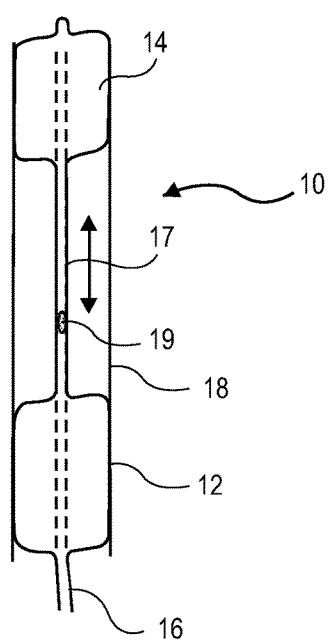
FIG. 1A  FIG. 1B  FIG. 1C
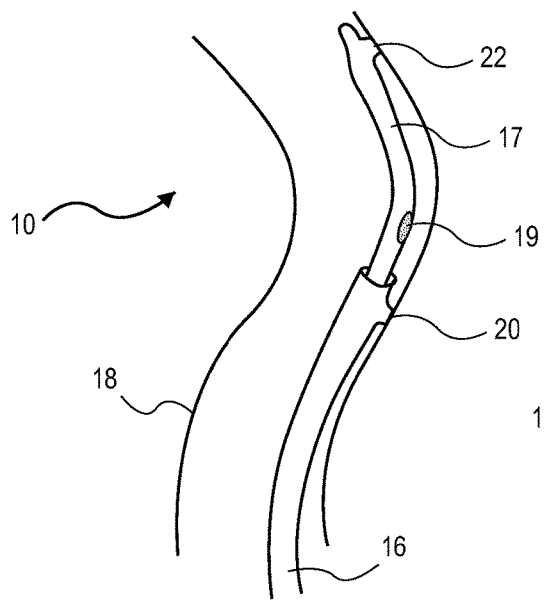
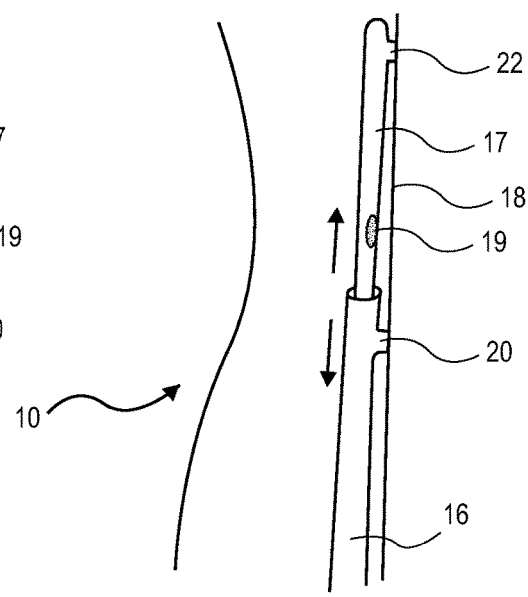
FIG. 2A  FIG. 2B

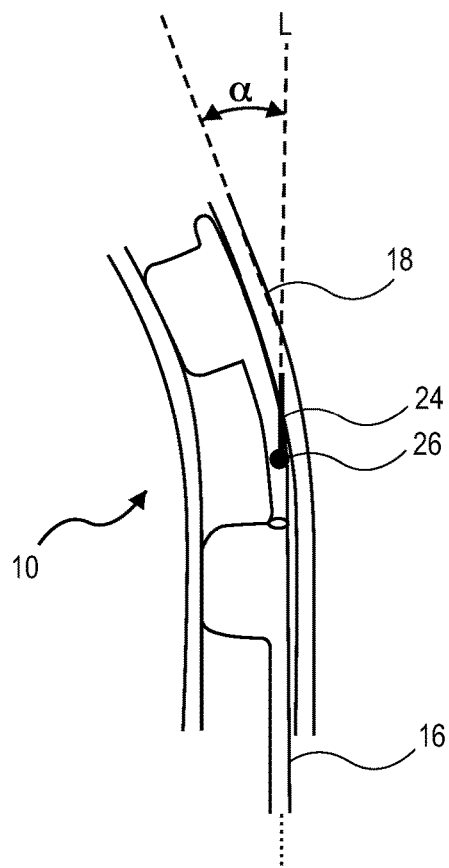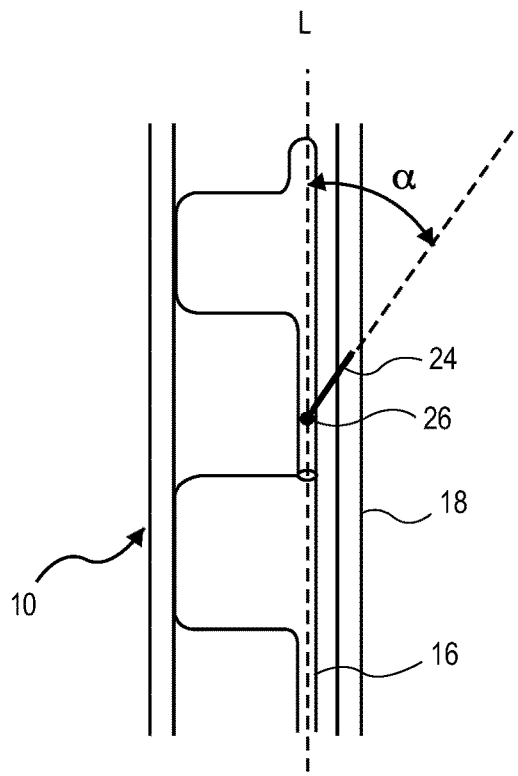
FIG. 3A  FIG. 3B
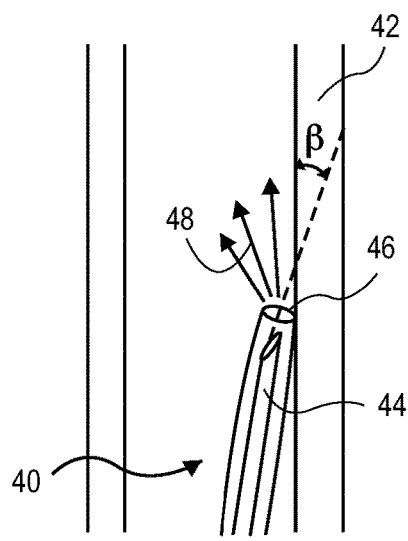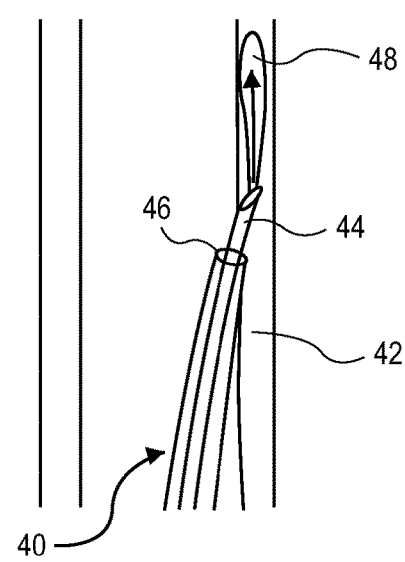
FIG. 4A  FIG. 4B

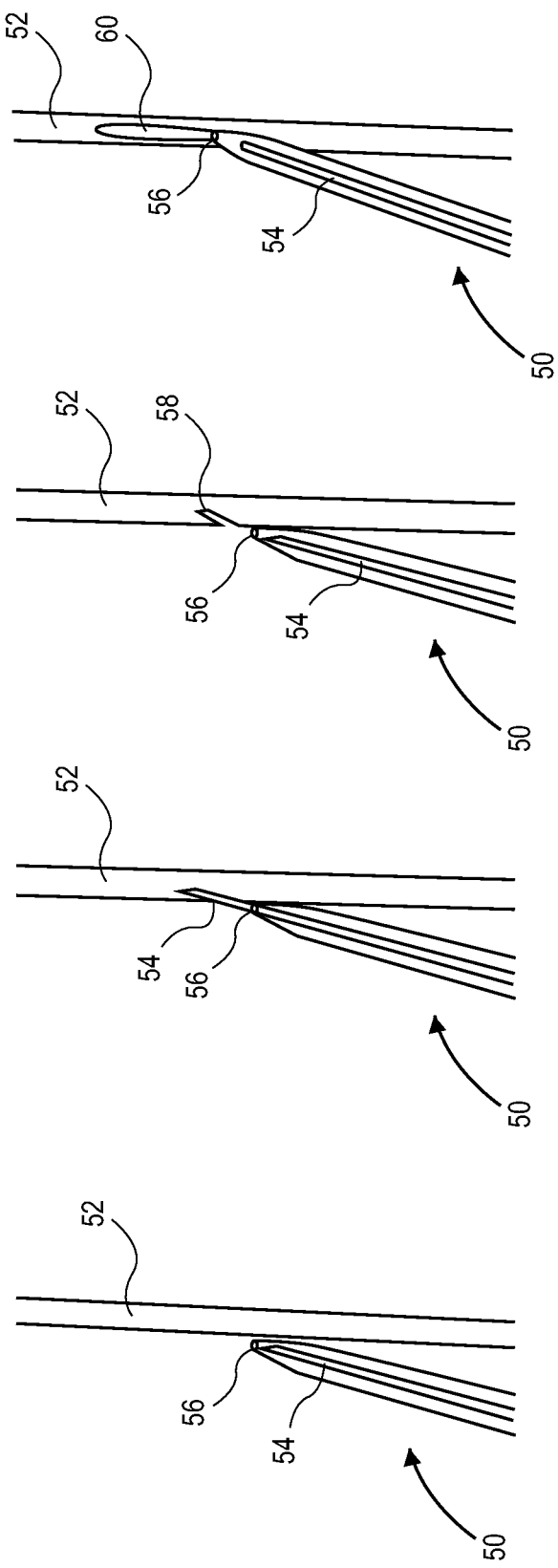

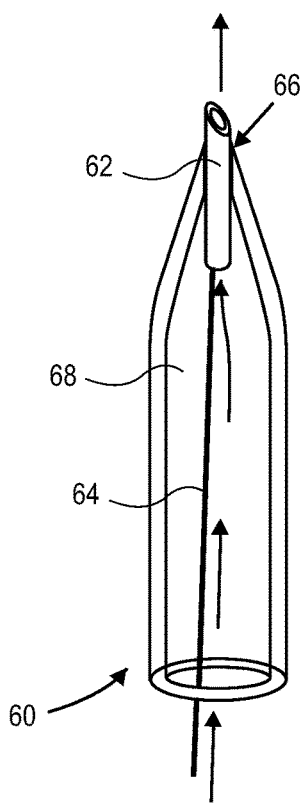
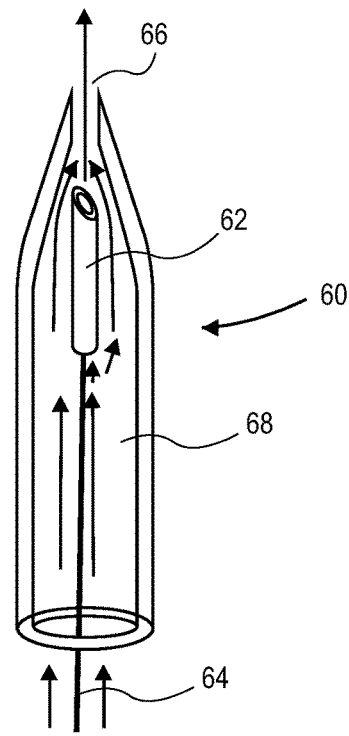
FIG. 6A    FIG. 6B
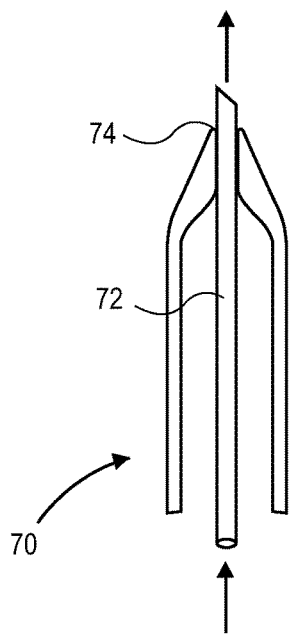
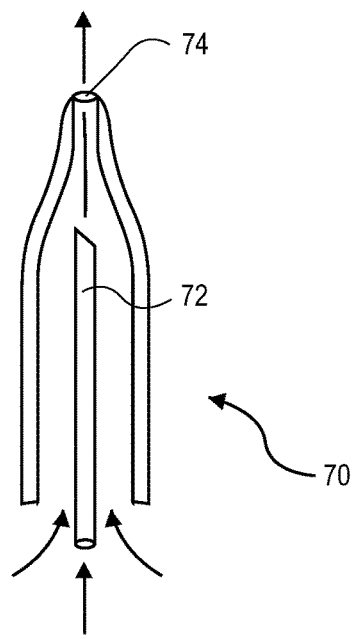
FIG. 7A    FIG. 7B

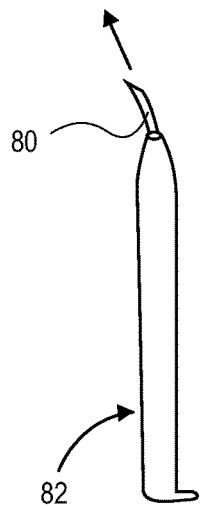 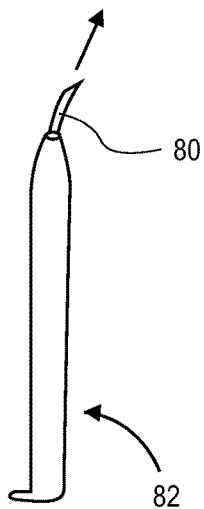 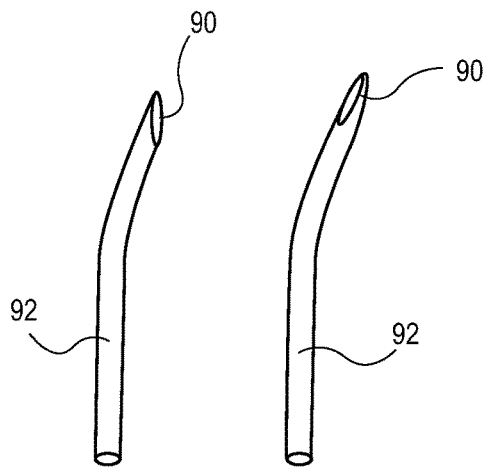
FIG. 8A  FIG. 8B  FIG. 9A  FIG. 9B
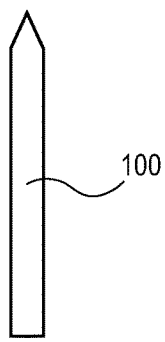 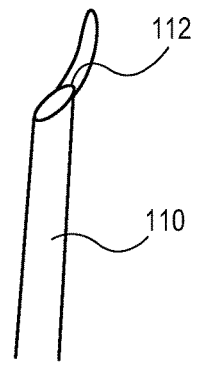
FIG. 10  FIG. 11

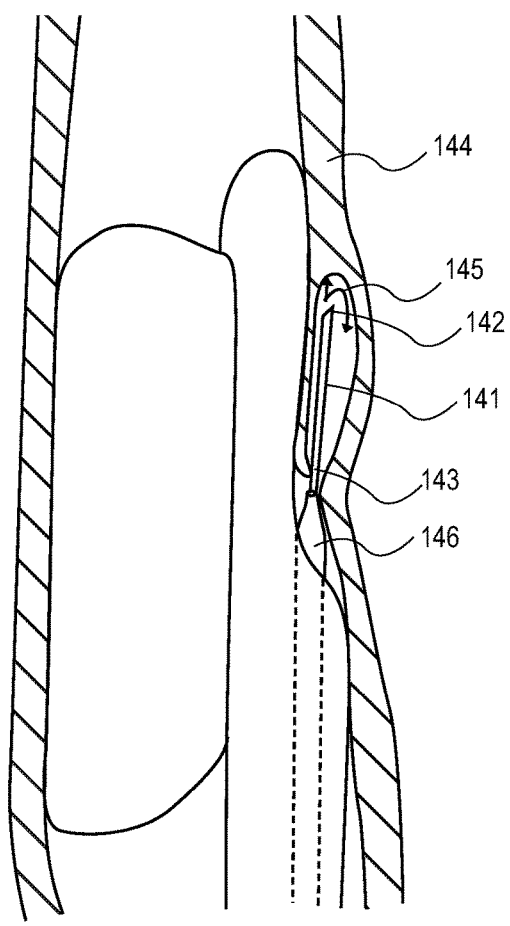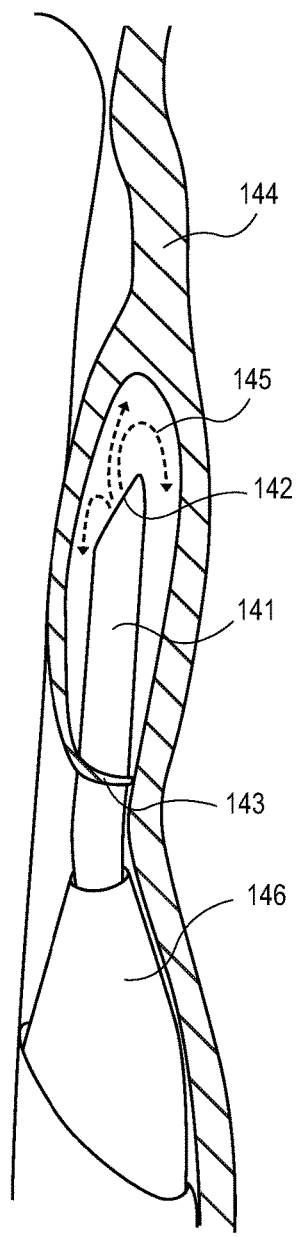
FIG. 14B     FIG. 14C

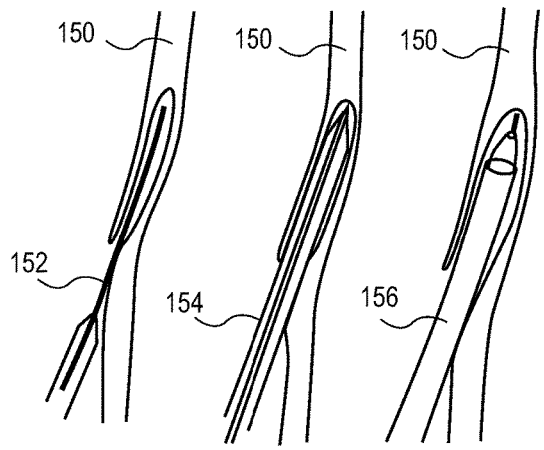
FIG. 15
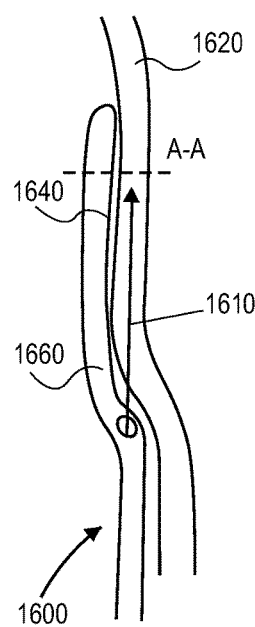 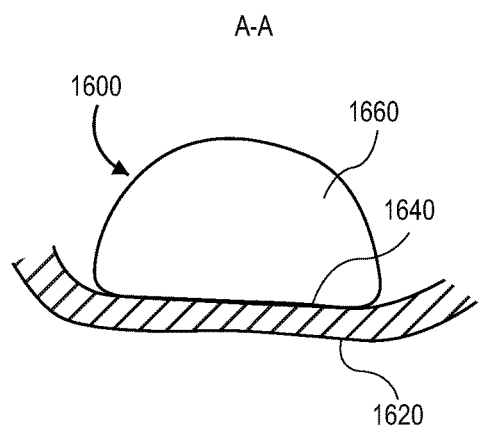 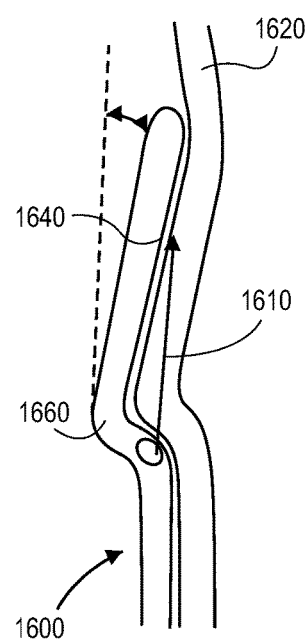
FIG. 16A  FIG. 16B  FIG. 16C

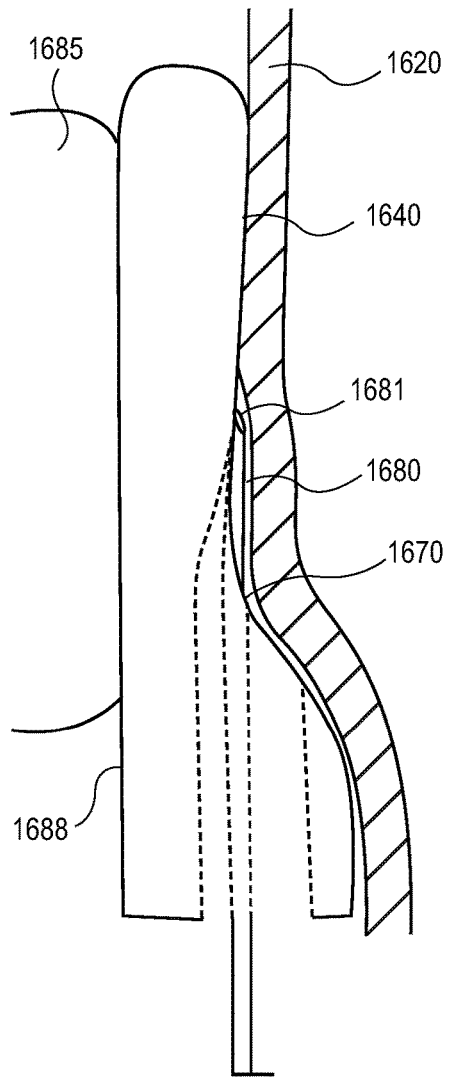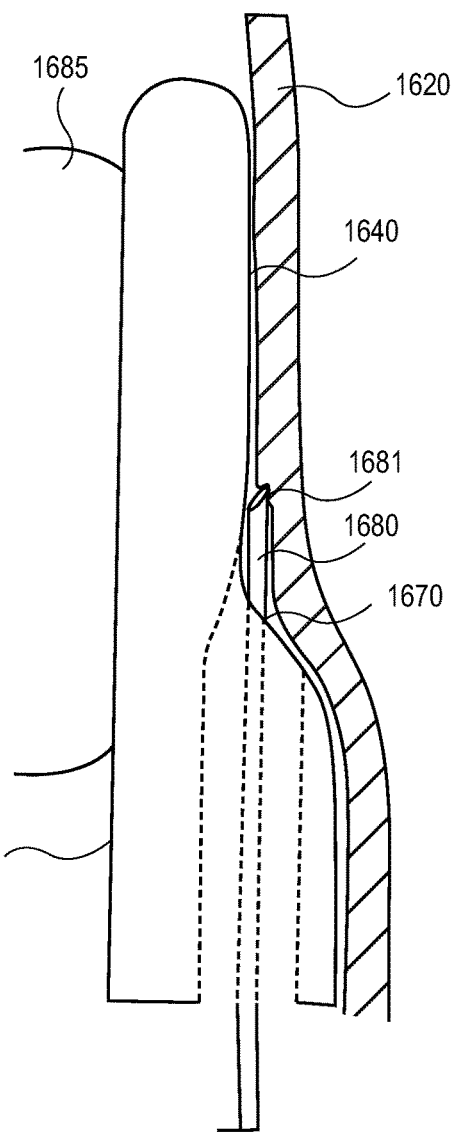
FIG. 16H　　　　FIG. 16I

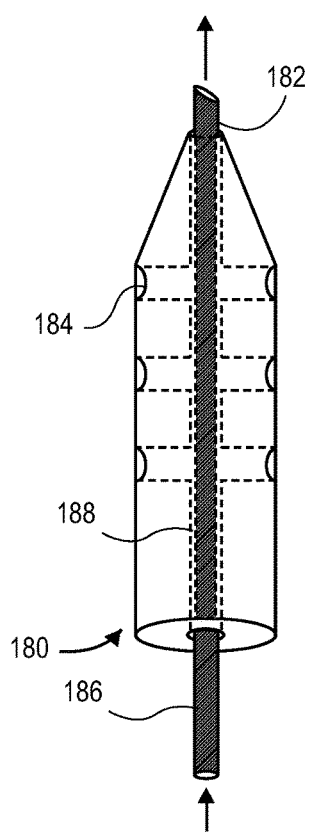 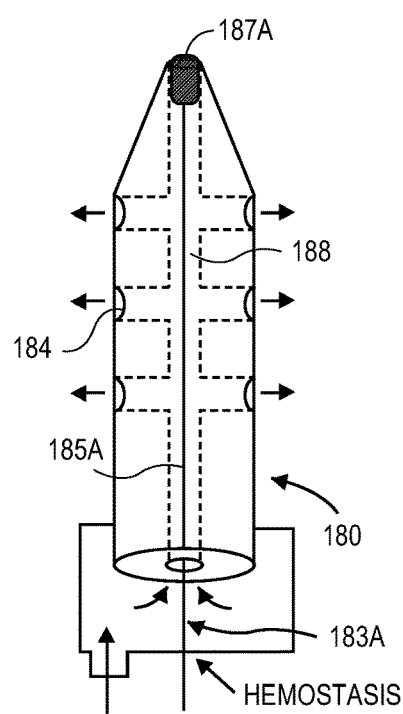 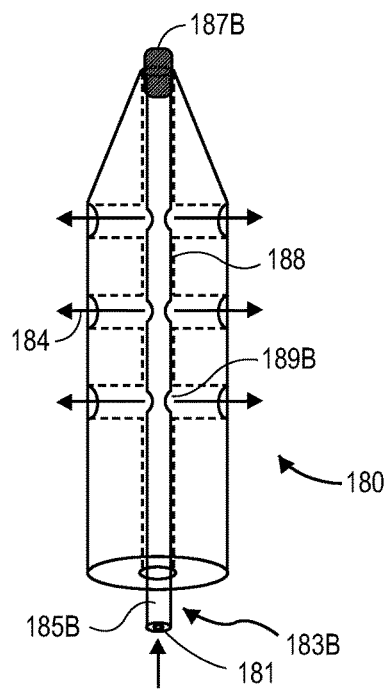
FIG. 18A   FIG. 18B   FIG. 18C
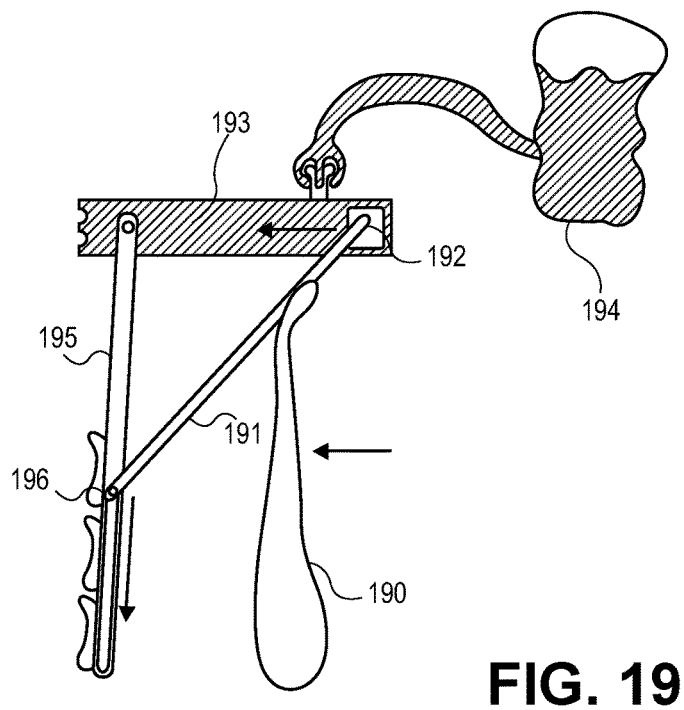
FIG. 19

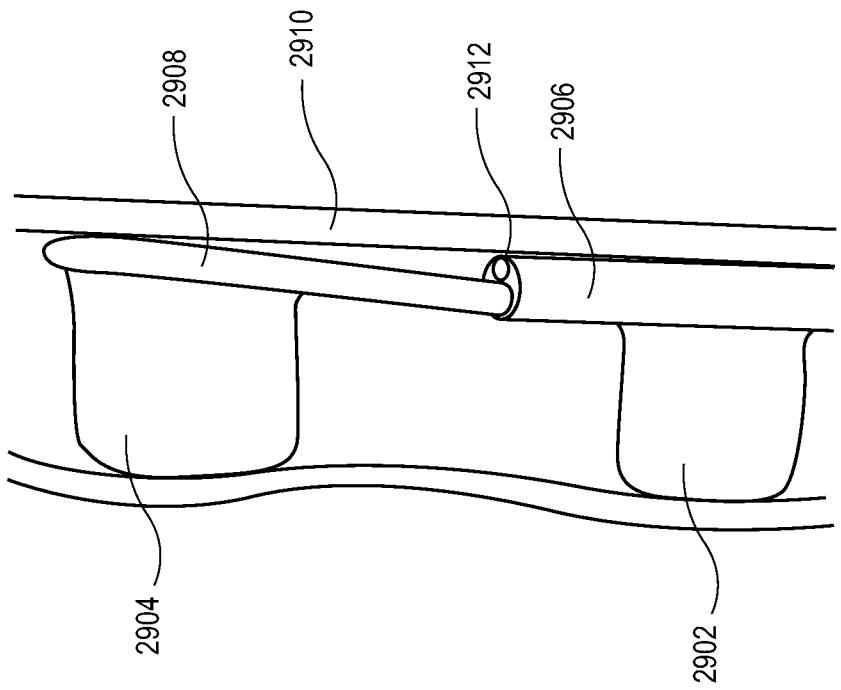
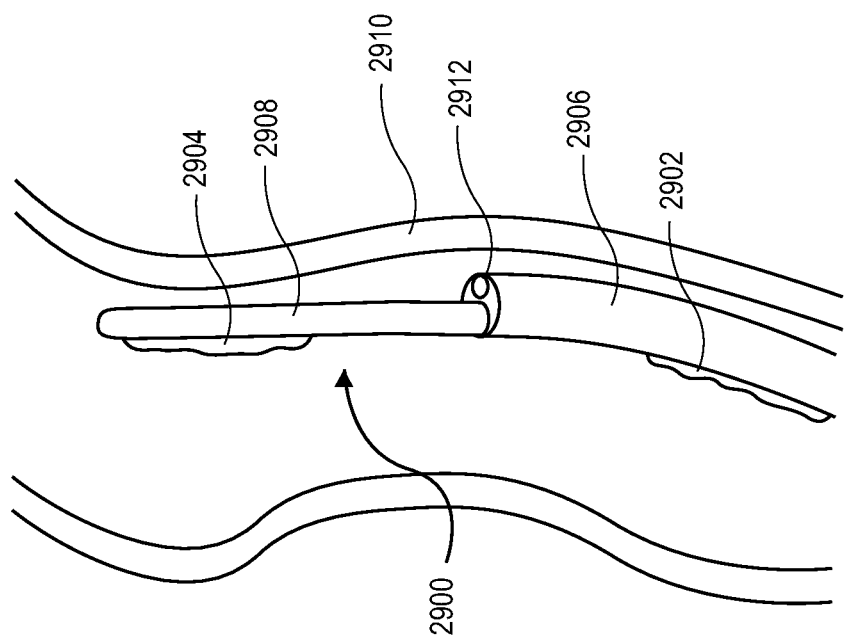

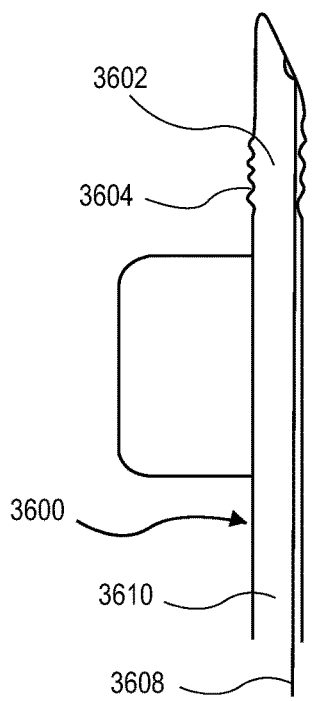 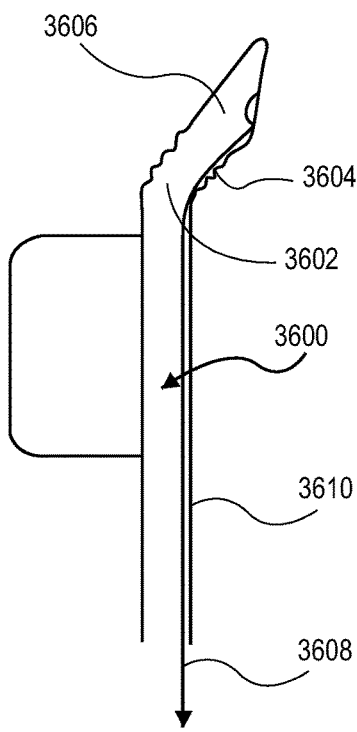
FIG. 36A         FIG. 36B
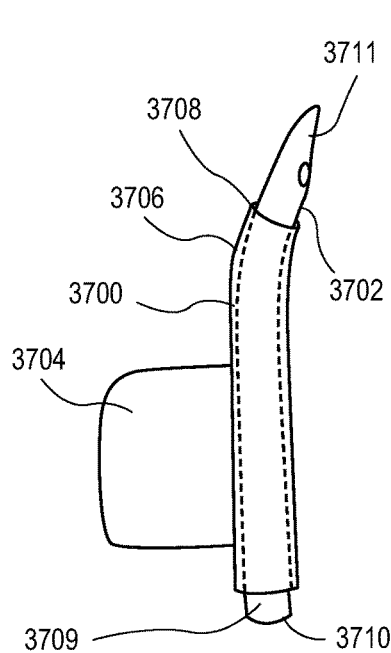 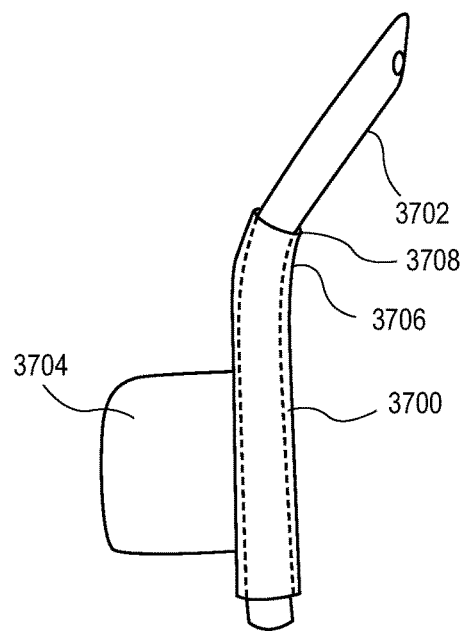
FIG. 37A         FIG. 37B

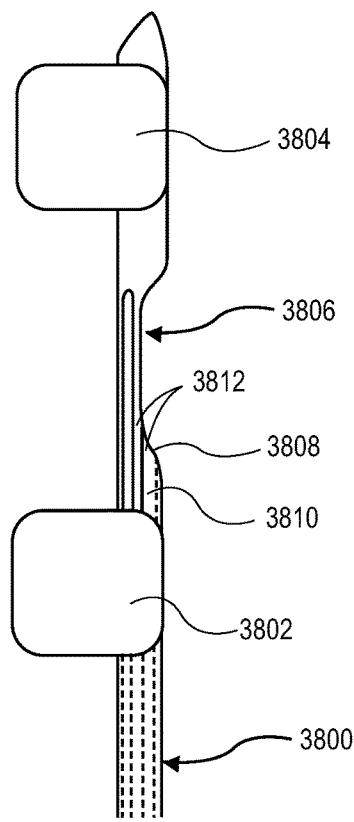
FIG. 38A
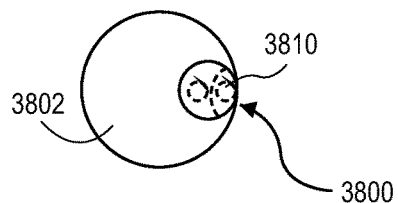
FIG. 38B
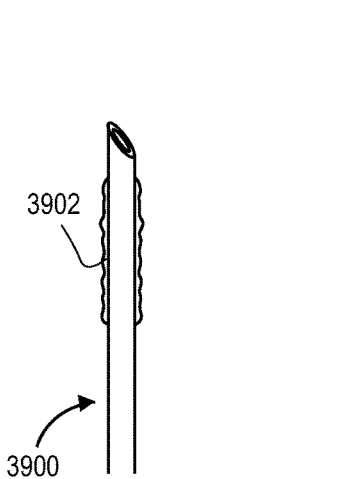
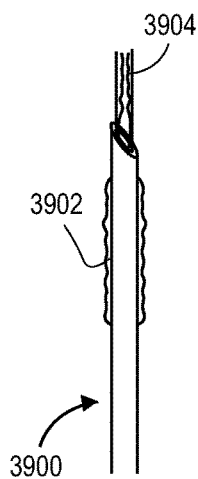
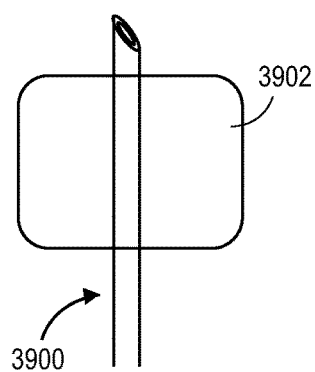
FIG. 39A   FIG. 39B   FIG. 39C

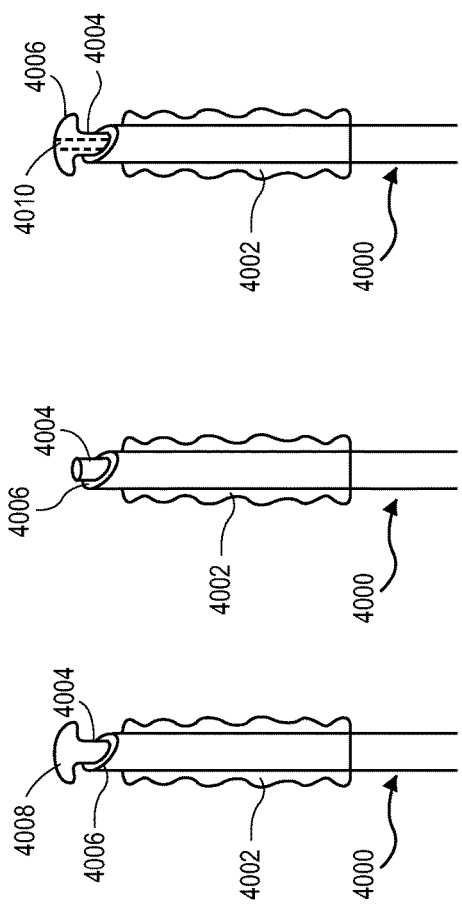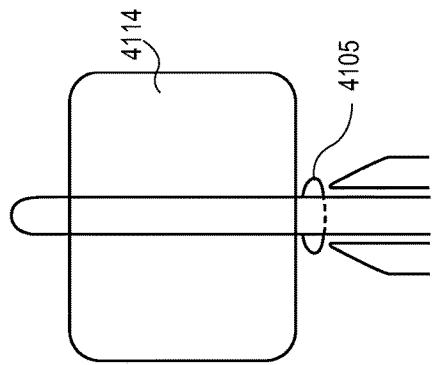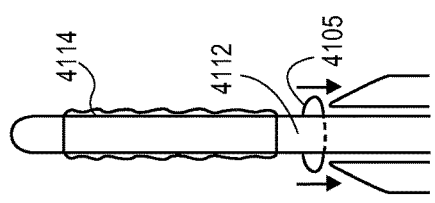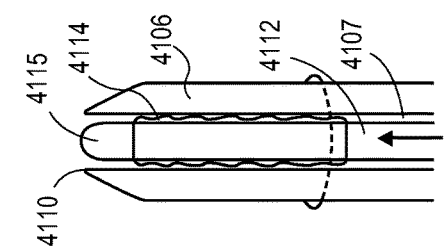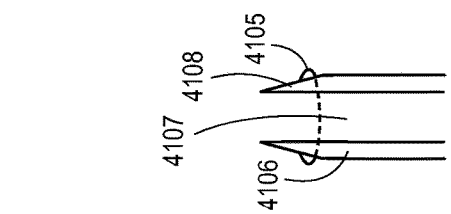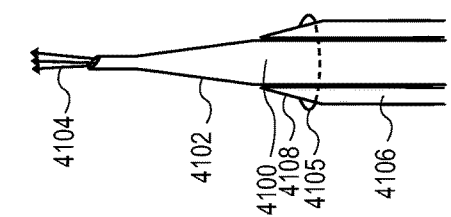

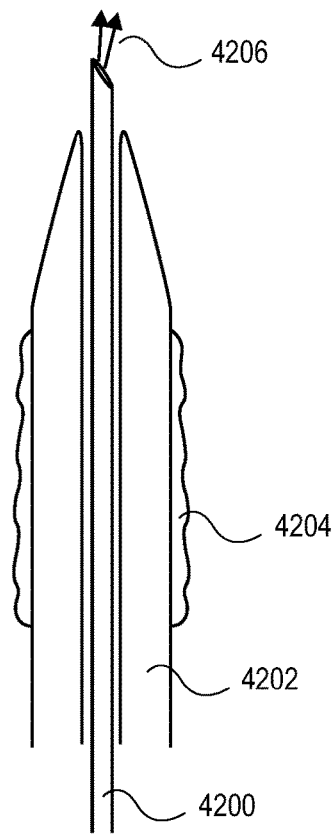
FIG. 42
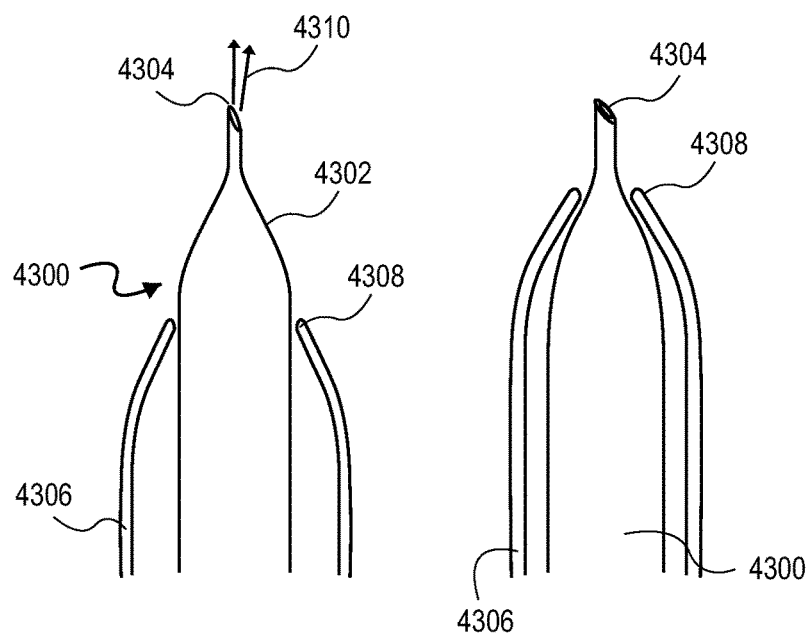
FIG. 43A   FIG. 43B   FIG. 43C

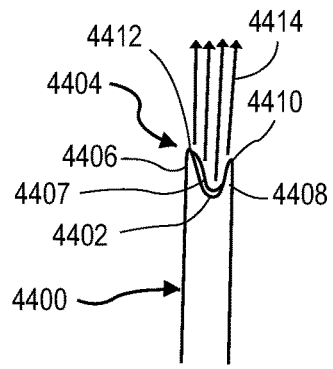 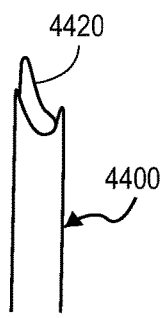 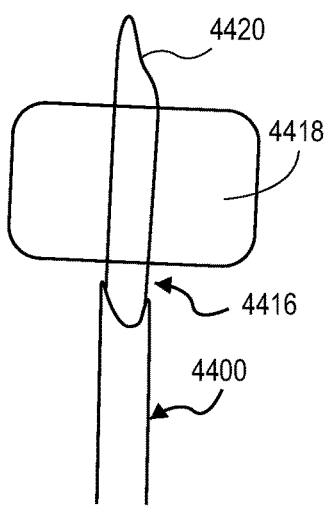
FIG. 44A  FIG. 44B  FIG. 44C
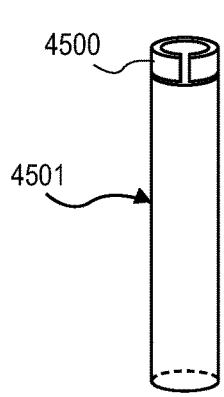 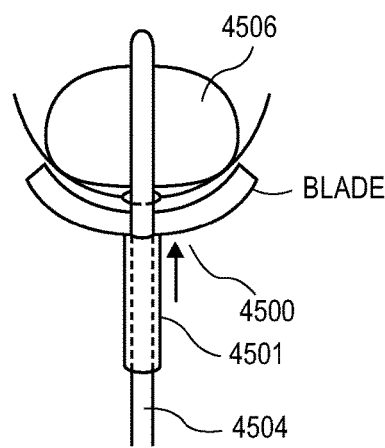 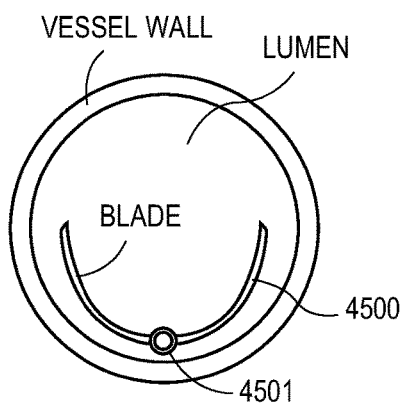
FIG. 45A  FIG. 45B  FIG. 45C

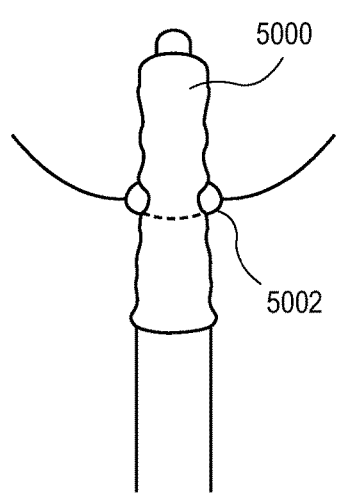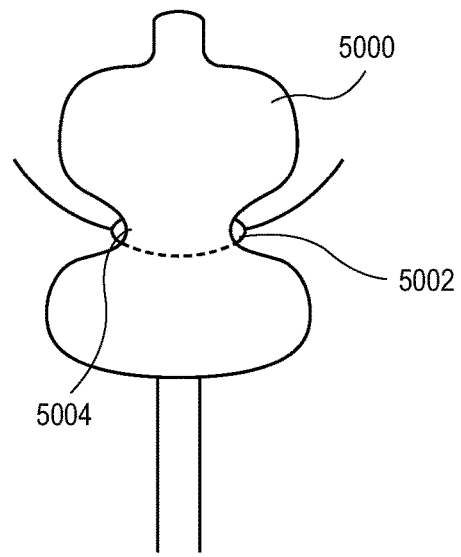
FIG. 50A  FIG. 50B
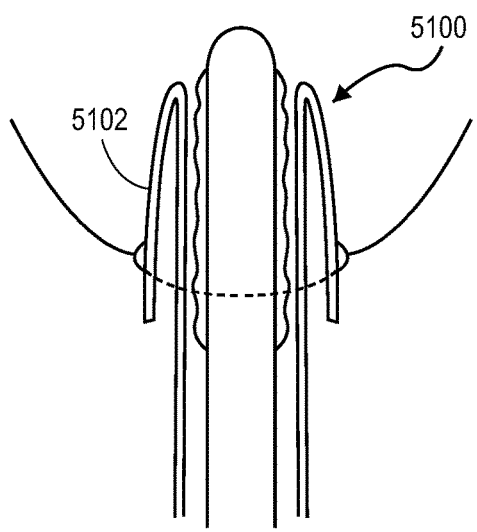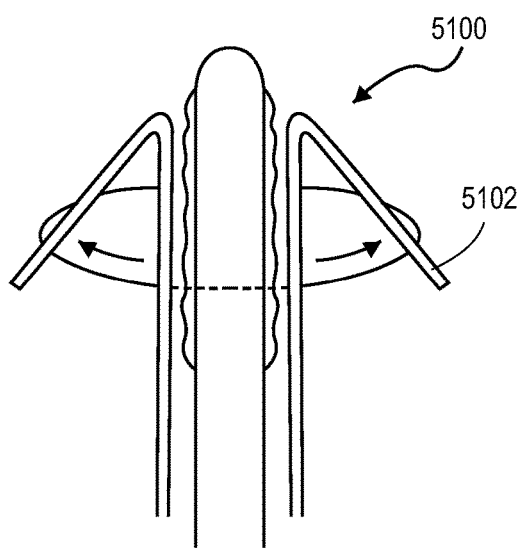
FIG. 51A  FIG. 51B

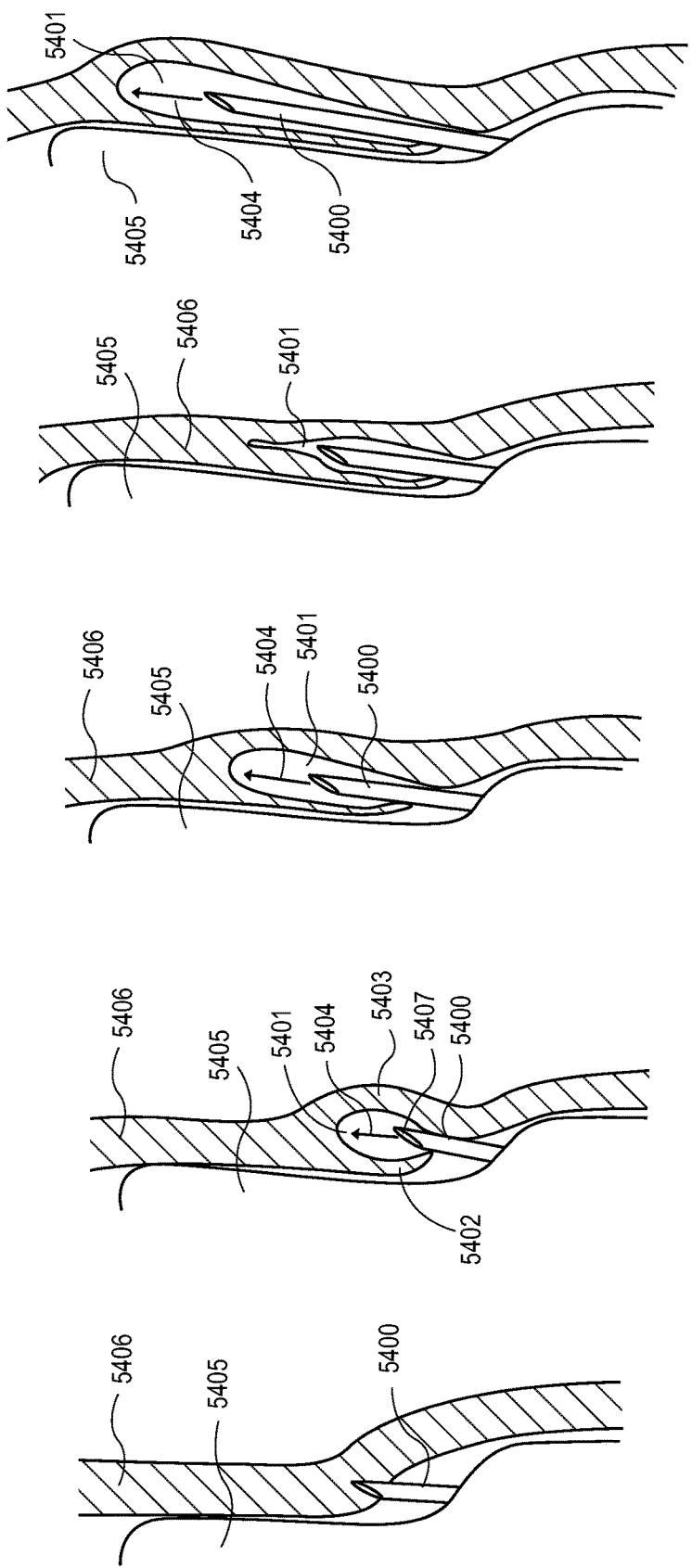

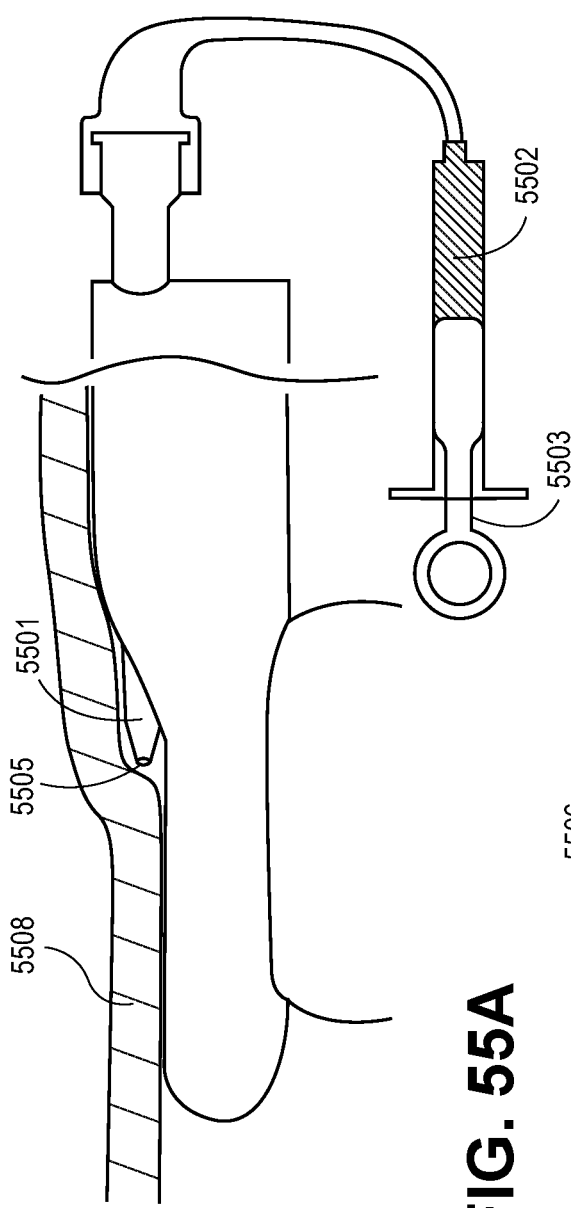
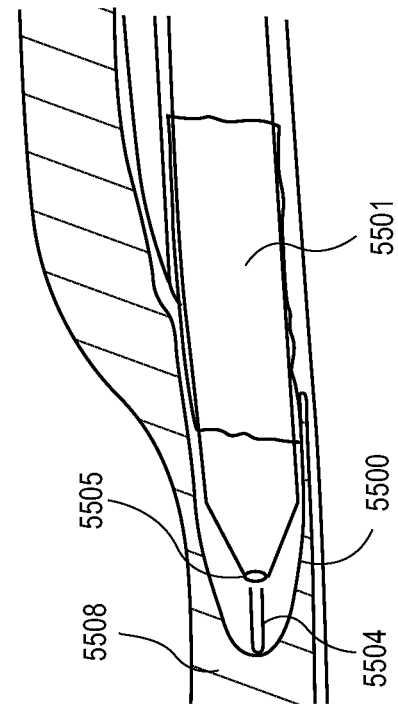
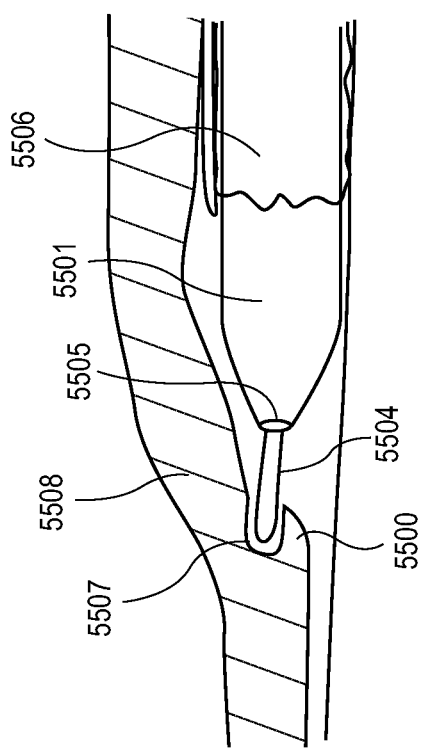
FIG. 55A
FIG. 55B
FIG. 55C

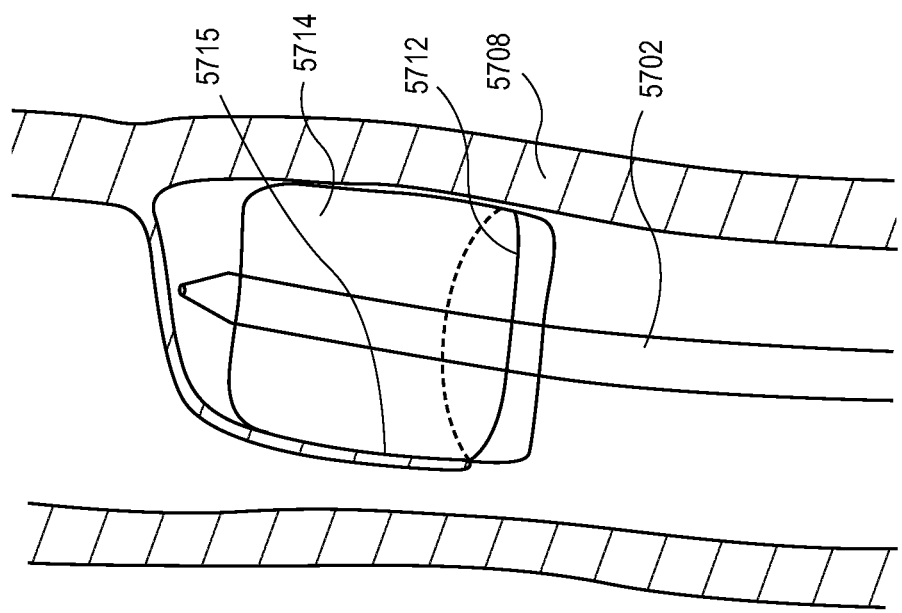
FIG. 57D
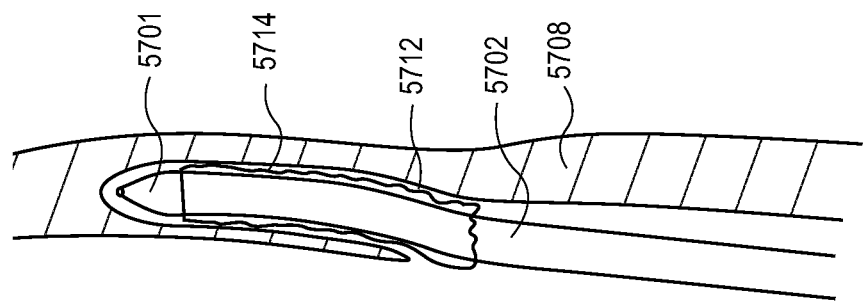
FIG. 57C
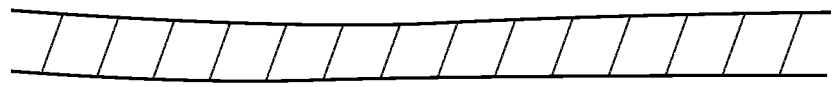

SYSTEMS AND METHODS FOR ENDOLUMINAL VALVE CREATION

CROSS-REFERENCE TO RELATED APPLICATION(S)

This application is a continuation of U.S. patent application Ser. No. 13/450,432, filed Apr. 18, 2012, which claims the benefit of U.S. Provisional Application No. 61/477,307, filed Apr. 20, 2011, U.S. Provisional Application No. 61/483,173, filed May 6, 2011, and U.S. Provisional Application No. 61/596,179, filed Feb. 7, 2012, all of which are hereby incorporated by reference in their entireties.

All publications and patent applications mentioned in this specification are herein incorporated by reference to the same extent as if each individual publication or patent application was specifically and individually indicated to be incorporated by reference.

TECHNICAL FIELD

The present application pertains generally to medical systems and methods for creation of an autologous tissue valves within a mammalian body.

BACKGROUND

Venous reflux is a medical condition affecting the circulation of blood, such as in the lower extremities. The valves in the vessel that normally force blood back towards the heart cannot function properly. As a result, blood pools up in the legs, and the veins of the legs become distended. Applicant of the subject application determines that new systems and methods for treating venous reflux would be desirable.

SUMMARY

The present application relates generally to medical systems and methods for creation of an autologous tissue valves within a mammalian body.

In some embodiments, a system for creating an endoluminal valve from a blood vessel wall is provided. The system includes a tubular assembly having a longitudinal axis, a proximal end, a distal portion with a distal end, and a first lumen extending from the proximal end to a distal port located proximate the distal portion, the distal port located along the longitudinal axis, the distal portion having a supporting surface on the same side of the tubular assembly as the distal port, the supporting surface extending in a longitudinal direction and offset from a surface of the tubular assembly proximal the distal port and configured to contact the blood vessel wall; and a tissue dissection probe disposed within the first lumen, the tissue dissection probe having a fluid delivery lumen extending to a fluid delivery port located at the distal end of the tissue dissection probe, the tissue dissection probe adapted to be inserted into the blood vessel wall.

In some embodiments, the supporting surface is substantially parallel (e.g., within 15° or less) to the longitudinal axis of the tubular assembly.

In some embodiments, the supporting surface is substantially flat.

In some embodiments, the diameter of the needle is less than the thickness of the blood vessel wall.

In some embodiments, the tissue dissection probe is configured to extend out of the distal port in an orientation that is substantially parallel (e.g., within 15° or less) to the supporting surface.

In some embodiments, the supporting surface is offset from a longitudinal axis of the tissue dissection probe by about 0.010 inches (e.g., 0.010 inch±0.005 inch) to about 0.100 inches (e.g., 0.100±0.15 inch), the longitudinal axis of the tissue dissection probe extending through a tip portion of the tissue dissection probe.

In some embodiments, the supporting surface is offset from a longitudinal axis of the tissue dissection probe by about 0.015 inches (e.g., 0.015 inch±0.005 inch) to about 0.060 inches (e.g., 0.060±0.02 inch), the longitudinal axis of the tissue dissection probe extending through a tip portion of the tissue dissection probe.

In some embodiments, the supporting surface is offset from a longitudinal axis of the tissue dissection probe by about 0.020 inches (e.g., 0.020 inch±0.005 inch) to about 0.040 inches (e.g., 0.040±0.01 inch), the longitudinal axis of the tissue dissection probe extending through a tip portion of the tissue dissection probe.

In some embodiments, the supporting surface is offset from the surface of the tubular assembly configured to contact the blood vessel wall by about 0.1 mm (e.g., 0.1 mm±0.05 mm) to about 5 mm (e.g., 5 mm±2 mm).

In some embodiments, the supporting surface is offset from the surface of the tubular assembly configured to contact the blood vessel wall by about 0.5 mm (e.g., 0.5 mm±0.1 mm) to about 3 mm (e.g., 3 mm±1 mm).

In some embodiments, the supporting surface is offset from the surface of the tubular assembly configured to contact the blood vessel wall by about 0.75 mm (e.g., 0.75 mm±0.2 mm) to about 1.5 mm (e.g., 1.5 mm±0.5 mm).

In some embodiments, the tubular assembly includes a suction lumen having a suction port located on the distal portion of the tubular assembly, the suction lumen in communication with a suction source.

In some embodiments, the suction port is located distal the distal port.

In some embodiments, the suction port is located proximal the distal port.

In some embodiments, the tissue dissection probe includes a balloon located on a distal portion of the tissue dissection probe.

In some embodiments, the system further includes an expandable element that is slidably disposed over the tissue dissection probe.

In some embodiments, the system further includes a mouth widening element that is slidably disposed over the tissue dissection probe.

In some embodiments, the balloon is non-compliant.

In some embodiments, the balloon is semi-compliant.

In some embodiments, the balloon has a self-centering mechanism.

In some embodiments, the first lumen is adapted to receive a tissue securement device.

In some embodiments, the system further includes a second lumen and a tissue securement device disposed in the second lumen.

In some embodiments, the system further includes a mechanism configured to eject hydrodissection fluid ahead of the tissue dissection probe while the tissue dissection probe is advanced.

In some embodiments, the distal portion has a predetermined stiffness that is configured to reduce the amount of deformation of the distal portion in both a first direction and a second direction perpendicular to the first direction.

In some embodiments, the system further includes an expandable element located on the distal portion of the tubular assembly, the expandable element located on the opposite side of the tubular assembly as the distal port.

In some embodiments, the expandable element is selected from the group consisting of a balloon and a cage.

In some embodiments, a portion of the expandable element is located distal the distal port and a portion of the expandable element is located proximal the distal port.

In some embodiments, a method of creating an endoluminal valve is provided. The method includes conforming a first portion of a vessel wall to a supporting surface to create an offset between the first portion of the vessel wall and a second portion of the vessel wall, wherein both the first portion of the vessel wall and the second portion of the vessel wall are both oriented in substantially the same direction (e.g., within 15° or less from each other); inserting a tissue dissection probe into a transitory portion of the vessel wall between the first portion and the second portion of the vessel wall, without going entirely through the adventitia of the vessel wall, to create an inlet, the vessel wall having a plurality of layers; introducing hydrodissection fluid between the layers of the vessel wall to separate two layers of the vessel wall to form a pocket within the vessel wall; widening the inlet to form a first valve flap, wherein the tip of the valve flap is formed from the inlet and the body of the valve flap is formed from the pocket; and securing the first valve flap such that the body of the valve flap is separated away from vessel wall from which the flap was formed.

In some embodiments, the insertion depth and the angle of insertion of the tissue dissection probe into the vessel wall is controlled in part by the offset between the first portion of the vessel wall and the second portion of the vessel wall.

In some embodiments, the tissue dissection probe has a diameter that is less than the thickness of the vessel wall.

In some embodiments, the hydrodissection fluid is substantially sealed within the pocket prior to widening the inlet to form the first valve flap.

In some embodiments, the method further includes maintaining a fluid space in front of the tissue dissection probe by controlling the flow of hydrodissection fluid from the tissue dissection probe.

In some embodiments, the method further includes enlarging the pocket using hydrodissection.

In some embodiments, the method further includes enlarging the pocket by expanding an expandable element within the pocket.

In some embodiments, the supporting surface is substantially flat.

In some embodiments, the tissue dissection probe is inserted into the vessel wall in an orientation that is substantially parallel (e.g., within 15° or less) to the supporting surface.

In some embodiments, the offset is about 0.1 mm (e.g., 0.1 mm±0.05 mm) to about 5 mm (e.g., 5 mm±2 mm).

In some embodiments, the offset is about 0.5 mm (e.g., 0.5 mm±0.1 mm) to about 3 mm (e.g., 3 mm±1 mm).

In some embodiments, the offset is about 0.75 mm (e.g., 0.75 mm±0.2 mm) to about 1.5 mm (e.g., 1.5 mm±0.5 mm).

In some embodiments, the inlet is widened to about at least 180 degrees around the circumference of the vessel.

In some embodiments, the length of the pocket is about 1 (1±0.2) to about 2 (2±0.2) times the diameter of the vessel.

In some embodiments, the inlet is widened to about 180 degrees (e.g., 180 degrees±10 degrees) or less around the circumference of the vessel.

In some embodiments, the length of the pocket is about 0.5 (0.5±0.1) to about 1.5 (1.5±0.5) times the diameter of the vessel.

In some embodiments, the first valve flap is secured to a portion of the vessel wall that is opposite of the first valve flap.

In some embodiments, the first valve flap is loosely secured at about the center of the first valve flap edge.

In some embodiments, the first valve flap is tightly secured at a first location near the edge of the first valve flap and within about 5 (5±1) to about 40 (40±10) degrees of the first end of the edge of the first valve flap, and wherein the first valve flap is tightly secured at a second location near the edge of the first valve flap and within about 5 (5±1) to about 40 (40±10) degrees of the second end of the edge of the first valve flap.

In some embodiments, the first valve flap is tightly secured at about the center of the first valve flap edge to a second valve flap.

In some embodiments, the method further includes positioning a balloon within the inlet and inflating the balloon to widen the inlet.

In some embodiments, the method further includes suctioning fluid out of the vessel.

In some embodiments, the first portion of the vessel wall is conformed to the supporting surface by expanding an expandable element against a portion of the vessel wall opposite the first portion.

In some embodiments, the method further includes reducing the deformation of the supporting surface in both a first direction normal the supporting surface and a second direction perpendicular to the first direction by providing the supporting surface with a predetermined stiffness.

Other and further aspects and features will be evident from reading the following detailed description of the embodiments.

BRIEF DESCRIPTION OF THE DRAWINGS

The novel features of the embodiments are set forth with particularity in the claims that follow. A better understanding of the features and advantages of the embodiments will be obtained by reference to the following detailed description, and the accompanying drawings of which:

FIGS. 1A-1C illustrate two parascoping conduits each with an expandable member configured to straighten out a tortuous vessel and to create tautness in the vessel wall.

FIGS. 2A-2B illustrate two parascoping conduits each with wall engagement suction mechanism configured to straighten out a tortuous vessel and to create tautness in the vessel wall.

FIGS. 3A-3B illustrate a conduit mechanism with a puncture element configured to engage a vessel wall at some angle with some embodiments.

FIGS. 4A-4B and 5A-5D illustrate methods for gaining access into an intra-mural space with some embodiments of tissue puncture elements, dissection assemblies and hydrodissection.

FIGS. 6A-6B and 7A-7B illustrate embodiments of puncture elements and dissection probes configured to provide hydrodissection through both the puncture element and the distal nozzle of the dissection probe, with un-actuated and actuated configurations.

FIGS. 8A-8B illustrate a deflected point puncture element within dissection probe, in multiple orientations.

FIGS. 9A-9B illustrate two embodiments of bevel manufacturing on angled puncture elements.

FIG. 10 illustrates a pencil point trocar puncture element.

FIG. 11 illustrates a puncture element with a shovel-like geometry.

FIGS. 14B-14C illustrate an embodiment in which a puncture element is used as a dissection probe and itself holds a seal along the inlet of a vessel wall.

FIG. 15 illustrates a method for introducing large caliber instruments into an intra-mural space.

FIGS. 16A-16B illustrate a side and top view of a s-shaped conduit with flat supporting surface, configured to allow for advancement of a tissue dissector parallel to the vessel wall.

FIG. 16C illustrates a side view of an angled s-shaped conduit with flat supporting surface, configured to allow for advancement of a tissue dissector with a slight inward angle with respect to the vessel wall.

FIGS. 16H-16I illustrate a method for gaining access into a vessel wall by rotating the bevel of a puncture element.

FIGS. 18A-18C illustrate a tissue dissection probe, configured with multiple side ports and a distal port, and a flow-directing element, used for creating specific intra-mural pocket geometries, with multiple configurations FIG. 19 illustrates a handle mechanism connected to a fluid source configured to provide a mechanical advantage for providing a hydrodissection flow.

FIGS. 29A-29F illustrate a method for valve creation utilizing double conduit configuration with two expanding balloons and an offset tool lumen, and angled puncture element, and advancable pocket creation balloon.

FIGS. 36A-36B illustrate a bendable conduit with pull wire, configured to engage a vessel wall, with un-actuated and actuated configurations.

FIGS. 37A-37B illustrate two parascoping conduits configured to create a defined bend in the inner flexible conduit, configured to engage a vessel wall, with un-actuated and actuated configurations.

FIGS. 38A-38B illustrate a side view and top view of a multi-lumen conduit with two expanding balloons and a suction source for engaging a vessel wall in three locations for manipulation with a tool.

FIGS. 39A-39C illustrate a method for use of a valve creation device with puncture element, hydrodissection lumen and balloon coupled together as one.

FIGS. 40A-40C illustrate three embodiments of a bevel neutralizing mechanism on a puncture element configured with a balloon.

FIGS. 41A-41E illustrate a method for valve creation utilizing a tapered puncture element with tapered outer sheath. The puncture element is removed upon intra-mural access for use of an expanding balloon for valve creation.

FIG. 42 illustrates a tissue dissection probe with puncture tip, which is slidibly disposed within a probe configured with a valve creation balloon.

FIGS. 43A-43C illustrate a method for valve creation utilizing a tapered puncture element within an outer sheath with deformable curved distal tip. The puncture element is removed upon intra-mural access for use of an expanding balloon for valve creation.

FIGS. 44A-44C illustrate a puncture element configured with a stopper mechanism, and a balloon conduit to be inserted into an intra-mural space through the lumen of the puncture element.

FIGS. 45A-45C illustrate a mechanism configured to widen the inlet of an intra-mural pocket with use of a spirally expanding blade.

FIGS. 50A-50B illustrate a mechanism configured to widen the inlet of an intra-mural pocket with use of self-centering saddle geometry expanding balloon.

FIGS. 51A-51B illustrate a mechanism configured to widen the inlet of an intra-mural pocket with use of shape memory, upward bending cutters.

FIGS. 54A-54E illustrate a step-wise method for advancing a puncturing tissue dissection probe within a vessel wall, by maintaining a flow of fluid ahead of the bevel at all times during advancement.

FIGS. 55A-55C illustrate a method of puncturing a vessel wall to gain access into an intramural space, with use of a high flow narrow stream of fluid.

FIGS. 57A-57D illustrate a method of valve creation involving a stiff support mechanism, an opposing wall apposition balloon, a puncture element/tissue dissector advanced parallel to the vessel wall, followed by a slidibly configured tapered probe which houses a pocket creation balloon to be expanded to widen the inlet to create a competent valve.

DETAILED DESCRIPTION

Figure 12:
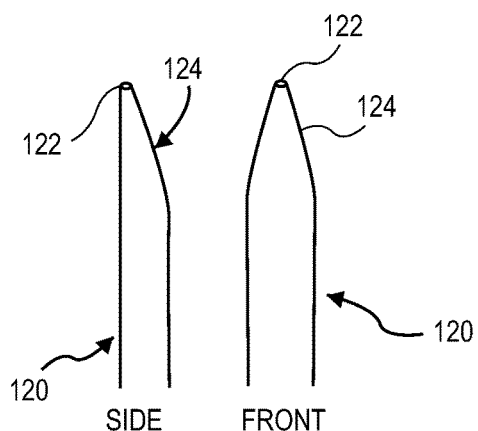
FIG. 12 illustrates a dissecting probe with a radially asymmetric geometry.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated or if not so described explicitly.

Methods for Straightening Out Tortuous Vessels are Described.

In accordance with some embodiments, as depicted in FIGS. 1A-1C, a method includes expanding an expandable member (such as a balloon or a cage) to a diameter greater than that of the native vessel 10 at a location both distal and proximal to a potential valve creation site, where distal and proximal are defined in relation to the operator. FIG. 1a depicts the expandable members 12, 14 before they are expanded/inflated. FIG. 1B depicts the proximal and distal expandable members 12, 14 after they are inflated to such a diameter that even za curved vessel is forced to take a straight path between the proximal and distal expandable members 12, 14 due to a created tension. The expandable members 12, 14 can be parts of a catheter 16, such as a balloon catheter, that can be introduced into the vessel using minimally invasive techniques.

In accordance with other similar embodiments, depicted in FIG. 1C, the proximal and distal expandable members 12, 14 previously described are expanded to a diameter greater than that of the native vessel 10 and then separated from each other some distance to create even more tension in the vessel wall 18, so that even a curved vessel is forced to take a straight path between the members 12, 14. In some embodiments, the expandable members 12, 14 can be incorporated into a single catheter 16 which is configured to telescope or change its length between the expandable members. In other embodiments, the expandable members 12, 14 are located on separate catheters 16, 17, which can be coaxial with each other or not coaxial with each other.

In accordance with some embodiments, as depicted in FIG. 2A, a method includes engaging a suction mechanism (or any wall engagement mechanism such as a hook or anchor, for example) to a vessel wall 18 at a location both distal and proximal to a potential valve creation site. This will act to straighten out the working side of the vessel (while the opposing luminal side may remain tortuous). FIG. 2B depicts how the proximal and distal suction mechanisms 20, 22 can then separated from each other some distance to create even more tension in the vessel wall 18, so that even a curved vessel is forced to take a straight path between the members 20, 22. In some embodiments, the suction members 20, 22 can be incorporated into a single catheter 16 which is configured to telescope or change its length between the suction members. In other embodiments, the suction members 20, 22 are located on separate catheters 16, 17, which can be coaxial with each other or not coaxial with each other.

In a related embodiment, the distal engagmenet mechanism is a suction mechanism, and the proximal engagement mechanism is an expansion mechanism (such as a balloon or cage).

In another related embodiment, the distal engagmenet mechanism is an expansion mechanism (such as a balloon or cage) and the proximal engagement mechanism is a suction mechanism.

In accordance with some embodiments, in addition to use of two engagement mechanisms to straighten out and create tautness in a vessel wall, a suction mechanism is utilized between the two engagement mechanisms to insure wall apposition for vessel wall manipulation within the engagement region. The suction mechanism can withdraw fluid from between the two engagement mechanisms, which causes the vessel wall to collapse inwards against the engagement mechanisms.

In addition to straightening out a tortuous vessel, the methods described above can also be utilized to cause a tautness in the vessel wall to facilitate techniques such as vessel wall puncture and hydrodissection for the purpose of creating autologous valves.

All embodiments described in FIGS. 1A-1C and 2A-2B, which may include expansion mechanisms and suction mechanisms for engaging and changing the orientation of a vessel wall, can be used in combination with other components described for valve creation. Most of this is done through a side port 19 on the catheter 16. The rest of the valve creation procedure is depicted in FIGS. 29A-29F at the bottom of the description. The embodiments depicted here can be used in combination with these or similar techniques to create a full valve geometry.

In accordance with some embodiments, as depicted in FIG. 3A, the method involves advancing a tubular structure 16, such as a catheter with at least two engagement mechanisms for example, into a vessel 10 and activating it in a way to change the vessel 10 from a tortuous geometry to that of a known shape that may not necessarily be straight. For example, some embodiments include creating a tautness in a vessel wall 18 by engagement of the vessel wall 18 in two locations with a tubular structure 16 having a distal portion with a slight curve which is more stiff than the vessel wall 18. Engagement of the tubular structure 16 with the vessel 10 causes the vessel 10 to curve slightly at approximately an angle a with respect to the longitudinal axis L of the catheter 16. This method allows a tissue manipulating element 24 to approach the vessel wall 18 at a known angle a by advancement through a side port 26 of the tubular structure 16 that more or less maintains the angle of the more proximal axial shaft of the tubular structure 16. In other words, the tissue manipulating element 24 (depicted here as a needle) exits the side port 26 approximately along the longitudinal axis L of the tubular structure 16 and penetrates the vessel wall 18 which is oriented approximately at an angle a with respect to the longitudinal axis L. In some embodiments, the angle a is between about 0 and 30 degrees, or about 1 to 10 degrees or about 2 to 5 degrees. Utilizing the tissue manipulating or penetrating element 24, this embodiment can then be used in combination with other components described for valve creation. An example of one way in which to combine embodiments to complete the valve creation procedure is depicted in FIGS. 29A-29F at the bottom of this disclosure. The embodiments depicted here can be used in combination with these or similar techniques to create a full valve geometry.

In other embodiments as illustrated in FIG. 3B, the tubular structure 16 can remain substantially straight along with the vessel 10, and the side port 26 can be angled such that the tissue manipulating element 24 exits the side port 26 at approximately an angle a with respect to the longitudinal axis L and the vessel wall 18. In some embodiments where balloons are used as the engagement mechanisms, the tubular structure 16 can be offset from the central axis of the engagement mechanisms such that the side port 26 is proximate the vessel wall 18 when the engagement mechanisms are engaged with the vessel wall 18. Utilizing the tissue manipulating or penetrating element 24, this embodiment can then be used in combination with other components described for valve creation. An example of one way in which to combine embodiments to complete the valve creation procedure is depicted in FIGS. 29A-29F at the bottom of this disclosure. The embodiments depicted here can be used in combination with these or similar techniques to create a full valve geometry.

In accordance with some embodiments as illustrated in FIGS. 30A-E and 31, a device 3000 for manipulating tissue at a vessel includes a conduit 3002 having a proximal 3020 and distal end 3012 and at least two internal lumens 3004, 3006. One internal lumen 3004 serves the function of directing tools 3008 such as a tissue engagement device, a tissue cutting device, a hydrodissecting probe device, or a pocket creation balloon. The tool 3008 can be manipulated from the proximal end. This tool lumen terminates near the distal end 3012 of the catheter in such a way as to contact the internal lumen of a vessel at a specific location and a specific angle. The other internal lumen 3006 of the conduit 3002 is connected to a suction source near the proximal end and is in fluid communication with one or more exit ports 3010 near the distal end 3012 of the conduit 3002. In this way, negative pressure suction can be actuated over a specified area near the distal end 3012 of the catheter. In this way, the distal end 3012 of the catheter has the ability to move bodily tissues (such as lumen walls) within a certain non-zero distance to a specific orientation along the conduit surface. The act of suction against a bodily tissue also acts to hold the tissue in place during a manipulation through the tool lumen 3004. Additionally, the act of suction against a bodily tissue also acts to impart a tautness to the bodily tissue due to the multiple locations of the exit ports 3010 at which suction is imparted on the tissue. Finally, in accordance with some embodiments, this conduit device 3000 has a specific geometry near its distal end 3012, which forces the tissue to conform along a specific geometry upon the application of suction. By forcing a specific geometry of the bodily tissue (e.g. a lumen wall), certain tools 3008 are allowed to be passed through the tool lumen 3004 of the conduit 3002 contact the tissue at a specific location and at a specific angle, without having to take a curved geometry itself upon exiting the distal port of the tool lumen 3004.

In accordance with some embodiments, the geometry of the distal tip 3012 of the conduit 3002 forces the tissue along an angle between 5° and 90° off the axis of the conduit surface itself. In some preferred embodiments, the geometry of the distal tip 3012 of the conduit 3002 forces the tissue along an angle between 20° and 40° off the axis of the conduit surface itself.

In accordance with some embodiments, the geometry of the distal tip 3012 of the conduit 3002 is such that the tissue conforms inward toward the surface of the sloping portion 3014 of the conduit 3002, but is then forced out again by a more distal surface of the conduit 3002. In such an embodiment, the orientation of the tool lumen 3004 is such that the engagement mechanism or cutting mechanism tool may puncture through bodily once or twice depending on the thickness of the tissue. Additionally this geometry allows the outward sloping section of the conduit surface to act as a "backboard" structural support 3016, which will help with engagement, cutting, or control of bodily tissue.

Figure 30:
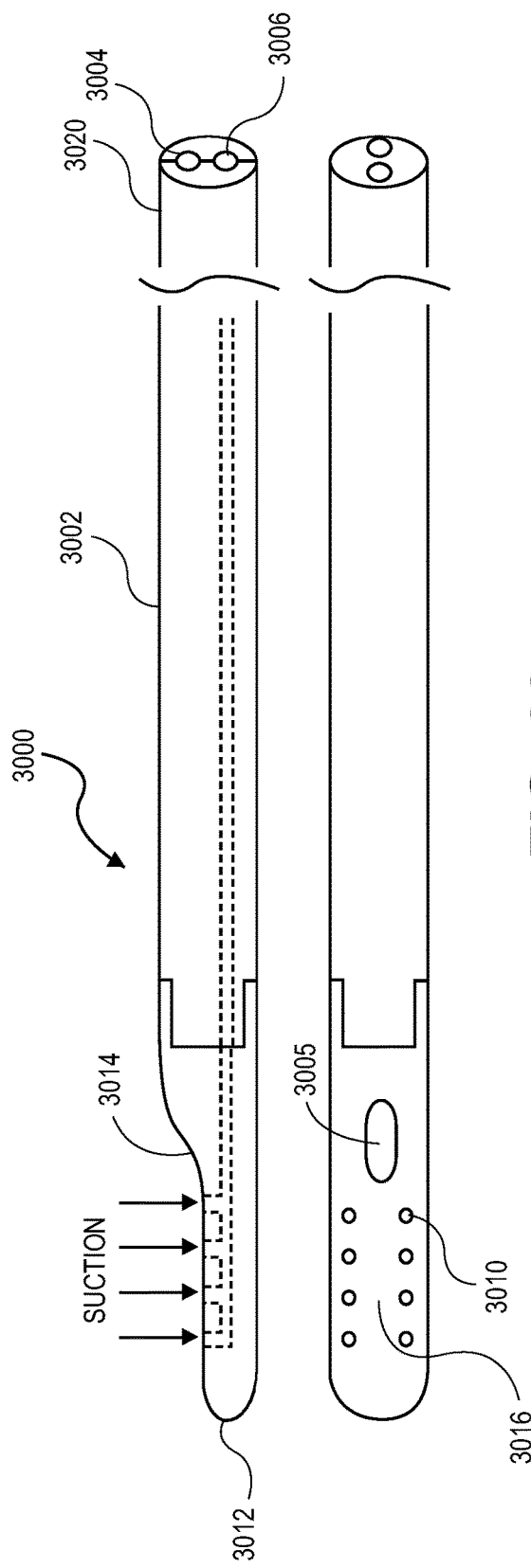
FIG. 30 illustrates a side and top view of a conduit with two lumens configured with the capability to engage a vessel wall with suction.
Figure 31:
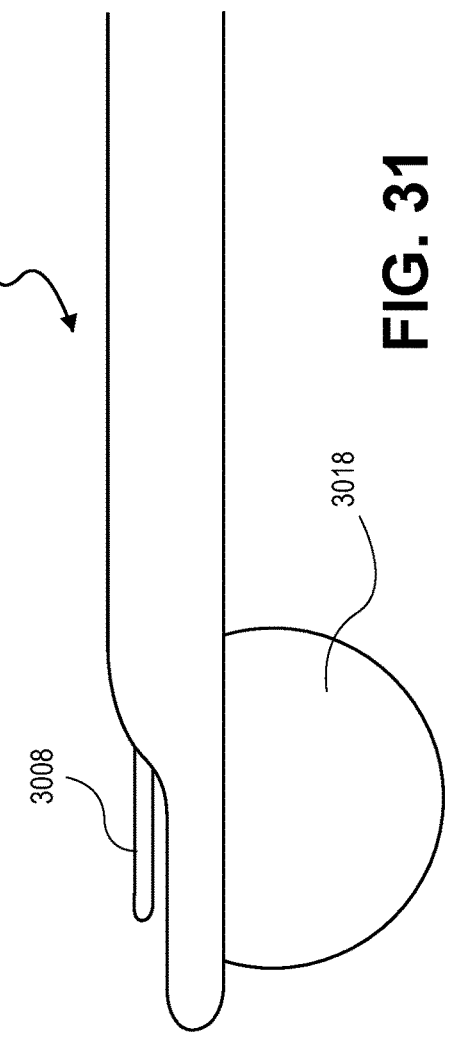
FIG. 31 illustrates a side view of a conduit with a tissue dissection probe and a balloon configured to engage a vessel wall.

In accordance with some embodiments, the suction exit ports 3010 are distributed off the axis from the tool lumen 3004 at positions proximal and distal to the tool exit port, as shown in FIG. 30. This off-center placement prevents the introduction of a tool 3008 to the bodily tissue from disengaging the tissue from contact suction.

In accordance with some embodiments, the conduit 3002 is equipped with a third lumen to house a sideways facing complaint balloon 3018. This balloon 3018 can be utilized to maintain the axial location of the conduit 3002 within a bodily lumen. Additionally this balloon 3018 can be utilized to create a tautness in the lumen wall. Additionally this balloon 3018 (potentially in tandem with another distal balloon) can be utilized to evacuate a section of a lumen of blood or to prevent blood from flowing past the single balloon, for the purpose of facilitating the procedure. Additionally the balloon 3018 can be used to help force the distal suction portion of the conduit toward a lumen wall so that it may more consistently engage the lumen wall.

In accordance with some embodiments, the conduit 3002 has a flexible section proximal to the suction exit ports 3010 and the tool lumen exit port 3005. This flexible section allows the distal tip 3012 of the conduit 3002 to bend toward a lumen wall so that suction may more consistently engage the lumen wall.

In accordance with some embodiments, this flexible section can be actuated from the proximal end by the user to actively force the suction ports 3010 toward the lumen wall.

In accordance with some embodiments, a sideways facing complaint balloon 3018 is mounted on the side of the conduit itself.

In accordance with some embodiments, the sideways facing balloon 3018 is positioned proximal to the exit port 3005 of the tool lumen 3004 and the exit ports 3010 of the suction lumen 3006.

In accordance with some embodiments, the sideways facing balloon 3018 is positioned at the same axial location as the exit port 3005 of the tool lumen 3004 and the exit ports 3010 of the suction lumen 3006.

In accordance with some embodiments, the sideways facing balloon 3018 is inflated such that it contacts a lumen wall nearly directly 180° opposite the exit port 3005 of the tool lumen 3004.

In accordance with some embodiments, as illustrated in FIGS. 34A-35B, a device 3400 for manipulating tissue at a vessel includes a conduit 3402 having a proximal and distal end 3404, 3406 and at least two or three internal lumens, 3408, 3410, 3412. FIG. 34B depicts the cross section of an embodiment of such a device with three internal lumens. One internal lumen 3408 serves the function of directing tools (such as a tissue engagement device, a tissue cutting device, a hydrodissecting probe device, or a pocket creation balloon). The tool can be manipulated from the proximal end. This tool lumen 3408 terminates near the distal end 3406 of the catheter in such a way as to contact the internal lumen of a vessel at a specific location and a specific angle. Another internal lumen 3410 of the conduit is connected to a suction source near the proximal end 3404 and is in fluid communication with one or more exit ports 3414 near the distal end 3406 of the conduit 3402. In this way, negative pressure suction can be actuated over a specified area near the distal end 3406 of the catheter. In this way, the distal end 3406 of the catheter has the ability to move bodily tissues (such as lumen walls) within a certain non-zero distance to a specific orientation along the conduit surface. The act of suction against a bodily tissue also acts to hold the tissue in place during a manipulation through the tool lumen 3408. Additionally, the act of suction against a bodily tissue also acts to impart a tautness to the bodily tissue due to the multiple locations (exit ports 3414) at which suction is imparted on the tissue. The third internal lumen 3412 houses a balloon to be deployed out of a side port 3416 in the device to provide tension to the lumen walls and/or longitudinal support for the device. A side cross-sectional view of this configuration can be seen in FIG. 34A.

In some embodiments the conduit 3402 may only have two lumens, as wall control may be obtained with only a balloon or only suction. In these embodiments the second internal lumen can be utilized as a tool lumen 3408.

The ability of this mechanism to hold suction on a lumen wall amidst static intravenous blood pressure depends on many factors. The following device embodiments facilitate the ability of this type of geometry to hold suction.

Figure 35A:
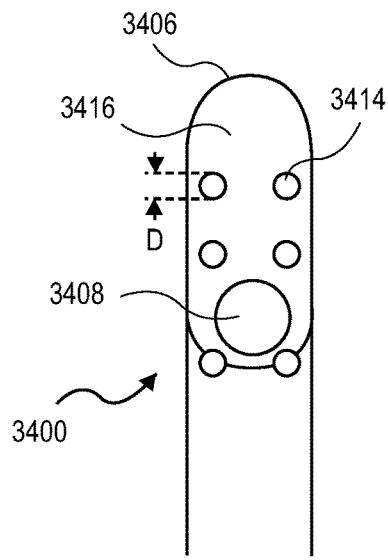
FIGS. 35A-35B illustrate a front and side cross-section view of a three lumen conduit configured to accept a balloon, suction, and tools.
Figure 35B:
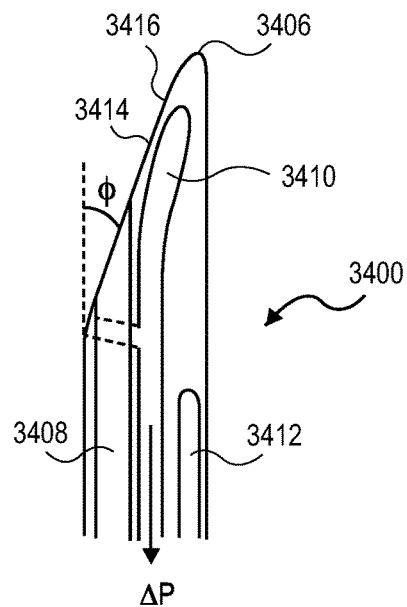

FIGS. 35A and 35B depict side and front views of a type of embodiment geometry. FIG. 35A depicts the placement of suction ports 3414 with diameter D along the distal tip 3406 of the elongated device. The size of these ports 3414 can be optimized to ensure proper suction. In some preferred embodiments these holes have diameter between 0.1 mm and 1 mm. In other, preferred embodiments, these holes have diameter between 0.3 mm and 0.5 mm. Other factors contributing to suction ability are the number of suction ports 3414, the placement of suction ports 3414 and the shape of suction ports 3414. These can be tweaked and optimized for optimal suction. In some embodiments, as many as 40 suction ports may be used, covering a total of 50% of the surface of the distal end of the device. In some embodiments, horizontal rectanglular suction ports are used. In other embodiments, vertical rectangular suction ports are used running off the mid-line of the device (away from the port 3408) FIG. 35B depicts two other parameters that effect the success of suction. The angle (theta) shown, which is the angle of the sloped portion 3416 and the longitudinal axis of the device, can be chosen to be small to allow for a more gradual bending of the lumen wall. In some embodiments this angle may be as small as 5 degrees. In others this angle may be as large 45 degrees. Another important parameter is the pressure differential caused by the source of suction. This can be increased as desired to increase the ability of the suction mechanism to latch onto the luminal wall. In some embodiments, as much as 150-200 mmHg is used. In other embodiments, between 100-150 mmHg is used. In other embodiments, between 50-100 mmHg is used. In some embodiments, potentially using a portable suction source, between 5-50 mmHg is used.

In accordance with some embodiments, as illustrated in FIGS. 36A-37B, the distal neck of the conduit can be made to allow the distal most tip, and therefore suction surface of the conduit to oppose the wall with some normal force and at a more optimal angle.

In accordance with some embodiments, as illustrated if FIGS. 36A and 36B, the distal neck 3602 of the conduit 3600 is made from a flexible material. In some embodiments this material may simply lack stiffness due to the material used or the thickness of the wall. In other embodiments this flexible neck portion 3602 is created by using an accordion-like geometry 3604 in a small section of the conduit surface. In many such embodiments, the distal tip 3606 of the conduit 3600 is then allowed or forced to cock off-axis to an angle non-parallel to that of the conduit shaft, until it contacts the inner wall of the lumen. In one such embodiment, as depicted in FIGS. 36A and 36B, an internal pullwire 3608 that can be threaded through the tool lumen 5610 (off the central axis) can be pulled taut from the proximal end to actively force the distal tip 3606 of the conduit 3600 to bend into the lumen wall. In other similar embodiments, the distal tip 3606 of the conduit 3600 can bend passively in the presence of flowing blood until it contacts and latches onto the lumen wall.

FIGS. 37A and 37B depict a similar embodiment in which two parascoping conduits 3700, 3702 are utilized to provide a similar effect. The outer, tubular conduit 3700 houses a balloon 3704 (if necessary), and has a fixed bend 3706 at the distal end 3708. The inner conduit 3702 houses a tool lumen 3709 and a suction lumen 3710 and much of the same geometry as previously described in the conduit mechanism. The inner conduit 3702 is flexible enough to take the bend 3706 forced by the outer tubular conduit 3700 such that upon relative advancement of the inner conduit 3702, it is pushed forward and sideways until it contacts the lumen wall with the suction surface 3711.

FIGS. 38A and 38B depict an embodiment in which the conduit mechanism 3800 has a proximal and distal balloon 3802, 3804 that can be inflated to completely occlude the lumen in two places. In between these two balloons 3802, 3804, the conduit 3800 can have a recessed geometry 3806, which exposes the outlet 3808 of the tool lumen 3810. Additionally, suction ports 3812 are placed on and/or near this recess to force the luminal wall to conform to the geometry of the recess 3806. This is facilitated by the lack of static blood pressure in the working segment. Additionally, in the embodiment shown, the conduit 3800 is placed off-center with respect to both balloons 3802, 3804, such that the recess 3806 of the conduit 3800 is as close to the luminal wall as possible. Upon inflation of the balloons 3802, 3804, suction can be initiated to evacuate the working segment of the lumen of blood and other fluids.

Methods and Mechanisms for Creating Controlled Pocket Geometries within a Vessel Wall (Puncture and Initial Entry)

In accordance with some embodiments describing controlled tissue dissections, a tissue dissection assembly is described. This assembly may be used (but is not limited to use) in conjunction with other embodiments previously described (in this disclosure and previous disclosures such as U.S. Publication No. 20110264125 and U.S. application Ser. No. 13/035,752, which are hereby incorporated by reference in their entireties for all purposes). In many embodiments of the valve creation assembly, this controlled dissection assembly is advanced out of an exit port of a tubular assembly, which itself insures that the dissection assembly approaches the vessel wall at a desired and controlled angle. Additionally, the tubular assembly may also force a local tension in the vessel wall, so that the controlled dissection assemblies, which are described further below, can be maximally effective and consistent. In other embodiments, the controlled dissection assemblies may be used as stand alone tools, that are delivered to a location in a vessel and enter a vessel wall as designed without the need for supporting structures.

In accordance with some embodiments of a controlled dissection assembly, a puncture element is designed to move parascopically out of an exit port at the distal end of a tissue dissection probe, which is otherwise blunt when the puncture element is retracted. In this way, multiple methods can be employed to gain sub-intimal access in a vessel wall. This controlled dissection assembly may be advanced from a side port at or near the exit of a support catheter. All embodiments described in this section for gaining controlled access into a subintimal space (covering FIGS. 4A-12 and all associated text that may or may not describe embodiments depicted in figures), can be used in combination with other components described for full valve creation. An example of one way in which to combine embodiments to complete the valve creation procedure is depicted in FIGS. 29A-29F at the bottom of this disclosure. The embodiments depicted here can be used in combination with these or similar techniques to create a full valve geometry.

As illustrated in FIGS. 4A-4B, some methods exist in which the tissue dissection assembly/probe 40 is butted up against the inner surface of a vessel wall 42 at a known angle β which is between about 0 and 30 degrees, or about 1 to 10 degrees or about 2 to 5 degrees, while the puncture element 44 is within the probe 40 entirely. Upon actuation, the puncture element 44 is then forced out of the distal exit port 46 of the tapered probe 40 by between about 0 mm and 5 mm, or about 0.5 mm and 3 mm, or about 0.75 mm and 2 mm, or about 1 mm and 1.5 mm, so as to puncture the vessel wall 42 but not to go through it.

In some such embodiments, the blunt probe 40 is stationary with respect to the vessel wall 42 during actuation.

In other such embodiments, the blunt probe 40 is dragging along the vessel wall 18 at the time of actuation of the puncture element.

In some such embodiments, a hydrodissecting agent 48, such as saline, water for injection, contrast solution, hydrogel, or any other fluid agent that is beneficial for separating tissue layers is forced through the puncture element 44 during puncture to begin separating tissue layers within the vessel wall 42 (FIGS. 4A-4B).

In another such embodiment, the vessel wall 42 is punctured, and then a hydrodissecting agent 48 is forced through the puncture element 44 to begin separating tissue layers within the vessel wall 42.

In another similar set of embodiments, some methods exist in which the probe 50 is butted up against the inner surface of a vessel wall 52 at a known angle β, which is between about 0 and 30 degrees, or about 1 to 10 degrees or about 2 to 5 degrees, while the puncture element 54 is within the probe 50 entirely. Upon actuation, the puncture element 54 is then forced out of the distal exit port 56 of the tapered probe 50 a small distance so as to puncture the vessel wall 52 but not to go through, and then is immediately (automatically or with further user actuation) retracted back into the probe 50, with a quick motion. In some such embodiments, the blunt probe 50 is then advanced into the wall defect 58 created by the puncture element 54. Upon entry into the wall defect 58, or during entry into the wall defect 58, a hydrodissecting agent 60 is then forced through a lumen within the probe 50 to begin separating tissue layers within the wall 52 (FIGS. 5A-5D).

In another similar set of embodiments, some methods exist in which a support catheter with a side port is butted up against the inner surface of a vessel wall, such that when a tissue dissection probe with deployed puncture element is advanced from the side port, it contacts the wall at a known angle.

In another similar set of embodiments, some methods exist in which a support catheter with a distal exit port is butted up against the inner surface of a vessel wall, such that when a tissue dissection probe with deployed puncture element is advanced from the side port, it contacts the wall at a known angle.

In many of the method embodiments described, a mechanism that allows for different configurations of retractable puncture elements within a tissue dissection probe is provided, and a method for ejecting a fluid in different configurations is also provided.

One possible configuration exists in which the hydrodissection agent is administered through the puncture element, either while the puncture element is deployed or while the puncture element is retracted to within the hollow, blunt probe, as illustrated in FIGS. 4A-4B and 5A-5D.

One possible configuration exists in which the puncture element 62 is comprised of a sharpened hollow tube with a length between about 0 mm and 7 mm, or about 1 mm and 4 mm, or about 2 mm and 3 mm. This hollow tube 62 is attached to a solid push rod 64 on its proximal end. In this way, the hollow lumen of the puncture element is open on the bottom (not fully obstructed by the presence of the push rod). The dissection probe 60 is configured with a smaller ID at the distal exit port 66, and with a slightly larger ID within the more proximal part of the lumen 68 of the dissection probe 60, thereby resulting in a tapering distal tip portion. The ID of the distal exit port 66 is made to very tightly match the OD of the puncture element 62, such that when the puncture element 62 is deployed out of the distal port 66 of the probe 60, flow through the lumen 68 of the dissecting probe 60 can flow around the push rod 64, into the hollow lumen of the puncture element 62, and out the distal end of the puncture element 62. When the push rod 64 is retracted such that the puncture element 62 is within the lumen 68 of the dissecting probe 60, flow through the lumen 68 of the dissecting probe 60 flows around the puncture element 62 and through the puncture element 62 and out of the full ID of the distal port 66 at the distal end of the dissection probe 60, thus allowing the velocity of the jet of dissection fluid out of the dissection probe 60 for a given pressure to be lower than when the puncture element 62 is deployed out of the distal port 66 (FIGS. 6A-6B).

Another possible configuration, of the dissection probe 70 exists with a similar configuration, but with a full length tubular puncture element 72, such that when the puncture element 72 is deployed out of the distal port 74, fluid can only go through and exit the lumen of the puncture element 72, but when the puncture element 72 is retracted, fluid can go through the lumen of the puncture element 72 and around the puncture element 72 and exit the distal port 74 (FIGS. 7A-7B).

Another possible configuration exists in which the puncture element has a solid sharp point and is made to be retractable such that when deployed the puncture element extends out of the distal exit port of the dissecting probe and cannot eject a hydrodissecting fluid due to its solidity. In other words, the solid puncture element forms a plug in the distal exit port when the puncture element fully extends out of the distal exit port. Then, when the puncture element is retracted a certain distance into the dissecting probe, fluid is automatically directed around the puncture element and out of the distal exit port of the dissecting probe. In one potential manifestation of this embodiment, the puncture element is comprised of a sharpened solid rod. This solid rod can be retracted to within the internal lumen of the dissecting probe. The dissection probe is configured with a smaller ID at the distal exit port, and with a slightly larger ID within the more proximal part of the lumen, giving the dissection probe a tapered distal end portion. The ID of the distal exit port is made to very tightly match the OD of a distal portion of the puncture element, such that when the puncture element is deployed out of the distal port of the probe, fluid cannot flow out of the dissecting probe. When the puncture element is retracted to within the lumen of the dissecting probe, flow through the lumen of the dissecting probe flows around the puncture element and out of the distal end of the dissecting probe.

In accordance with many embodiments of the controlled dissection assembly, specific geometries of puncturing elements may be advantageous.

In some embodiments, a deflected point puncture element 80 is used for controlling the direction of advancement of the tissue dissection probe 82. The deflected point puncture element 80 may be used in combination with all other embodiments previously described. For example, it may be used in combination with a tubular assembly with expansion elements, such that it is pushed out of an exit port toward or into a vessel wall.

In some embodiments, the angular deflection off the axis of the shaft of the dissection probe 82 is between about 0° and 15°, or about 2° and 10°, or about 4° and 7°. By rotating of the puncture element 80, the direction of advancement within the intra-mural dissection plane can be altered to be toward the center of the lumen or away from the center of the lumen (FIGS. 8A and 8B).

In some embodiments the bevel 90 of the puncture element 92 is angled toward the deflection, and in some embodiments the bevel 90 of the puncture element 92 is angled away form the deflection (FIGS. 9A and 9B).

In a similar embodiment, the tissue dissecting probe itself is slightly bent near the distal tip, so that rotation of this probe could serve the function of directing the direction of advancement slightly toward or away from the center of the lumen. In some embodiments this deflection of the puncture element or probe is located within about 4 mm of the distal tip. In some embodiments, the deflection is located within about 8 mm, or about 4 to 8 mm, of the distal tip.

In some embodiments, a pencil point trocar device 100 is used in a similar manner to descriptions of other embodiments of puncture elements. This geometry may contain an internal lumen so that it may also be used in conjunction with subsequent hydordissection through the probe lumen after puncture (FIG. 10). The pencil point trocar device 100 may be used in combination with all other embodiments previously described. For example, it may be used in combination with a tubular assembly with expansion elements, such that it is pushed out of an exit port toward or into a vessel wall.

In some embodiments, a shovel like geometry 112 is used to help skive the vessel wall so that as thin a flap as possible is created in the vessel wall. A hollow lumen within this probe may then be used for hydrodissection after creating this wall defect, much like in other embodiments described (FIG. 11). The puncture element with shovel like geometry 112 may be used in combination with all other embodiments previously described. For example, it may be used in combination with a tubular assembly with expansion elements, such that it is pushed out of an exit port toward or into a vessel wall.

In accordance with many embodiments of the controlled dissection assembly, a dissecting probe 120 with radially asymetric geometry is used. In this way, a puncture element protruding from the distal tip 122 will contact a vessel wall (even at a very shallow angle) prior to the full diameter of the probe proximal to the taper 124 (FIG. 12). This radially asymmetric dissecting probe may be used in combination with a puncture element (such as a trocar device or other previously described embodiment). This combination of elements, may itself be used in combination with all other embodiments previously described. For example, it may be used in combination with a tubular assembly with expansion elements, such that it is pushed out of an exit port toward or into a vessel wall.

Methods and Mechanisms for Creating Controlled Pocket Geometries within a Vessel Wall (Intra-Mural Space Creation and Access into Space)

In accordance with all embodiments for the creation of an intra-mural potential space, and access to that space, the mechanisms described can be advanced from a side port at or near the exit of a support catheter (although they man not always be depicted as such for simplicity). All embodiments described for creation of a geometry of intra-mural potential space (covering FIGS. 13A-19 and all associated text that may or may not describe embodiments depicted in figures), can be used in combination with other components described for full valve creation, including expansion mechanisms for wall control, and mouth opening balloons for full valve creation. An example of one way in which to combine embodiments to complete the valve creation procedure is depicted in FIGS. 29A-29F at the bottom of this disclosure. The embodiments depicted here can be used in combination with these or similar techniques to create a full valve geometry.

In accordance with some embodiments of a controlled dissection assembly, a method includes advancing a probe into a vessel wall a minimal amount. The probe then expels a pressurized hydrodissection agent (saline or saline with a contrast agent, or a hydrogel, or water for injection) from its distal tip to separate the intimal tissue layer from the medial tissue layer, or the medial layer from the adventitial layer, or a fibrosis layer from the intimal layer, or a sub-medial layer from another sub-medial layer, or a sub-adventitial layer from another subadventitial layer. This propagates distally from the distal end of the probe. In this way, a tissue pocket is formed without the need to further advance the probe into the wall, as long as sufficient flow is provided, and the pocket created is free from a significant leak at the top of the pocket (at probe entry), or from a hole leading into the lumen or extravascular space. In this way a fluid sealed pocket is formed with only one opening at the entry point. In some embodiments, a typical hydrodissection flow is between 0.25 cc/second and 3 cc/second. In other embodiments, a typical hydrodissection flow is between 0.5 cc/second and 2 cc/second. In other embodiments, a typical hydrodissection flow is between 0.75 cc/second and 1.25 cc/second.

In accordance with such embodiments, a seal is created at the opening in the vessel wall during the hydrodissection. The seal prevents the hydrodissection fluid from leaking back out into the lumen of the vessel, thus maintaining a high enough pressure within the wall to perform a proper dissection.

Figure 13A:
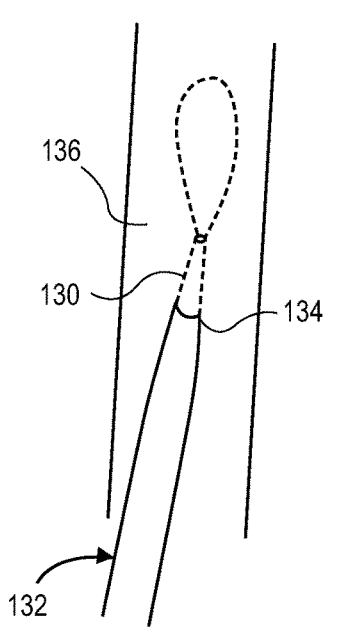
FIGS. 13A-13C illustrate three embodiments of a dissecting probe configured with a mechanism to hold a seal around the inlet to a vessel wall during a hydrodissection technique.

In one such embodiment, the distal nose 130 of the probe 132 is tapered so that a seal 134 can be created between the probe 132 and the vessel wall opening, simply by maintaining forward force against the wall 136 (FIG. 13A).

Figure 13B:
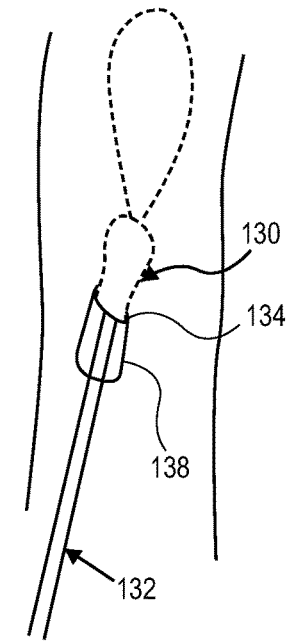

In another such embodiment, the distal end 130 of the probe 132 is equipped with an inflatable member 138, which is inflated just enough so as to ensure a seal 134 at the inlet of the wall defect (FIG. 13B).

Figure 13C:
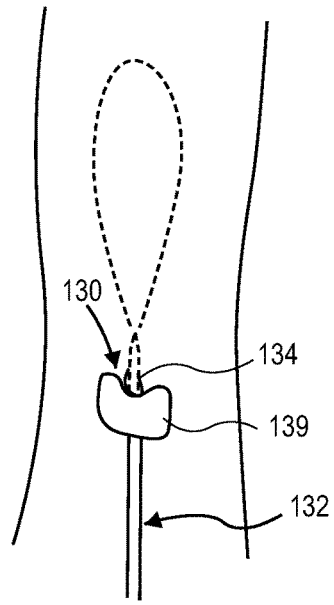

In another such embodiment, the distal end 130 of the probe 132 is equipped with a saddle shaped bulge or collar 139 made of a conformable material like silicone, which bottoms out in the wall inlet, creating a static seal 134 (FIG. 13C).

In other similar embodiments, upon entering the vessel wall, the probe is advanced further into the wall while expelling a hydrodissective agent from its distal end initially. In this way, the expulsion of fluid acts to both separate tissue layers, and physically move the outer portion of the vessel wall away from the tip of the probe, thus preventing the distal tip of the probe from touching and/or piercing the outer layer of the vessel wall. In some embodiments, the external surface of the probe has a hydrophilic or otherwise slippery surface or coating.

In accordance with such embodiments, a sliding seal is created at the opening in the vessel wall during the hydrodissection and probe advancement. The seal prevents the hydordissection fluid from leaking back out into the lumen of the vessel, thus maintaining a high enough pressure within the wall to perform a proper dissection.

In one such embodiment, the entire advanceable probe length has a slight taper, so that as the probe is advanced, a tight seal is always maintained between the probe and the inlet to the wall.

In another such embodiment, the entire advanceable length of the probe is equipped with an inflatable member, which is inflated just enough so as to ensure a seal at the inlet of the wall defect. In this sliding embodiment of the balloon seal, the balloon is made of a noncompliant or semi-compliant material so that a relatively flat surface is maintained.

Figure 14A:
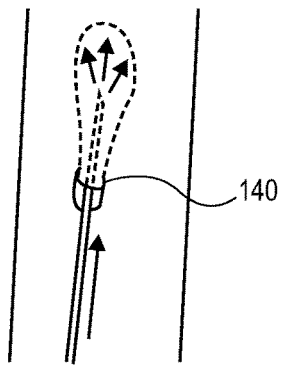
FIG. 14A illustrates an embodiment of a dissection probe with a tapered shape to hold a seal around the inlet to a vessel wall during a hydrodissection technique.

In a similar embodiment, the inflatable member 140 inflates to a tapered shape (FIG. 14A).

In a similar embodiment, as depicted in FIGS. 14B and 14C, a puncture element 141, which has a constant diameter proximal to the bevel at the distal tip 142, holds a sufficient seal along the inlet 143 during hydrodissection, and thus can be used as an initial probe to penetrate to a proper depth within the vessel wall 144 by being advanced while expelling a hydrodissection fluid 145. A valve creation mechanism can then be advanced over this puncture element when necessary 146.

In accordance with various embodiments, it may be necessary to gain access within the vessel wall 150 with a significant diameter instrument. In some embodiments, a small tissue dissection probe 152 is introduced into the intra-mural space via hydrosection techniques described. Then, a series of stepped dilators 154 can be passed over the original tissue dissection probe until a large enough diameter has been reached. Then, a thin walled sheath 156 can be placed over the largest dilator. Then, all dilators and the tissue dissection probe from within can be removed, leaving a large diameter access sheath within the vessel wall 150 (FIG. 15).

In accordance with some embodiments, a support mechanism 1600 is described to aid in the direction of advancement 1610 of a tissue dissection probe within the vessel wall 1620 by controlling the angle of the vessel wall 1620. In one embodiment, a sufficiently stiff, flat surface 1640 along the distal portion of the supporting tubular assembly 1660 exists to ensure the vessel wall 1620 does not bend inward toward the lumen, and thus preventing the advancement direction of the tissue dissection probe 1610 from pointing outward through the adventitia (FIG. 16A). This embodiment of the support mechanism 1600 is shown in cross-section (at the distal portion 1660) in FIG. 16B, depicting the flatness of the flat surface 1640. The depiction shows the vessel wall 1620, which rests against the flat surface 1640, as it is made to conform to a flat orientation. The transitory portion of the tubular assembly between the distal portion and the proximal portion can be s-shaped so that the flat surface 1640 of the distal portion is offset from the port at the distal end of the proximal portion of the tubular assembly 1660. The degree of offset can control the penetration depth of the tissue dissection probe. For example, the offset can be between about 0.1 mm to 5 mm. In other embodiments, the offset can be between about 0.5 mm to 3 mm. In other embodiments the offset can be between about 0.75 mm and 1.5 mm. A similar embodiment includes a flat surface 1640 along the distal portion of the supporting tubular assembly 1660, which is angled outward, away from the center of the lumen by between about 0° and 15°, or about 1° and 10°, or about 2° and 6°. This structure ensures that the path of the tissue dissection probe is close to the axis of the vessel wall, but with a slight bias toward the intraluminal side (FIG. 16C).

Figure 16D:
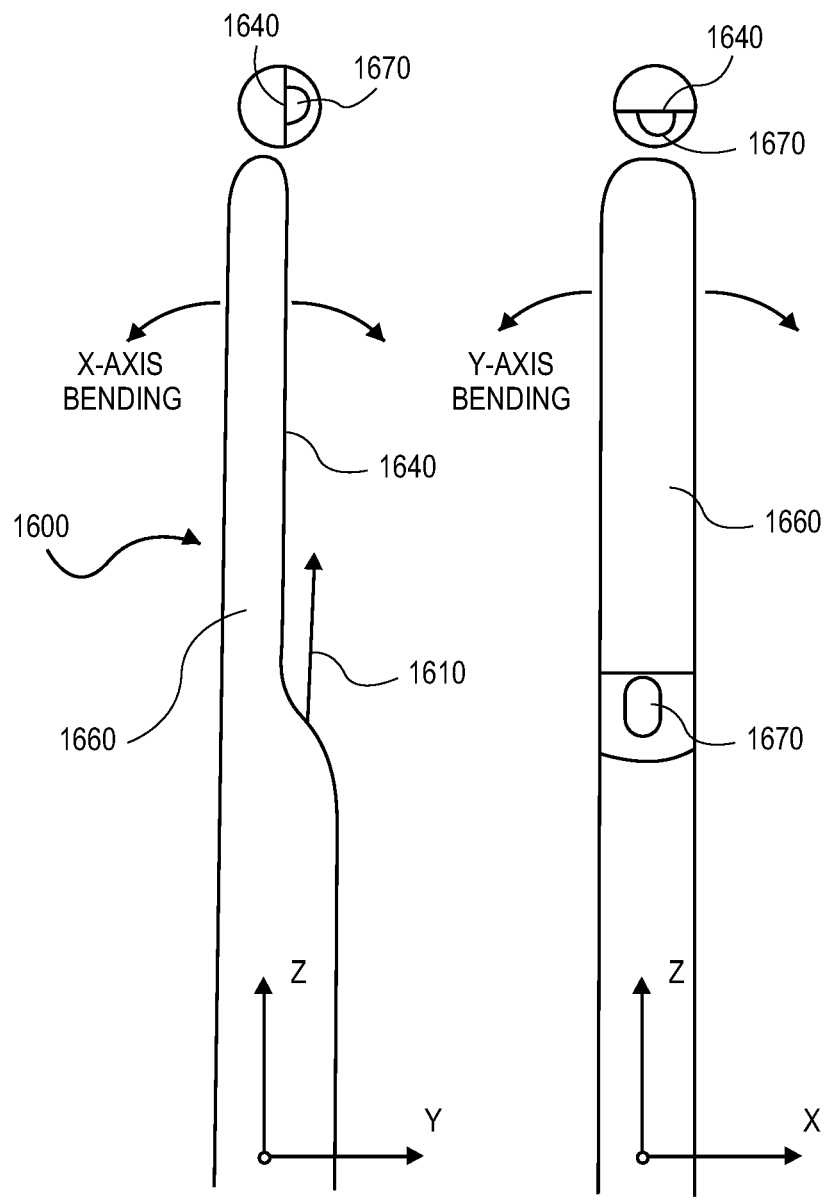
FIG. 16D illustrates the side and front and top views of a stiff conduit with offset, configured to prevent bending along two axis both perpendicular to the longitudinal access of the conduit, such that a tissue dissector can remain substantially parallel (e.g., within 15° or less) to a conformed vessel wall.

In some embodiments of the mechanisms depicted in FIG. 16D the distal portion 1660 of the stiff, flat surface 1640 of the support mechanism 1600 is sufficiently stiff to resist bending about the x and y axis (as depicted). This way, if the vessel in which the device is implanted takes a tortuous path, the distal portion 1660 resists bending along with the vessel, which allows advancement of a puncture element or tissue dissection probe to be ensured to maintain sufficiently parallel trajectory 1610 (along the z axis) and to maintain position within the center of the flat surface 1640 (not meandering off the side of the flat surface entirely along the positive or negative x axis). This can be done by using inherently stiff materials for the entire support mechanism 1600 or exclusively in the distal portion 1660 of the support mechanism. In some embodiments, the distal portion 166 that must have sufficient stiffness can be defined by the portion spanning at least 4 cm proximal to the exit port 1670 of the support mechanism, and spanning at least 4 cm distal the exit port 1670. In some embodiments, the distal portion 1660 that must have sufficient stiffness can be defined by the portion spanning at least 2 cm proximal to the exit port 1670 of the support mechanism, and spanning at least 2 cm distal the exit port 1670. In some embodiments, the distal portion 1660 that must have sufficient stiffness can be defined by the portion spanning at least 1.25 cm proximal to the exit port 1670 of the support mechanism, and spanning at least 1.25 cm distal the exit port 1670. In some embodiments sufficiently stiff is defined as less than 4 mm of deformation if a 0.5 lb force is applied along a 6 cm lever arm. In some embodiments sufficiently stiff is defined as resistance to 2 mm of deformation if a 0.5 lb force is applied along a 6 cm lever arm. In some embodiments sufficiently stiff is defined as resistance to 1 mm of deformation if a 0.5 lb force is applied along a 6 cm lever arm. In some embodiments sufficiently stiff is defined as resistance to 0.25 mm of deformation if a 0.5 lb force is applied along a 6 cm lever arm.

In some embodiments involving a stiff, flat distal portion of the support mechanism for accommodating the conformed vessel wall, and an expansion mechanism housed on the opposite side of the support mechanism (or tubular structure), the distal portion of the support mechanism, must be stiff enough to resist bending in about any axis (by more than 2 mm over a 6 cm lever arm) along the entire length of the expanded expansion mechanism while the mechanism is expanded. For example, if a balloon is expanded causing even a curved vessel to straighten out and causing the vessel wall to conform along the distal portion of the support mechanism, the distal portion must be stiff enough to resist bending as a result of the tensioned wall, for the entire axial length of the expanded balloon.

Figure 16G:
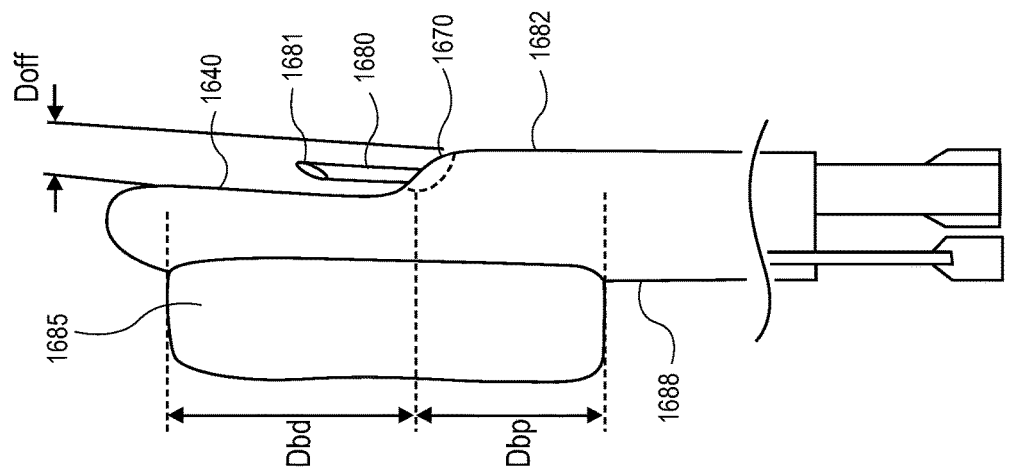
FIGS. 16E-16G illustrate the critical dimensions of puncture height, offset distance, and proximal balloon length and distal balloon length in a conduit configured with an expandable member, an advancable puncture element, and a dissection probe.
Figure 16F:
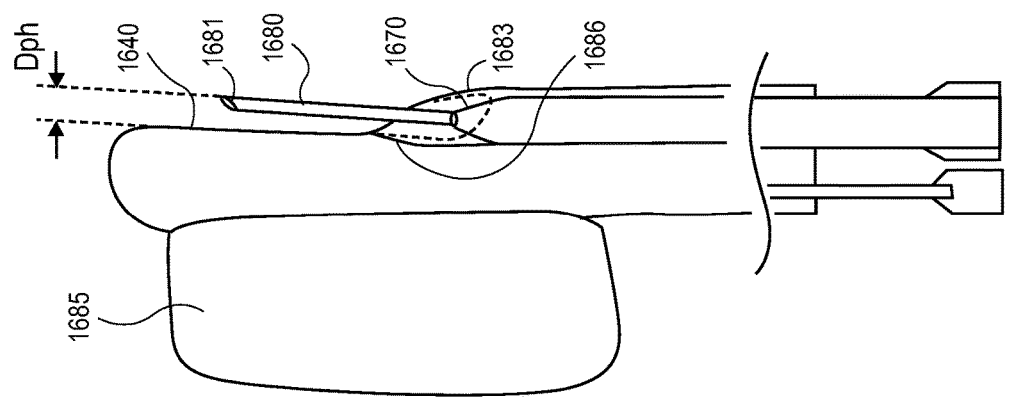
Figure 16E:
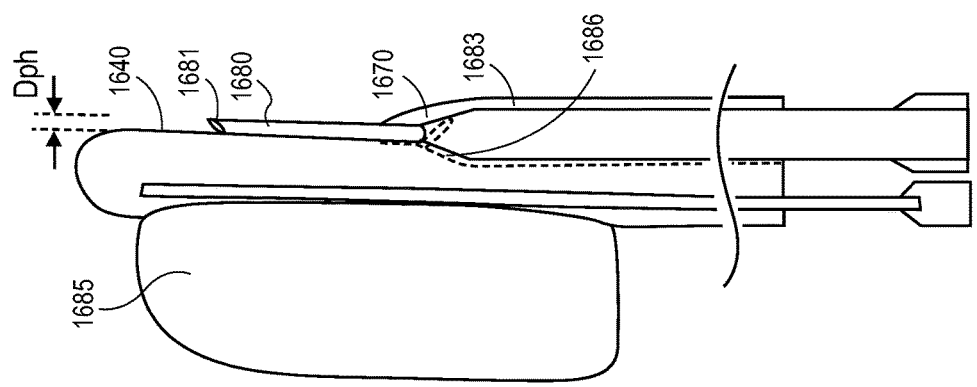

FIGS. 16E-16F depict the critical dimension of puncture element puncture height. The puncture height dictates how deep within the thickness of the vessel wall, the puncture element will enter and therefore, what plane the hydrodissection will create. In FIG. 16E, the puncture element 1680 exits the dissection probe in line with the flat support surface 1640 of the support structure. In this depiction, the puncture element can be advanced while sliding along the flat support surface 1640. In this embodiment, the diameter of the puncture element 1680 itself (if the bevel 1681 is oriented as shown), dictates the puncture element 1680 puncture height ($D_{ph}$). This embodiment represents the shallowest possible dissection plane within the vessel wall for a given puncture element 1680 diameter and at the depicted bevel 1681 orientation. In FIG. 16F, the mechanism is designed such that the puncture element or needle 1680 exits the dissection probe exit port 1670 parallel to the flat support surface of the support structure, but at a constant, non-zero height above the flat surface 1640. Dph should be chosen to be smaller than the vessel wall thickness, such that when the puncture element 1680 (or dissection probe), which itself has a diameter that is necessarily smaller than the vessel wall thickness, is advanced into the wall, it cannot puncture through the outer side (the adventitia) of the vessel wall. In some embodiments an ideal puncture element puncture height is between 0.010" and 0.100". In some embodiments an ideal puncture element puncture height is between 0.015" and 0.060". In some embodiments an ideal puncture element puncture height is between 0.020" and 0.040". In some embodiments an ideal puncture element puncture height is between 0.025" and 0.030". FIG. 16G depicts a few other critical dimensions. The dimension $D_{off}$ represents the distance between the flat support surface 1640 and the outermost edge 1682 of the support structure. Upon inflation of the expansion mechanism 1685 (here a balloon), the vessel wall will conform to the outermost edge 1682 of the support structure proximal to the exit port 1670, and will conform to the flat supporting surface 1640 distal to the exit port 1670. Thus, $D_{off}$ represents the amount of offset the two portions of vein wall will take. In some embodiments $D_{off}$ is between 0.005" and 0.060". In some embodiments $D_{off}$ is between 0.010" and 0.040". In some embodiments $D_{off}$ is between 0.016" and 0.030". In some embodiments the support structure isn't flat but has a concave curvature. In other embodiments the support structure isn't flat, but has a convex curvature. In both of these cases, the dimensions described here are in reference to the center-line of support surface, which will correspond to a minimum or maximum dimension. In all embodiments shown in FIG. 16, the dissection probe 1683, which may also be or contain functionality for pocket creation (balloon or snare), can be advanced over the puncture element 1682 and into the pocket after the puncture element has been sufficiently advanced. These embodiments depict an exit ramp 1686 and exit port 1670 that allow the probe 1683 to be advanced out of the tool lumen, while controlling the puncture element 1680 puncture height.

FIG. 16G also depicts two other critical dimensions, proximal balloon length ($D_{bp}$) and distal balloon length $D_{bd}$). In the embodiment shown, a semi-compliant balloon 1685 (sometimes another type of expanding element) is expanded from the back side of the support structure 1688, which works to create a straight section of apposition between the support structure surface 1640 and the vessel wall. $D_{bp}$ represents the distance the fully inflated balloon 1685 covers proximal to the exit port 1670, from which the puncture element 1680 or dissection probe 1683 emerges and punctures the vessel wall. $D_{bd}$ represents the distance the fully inflated balloon 1685 covers distal to the exit port 1670. In some embodiments, vessel wall puncture will occur distal to the port 1670 itself. In these embodiments, these distances will be measured from the puncture site. In some embodiments, $D_{bp}$ is chosen to be between 0 mm and 15 mm. In some embodiments, $D_{bp}$ is chosen to be between 2 mm and 10 mm. In some embodiments, $D_{bp}$ is chosen to be between 4 mm and 8 mm. In some embodiments, $D_{bd}$ is chosen to be between 2 mm and 40 mm. In some embodiments, $D_{bd}$ is chosen to be between 5 mm and 30 mm. In some embodiments, $D_{bd}$ is chosen to be between 10 mm and 20 mm.

FIG. 16H and FIG. 16I describe a method for controllably entering the vessel wall 1620 with a puncture element 1680. As described in a previous embodiment, the puncture height of the puncture element is determined by the geometry of the support structure 1640, the puncture element 1680 diameter, and the angle of the bevel 1681 of the puncture element 1680 (here a beveled needle) with the vessel wall 1620. In the following embodiment, the user has the ability (active or passive) to rotate the puncture element 1680 about its longitudinal access, thus changing the bevel 1681 angle with respect to the vessel wall 1620, and thus changing the puncture height. In this embodiment, FIG. 16H depicts the expansion mechanism 1685 (a balloon or cage) having just been expanded off the opposing side 1688 of the support structure, forcing the vessel wall into the flat surface of the support structure 1640, while the puncture element 1680 is already in a starting position outside the exit port 1670 of the support structure, and therefore in contact with the vessel wall. The beginning angular orientation of the puncture element 1680 and bevel 1681 is such that the puncture height is minimized for the given puncture element diameter and outlet height (0°). FIG. 16I depicts a method for gaining controlled entry into the vessel wall 1620 without traveling all the way through the wall, by simply rotating the puncture element 1680 toward 180°, or an angular orientation that maximizes the puncture height for the given puncture element 1680 diameter and outlet height. The distal sharp tip or bevel 1681 of the puncture element 1680 is in this way inserted into the vessel wall 1620 due to the counter-tensions provided by the expansion element 1685 on the support device. In a similar embodiment, this rotational entry method can be accomplished with slight forward advancement of the puncture element 1680 right after rotational bevel entry into the wall. In another similar embodiment, this rotational entry method can be accomplished with slight forward advancement of the puncture element 1680 during rotational bevel entry into the wall. Any of these methods can be employed by a mechanism that allows the user the ability to manually trigger rotational movement and translational movement (advancement) of the puncture element. In other embodiments, all of these methods can be employed by a mechanism that provides an automated combination of rotation and translation of the puncture element with a single trigger mechanism imparted by the user, such as a button, lever, or handle movement.

Methods and Mechanisms for Creating Controlled Pocket Geometries within a Vessel Wall (Pouch Formation Vs Inlet Widening)

Figure 20:
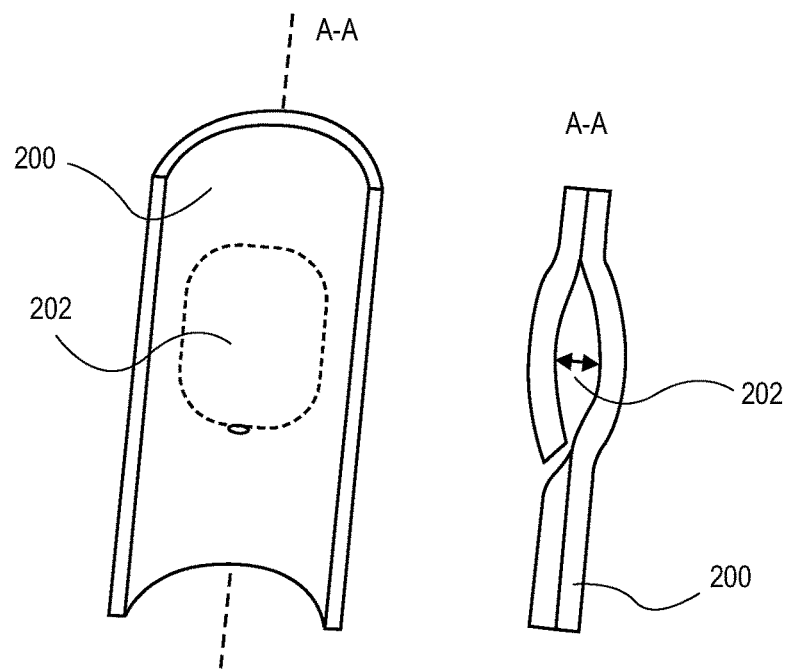
FIG. 20 illustrates front and side views of the geometries within a vessel wall associated with the definition of pouch formation.

In the following embodiments, a vascular valve flap creation is described, a process that can use two distinct methods. The first method will be referred to as pouch formation and can be carried out with a pouch formation mechanism. This method involves separating distinct tissue layers within a vessel wall 200 to create a specific geometry of potential space (a pouch) 202 between vessel layers with a pealing force (FIG. 20). The layers to be separated are as follows: the intimal tissue layer from the medial tissue layer, or the medial layer from the adventitial layer, or a fibrosis layer from the intimal layer, or a sub-medial layer from another sub-medial layer, or a sub-adventitial layer from another sub-adventitial layer. For a monocuspid valve, the length of tissue separation (pocket depth) should be between about 1× and 3× the diameter of the vessel, or between about 1.5× and 2.5× the diameter of the vessel, or between about 1.75× and 2.25× the diameter of the vessel. For bicuspid valves, the length of tissue separation (pocket depth) for each leaflet should be between about 0.75× and 2× the diameter of the vessel, or between about 1× and 1.5× the diameter of the vessel.

Figure 21:
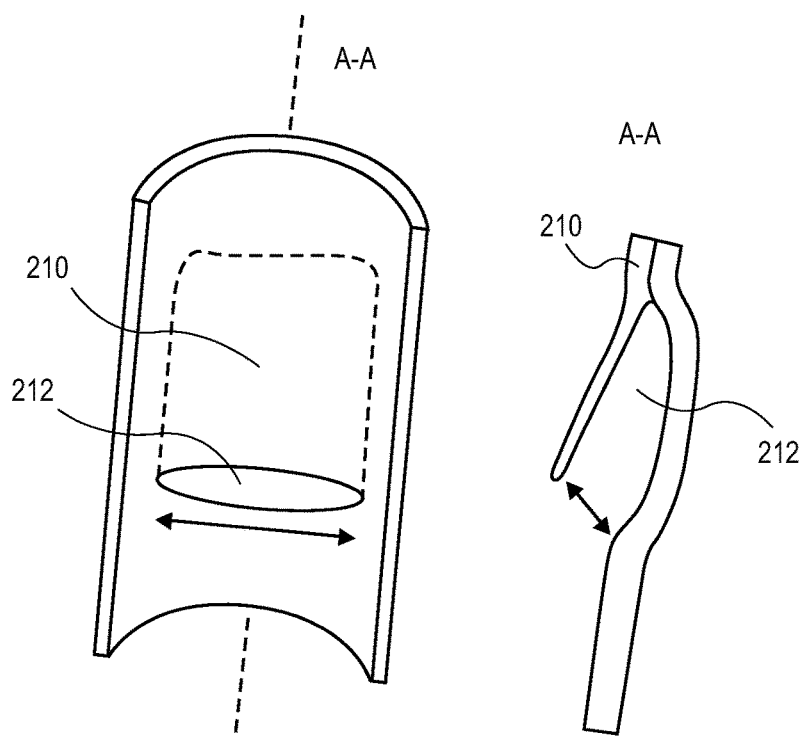
FIG. 21 illustrates front and side views of the geometries within a vessel wall associated with the definition of inlet widening.

The second method will be referred to as inlet widening and can be carried out with an inlet widener. This method involves widening a defect or hole 212 within the inner most inner two most vessel wall layer(s) 210 by either stretching the inner most layer(s) (as in child-birth) 210, tearing the inner most layer(s) 210, or a combination of tearing and stretching (FIG. 21).

In accordance with some embodiments, these two methods can be carried out with separate mechanisms or one single mechanism that can accomplish both methods.

In accordance with all embodiments for the formation of a pouch and a valve flap, the mechanisms described can be advanced from a side port at or near the exit of a support catheter (although they man not always be depicted as such for simplicity). All embodiments described for creation of these pouches and flaps, can be used in combination with other components described for full valve creation, including expansion mechanisms for wall control, and mouth opening balloons for full valve creation. An example of one way in which to combine embodiments to complete the valve creation procedure is depicted in FIGS. 29A-29F at the bottom of this disclosure. The embodiments depicted here can be used in combination with these or similar techniques to create a full valve geometry.

Methods and Mechanisms for Creating Controlled Pocket Geometries within a Vessel Wall (Pouch Formation with Hydrodissection)

In accordance with some embodiments of a controlled dissection assembly, the probe is advanced into the vessel wall to a specific depth. At this point, or during advancement, the probe begins to eject this high-pressure hydrodissection fluid from side ports as well as or instead of from its distal tip. In these embodiments, the fluid velocity and pressure can be controlled to form pockets with controlled depths (forward facing hydrodissection expulsions) and widths (expulsions from the side ports). Monocuspid pouch dimensions should be about 8-18 mm deep (for veins with diameter 8 mm-12 mm) and 140-280 degrees in width.

In accordance with some such embodiments, a device includes a dilating probe 170 with hollow lumen 172, which is in fluid communication with a source of high pressure hydoridssecting fluid at the proximal end. The dilating probe 170 has a number of sideways facing exit ports 174 near to but proximal to its distal most tip 176, which has a distal exit port 178, that are in fluid communication with the inner lumen 172 of the dilating probe.

In accordance with some embodiments, between one and eight side ports 174 are arranged to within the distal 1 cm-3 cm of the dilating probe 170.

Figure 17:
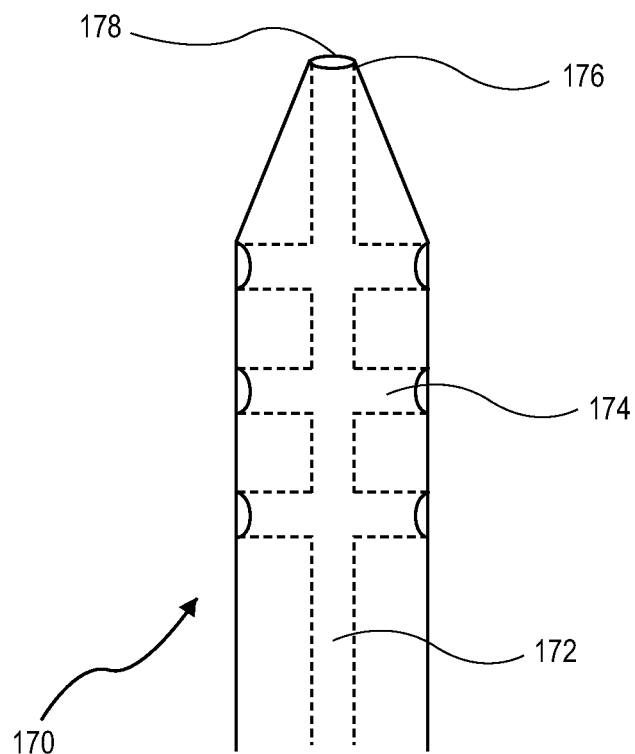
FIG. 17 illustrates a tissue dissection probe configured with multiple side ports and a distal port, used for creating specific intra-mural pocket geometries.

In accordance with some embodiments, the side exit ports 174 are arranged about 180 degrees from each other, with an equal number of holes on each side (FIG. 17).

In accordance with other embodiments, the side exit ports 174 are located evenly spaced around the entire circumference of the entire probe and along the hydrodissecting length.

Some embodiments have other arrangements of side ports 174 near the distal end 176 of the tapered dilating probe 170.

In accordance with some embodiments, a controlled dissection assembly 180 with distal exit port 182 and some number of sideways facing exit ports 184 can transform between two configurations. In one configuration (FIG. 18A), a hollow puncturing element 186 is contained within the lumen 188 of the dilating probe 180 and extends out of the distal end of the dilating probe. This configuration is used to puncture the wall of a vessel while (or before) a hydrodissecting fluid is ejected through the lumen of the puncturing element 186 and therefore out the distal tip of the dilating probe 180 (and not out of the side exit ports). After this configuration is advanced within the vessel wall to a sufficient depth of pocket, with the assistance of hydrodissection, the puncturing element 186 is removed and a second configuration is initiated (FIG. 18B). In this configuration, a flow-directing element 183a is inserted into the lumen 188 of the dilating probe 180. The flow-directing element 183a is comprised of a stiff solid rod 185a with a solid ball or cylinder 187a at its distal end with diameter larger than that of the solid rod itself. The solid ball or cylinder 187a is sized so that it can be pushed through the lumen 188 of the dilator but occludes the narrower portion of the dilator lumen 188 when pushed to the distal opening of the dilator. The back end of this configuration is made so that the hydrodissecting fluid can be forced through the lumen 188 of the dilating probe 180, around the solid rod 185a of the flow-directing element 183a with use of hemostasis valves to maintain pressure. In doing this, the fluid is forced out of the side ports 184 and a circumferential hydrodissection can be accomplished once the dilator has been advanced some distance into the vessel wall.

In a similar embodiment, for configuration 2 (FIG. 18C), the flow-directing element 183b described is comprised of a thin walled hollow tube 185b with a closed distal end 187b and side ports 189b some distance from the distal tip of the dilating probe 180. In this embodiment, the hydrodissecting fluid is infused through the lumen 181 of the flow-directing element 183b, so that it exits the side ports 189b of the flow directing element 183b and the side ports 184 of the dilating probe 180.

In other embodiments, a flow-directing element is used that does not require full removal of the puncture element.

In one such embodiment, the distal end of the dissecting probe has housed within it a self-closing hydrostatic seal (made of silicon or another similar material). In this way, when the puncture element is retracted (but not fully removed), the distal end of the dissecting probe is hydrostatically sealed, and flow through the lumen of the dissecting probe is forced through the side ports.

In another such embodiment, in which the puncture element itself has side ports. A stylet is forced into the lumen of the puncture element to both block flow through its distal tip, and create a bluntness at the distal end. This stylet may have a silicon tip at the end of a narrow push rod, so that fluid may still flow around the push rod, but within the lumen of the puncture element. The fluid can then exit the side ports of the puncture element and the probe.

In a similar embodiment, no flow directing probe is used, but rather the puncturing element is removed and hydrodissection is administered through the dilating probe itself so that fluid is expelled both through the distal tip of the dilating probe and through its side ports.

In one such embodiment, the full vessel valve geometry is created with a controlled hydrodissection. In some embodiments, this is accomplished with the aid of an inlet sealing mechanism (previously described) on the tissue dissection mechanism. From this proximal location, the correct depth and width can be created with a series of pressurized bursts, that continue until a sufficient depth and width has been created. Depth and width may be determined/monitored in real time with one or more of the following:
 i. Contrast fluoroscopy
 ii. External Ultrasound
 iii. Intravascular Ultrasound
 iv. Direct Visualization within the lumen
 v. Pressure Sensing. This would be accomplished by monitoring the pressure in the pouch, which is in closed fluid communication with the internal lumen of the tissue dissector. Because a specific volume of pocket corresponds to a specific pressure in the system for a given input, the system can determine pouch volume from a pressure sensor on the device.

Methods and Mechanisms for Creating Controlled Pocket Geometries within a Vessel Wall (Administration of Hydrodissection)

Figure 53:
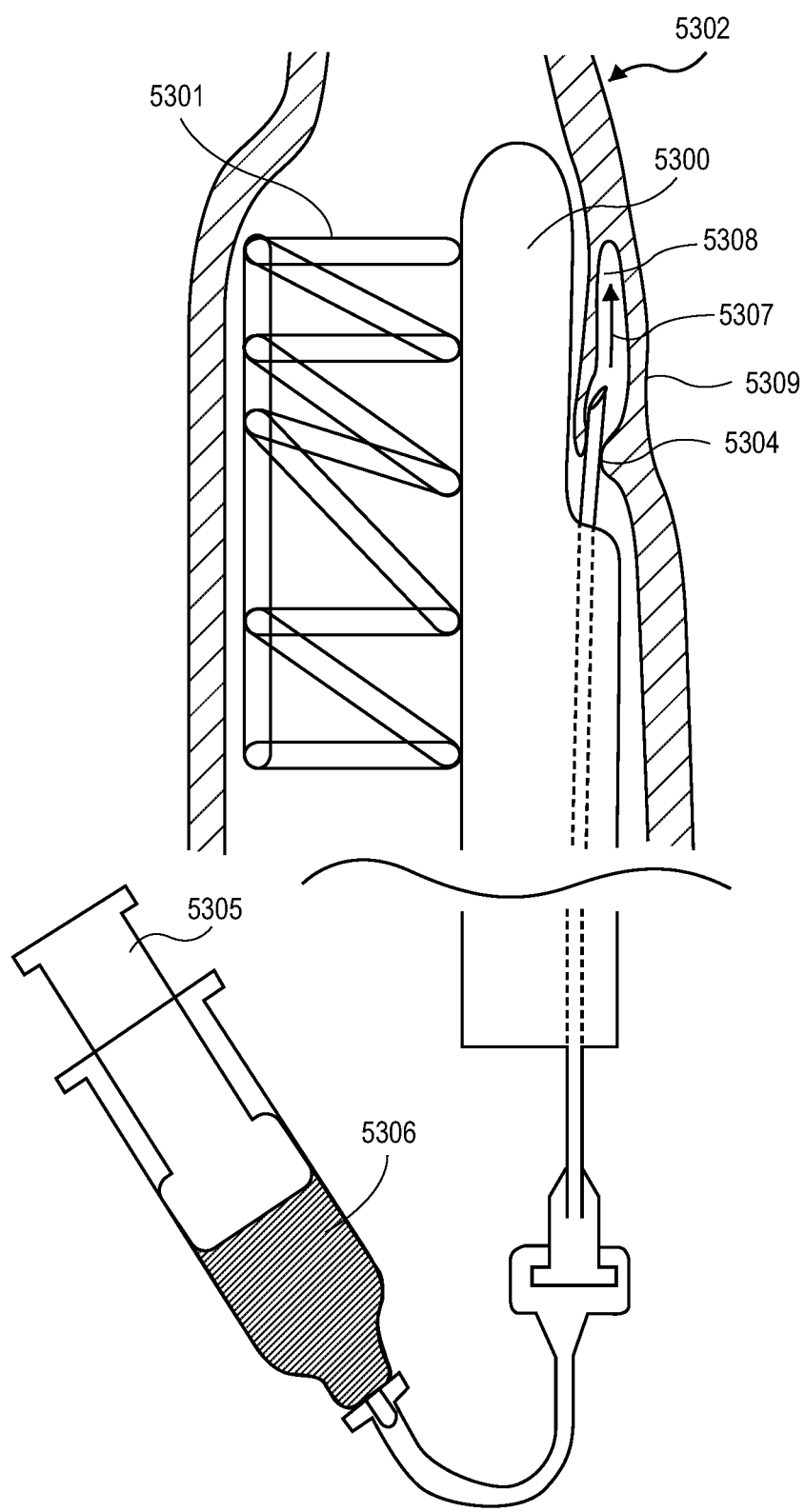
FIG. 53 illustrates an embodiment of a support structure that utilizes an expanding metal cage for wall apposition, and executes a hydrodissection to gain intra-mural access with a puncture element fluidly connected to a syringe.

In accordance with some embodiments, FIG. 53 depicts a tubular support system 5300 comprising an expansion mechanism (here a cage) 5301, expanded within a vessel 5302. Extending out of a port on one side of the tubular support system is a tissue dissection probe 5304, (depicted here as a needle), which is connected fluidly with a mechanism for providing a pressure differential 5305 (here a syringe plunger), which itself is fluidly connected to a fluid reservoir 5306 (here a syringe barrel). When activated, the mechanism forces fluid 5307 into, through, and out of the tissue dissecting probe 5304 so that it can act to separate an inner tissue layer 5308 from an outer tissue layer 5309.

In some embodiments, a powered pump (peristaltic, centrifugal, constant volume, etc.) attached to a reservoir of hydrodissection fluid is used. In another embodiment, a standard hand syringe is used with relatively small diameter piston. In another embodiment, a modified hand syringe with small stroke diameter but long shaft is used. In some embodiments, the design takes advantage of a lever to gain a mechanical advantage to provide sufficient pressure. An example of this is depicted in FIG. 19, in which a handle 190 is connected rigidly to a lever 191, which is connected to a hinged piston 192. This piston slides with a fluid-tight fit within a syringe chamber 193. The syringe chamber 193 is fluidly connected to a fluid reservoir 194. The lever 191 is also connected to a finger grip 195 by a hinged connection 196, so that the handle 190 has freedom to move forward as shown, to force fluid into the tissue dissection probe. Other similar embodiments may also take advantage of some sort of pistol grip arrangement, used to increase the efficiency of force transfer between the hand and the piston due to ergonomic considerations. In another embodiment, a hand squeeze-ball hand pump configuration is used (analogous to inflating a blood pressure cuff). In another embodiment, a foot powered pump is used so that the user can impart a large percentage of his/her weight onto the angled pump to push the fluid.

In many such embodiments an auto-refill function is to be used, such that after inputting a force to expel the hydrodissective fluid, the mechanism automatically re-loads into its primed position, and in the process pulls a new quantity of hydrodissection fluid into the chamber to be expelled upon the next activation force. This function can be implemented with a spring-loaded piston attached to two exit ports, each with a one-way valve oriented in opposite directions. The inward one-way valve connects to a reservoir, the outward one way valve connects to the tissue dissection probe lumen.

Pressures used for tissue dissection in living vessel wall tissue should be between about 25 psi and 800 psi depending on the devices used. Most specifically, the pressure used should be chosen to control for an appropriate flow rate and fluid velocity at the nozzle of the dissecting agent, based on the geometry of the device and internal resistance. Pressure/velocity/flow rate combinations should be chosen so as to limit fluid velocity, as fluid velocity above a certain threshold may cause perforations in the tissue. In some embodiments an appropriate fluid velocity is between 0.25 m/s and 4.0 m/s. In some embodiments an appropriate fluid velocity is between 0.5 m/s and 2.0 m/s. In some embodiments an appropriate fluid velocity is between 0.75 m/s and 1.25 m/s. Additionally, pressure/velocity/flow rate combinations should be chose to insure proper flow rate so as to maintain the internal pressure in the pocket required to dissect apart tissue layers with a given leak rate (from around the probe at the pocket inlet). In some embodiments, a typical hydrodissection flow is between 0.25 cc/second and 3 cc/second. In other embodiments, a typical hydrodissection flow is between 0.5 cc/second and 2 cc/second. In other embodiments, a typical hydrodissection flow is between 0.75 cc/second and 1.25 cc/second.

FIGS. 54A-E depict a method for implanting a puncture element 5400 into a specific intra-mural space 5401 and advancing it within the space along a specified length for the purpose of maintaining a fluid sealed pocket. This intra-mural space 5401 may be characterized by a layer between the intima and the media or between the media and the adventitia or in a sub-medial space, but is defined by an inner tissue layer 5402 and an outer tissue layer 5403. The method includes a specific dynamic interaction between hydrodissecting fluid ejections 5404 from the puncture element 5400 and timed advancements of the puncture element 5400. In this embodiment, the puncture element 5400 is advanced from within a supporting structure 5405 to control the angle and puncture height along with the tautness and straightness of the vessel wall 5406. FIG. 54A depicts advancement of the puncture element 5400 into the vessel wall 5406 at a particular puncture height, as characterized by one of the previously described methods and mechanisms. FIG. 54B depicts the puncture element 5400 just after the entire orifice of the bevel lumen 5407 has entered the vessel wall. At this point, the puncture element 5400 advancement is halted, and with activation by the user near the back end, fluid 5404 with sufficient flow rate/pressure is ejected from the bevel orifice 5407, creating a dissection of tissue layers distal to the puncture element bevel 5407. FIG. 54C depicts the subsequent advancement of the puncture element 5400 while fluid 5404 continues to eject. FIG. 54D depicts the halting of the puncture element 5400 advancement, as the fluid 5404 source is re-loaded. FIG. 54E depicts the continued advancement of the puncture element 5400 just after fluid ejection 5404 is re-initiated. This is continued until the puncture element 5400 has been advanced to a sufficient depth of pocket for valve creation. The underlying strategy employed by this method is always maintaining a forward fluid ejection during puncture element advancement. In another similar embodiment (not depicted), the puncture element is intermittently retracted a small amount during fluid ejection, which may aid in reducing resistance to flow associated with tissue being clogged in the needle bevel. Another embodiment involves a fluid source that never needs reloading, and can maintain a forward jet of fluid at all times during advancement.

Methods and Mechanisms for Creating Controlled Pocket Geometries within a Vessel Wall (Other Methods of Pouch Formation)

In accordance with some embodiments, a tissue dissection probe 220 is introduced into a vessel wall 222 some distance, but not entirely through the adventitia of the vessel (as described in previous embodiments). The probe 220 is then advanced within the vessel wall 222 distally (distal may be closer or farther from the heart depending on the direction of insertion), with the assistance of hydrodissection or manual blunt dissection. Once the tissue dissection mechanism 220 has been advanced to a sufficient depth, a pouch formation mechanism 224 is actuated to expand and create a pouch of known geometry.

In some embodiments of this kind, the tissue dissection mechanism 220 comprises on its exterior a pouch formation mechanism 224. This mechanism 224 is an expandable member 226 with sufficient force to separate tissue layers.

Figure 22A:
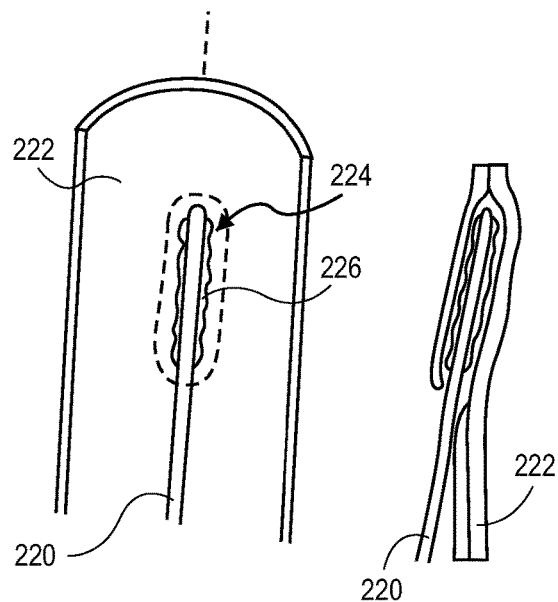
FIGS. 22A-22B illustrate front and side cross-sectional views of a conduit with balloon configured to create a pouch within a vessel wall, before and after pouch formation.
Figure 22B:
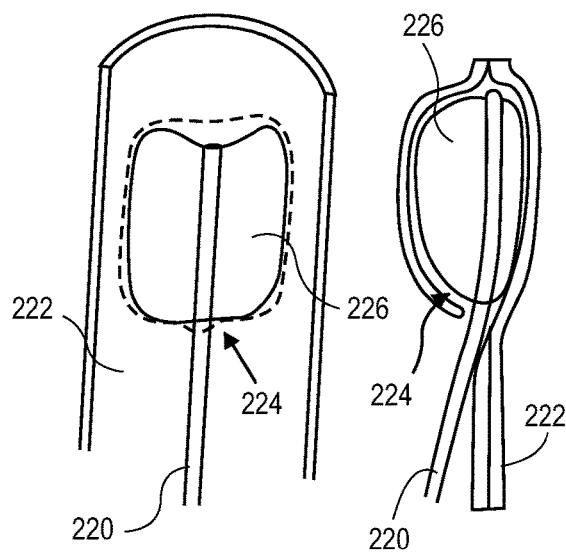

In some such embodiments this expandable member 226 is a complaint balloon made of latex or another compliant material (FIGS. 22A-22B).

In some such embodiments this expandable member 226 is a semi-complaint balloon made of silicone or rubber or polyurethane or another semi-compliant material. In some such embodiments this expandable member 226 is a non-complaint balloon made of a thermoplastic, PET, or another non-compliant material.

In some such embodiments this expandable member 226 is a made from a metal cage of sorts made of stainless steel or shape memory materials such as Nitinol.

Figure 23:
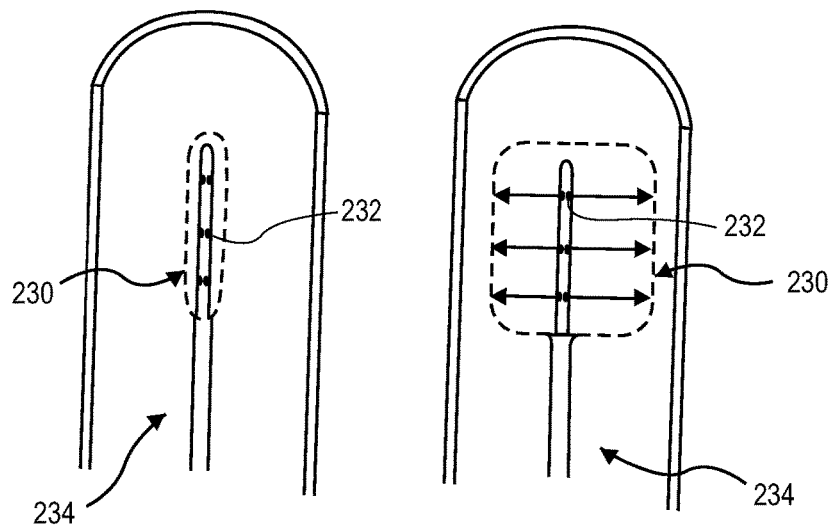
FIG. 23 illustrates front and side cross-sectional views of a conduit configured to create a pouch within a vessel wall with hydrodissection, before and after pouch formation.

In other embodiments of this kind, the pouch formation mechanism 230 is a controlled hydrodissection itself. This can be accomplished, as previously described with some arrangement of exit ports 232 on the tissue dissection mechanism 234 and optionally a mechanism to control fluid pressure and flow direction (FIG. 23).

Figure 24A:
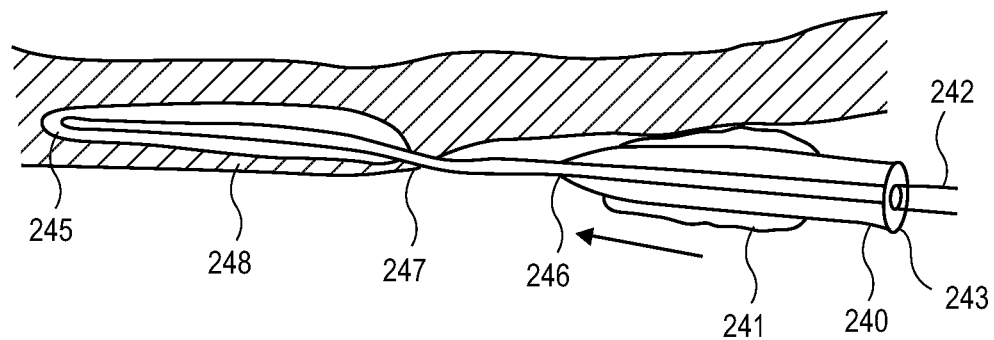
FIG. 24A illustrates a pouch formation balloon which is slidibly disposed over a puncture element (configured for tissue dissection) to be advanced through the vessel wall inlet and into an intra-mural space.

In other embodiments of this kind, the pouch formation mechanism 240 (similar to the embodiments previously described), depicted with expansion member 241 is introduced over the tissue dissection mechanism 242 via an internal lumen 243, and is advanced until it exists at a proper depth within the intra-mural pouch 245. In some of these embodiments, the tissue dissection mechanism over which the pouch formation mechanism is introduced, has a sharp distal tip and is considered a puncture element as well. A feather tapered tip 246 at the distal end of the pouch formation mechanism 240 is implemented to assist the device in entering through the hole 247 in the intimal wall 248 (FIG. 24A). In the embodiment depicted, the rest of the tubular support structure (not depicted) is removed prior to advancement of the valve creation mechanism over the puncture element. This is done by implementing a removable luer on the back-end of the tissue dissection mechanism 242, so that the entire device can be removed while the tissue dissection mechanism 242 remains embedded in the intra-mural pouch 245.

Figure 24B:
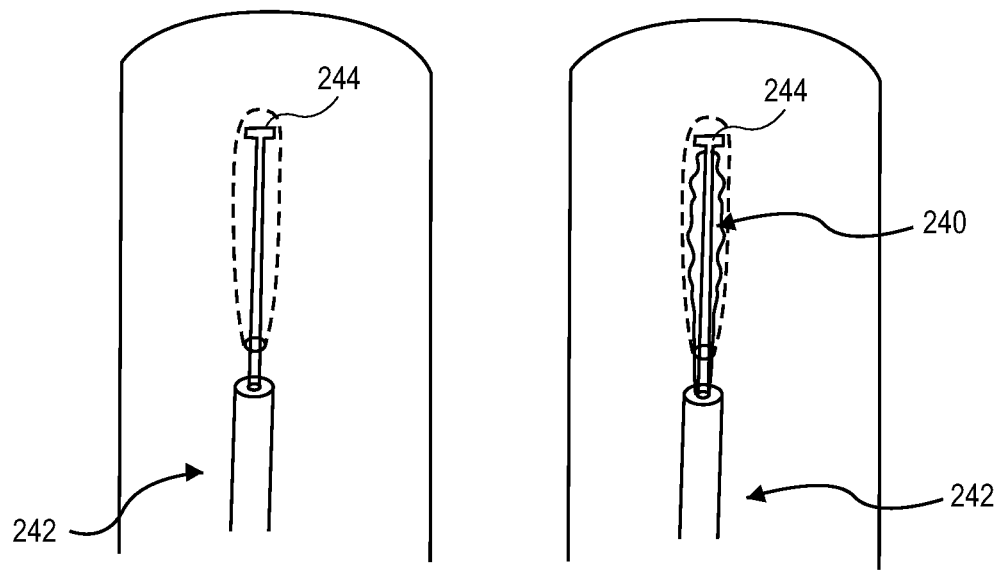
FIG. 24B illustrates a pouch formation balloon which is slidibly disposed over a tissue dissection element configured with a distal stopper, before and after advancement.

In a similar embodiment, a stopping mechanism 244, which is located at the distal end of the tissue dissection mechanism 242, is present to prevent this pouch formation mechanism 240 from advancing significantly past the tissue dissection mechanism 242, which could cause damage (FIG. 24B).

In other embodiments of this kind, the tissue dissection mechanism has within it a hollow lumen through which a pouch formation mechanism (similar to the embodiments previously described) can be advanced. In these embodiments, a stopping mechanism is present to prevent this pouch formation mechanism from advancing significantly past the tissue dissection mechanism, which could cause damage. Once at the correct depth, the tissue dissection mechanism can be retracted a small amount, such that the pouch formation mechanism can expand to execute pouch formation.

In other embodiments of this kind, the tissue dissection mechanism has within it a hollow lumen through which a guidewire can be advanced into the pocket. The tissue dissection can then be removed, leaving the guidewire behind. The pouch formation mechanism (similar to the embodiments previously described but including an internal through lumen for over-the-wire capabilities) can be advanced over-the-guidewire. In these embodiments, a stopping mechanism is present to prevent the guidewire from being advanced past the tissue dissection mechanism (until the tissue dissection mechanism is retracted) and to prevent the pouch formation mechanism from being advanced past the distal end of the guidewire, as this could cause damage.

In accordance with some other methods already described, a tissue dissection probe is introduced into a vessel wall some distance, but not entirely through the adventitia of the vessel. In these embodiments, the probe is not advanced within the wall to the appropriate depth needed for pouch formation. Instead, a pouch formation mechanism is deployed from this proximal location.

Methods and Mechanisms for Creating Controlled Pocket Geometries within a Vessel Wall (Inlet Widening)

In order to create a working monocuspid valve, the inlet to the wall defect can be widened to about 180 degrees or more. In order to accomplish this task with an expansion mechanism, the inlet can be stretched to between about 1.0× and 2.0× the diameter of the vessel, or between about 1.2× and 1.8× the diameter of the vessel, or between about 1.3× and 1.5× the diameter of the vessel. If a bicuspid valve is desired, the inlet can be widened to just under 180 degrees. In order to accomplish this, the inlet can be stretched to between about 0.5× and 1.5× the diameter of the vessel, or between about 0.75× and 1.25× the diameter of the vessel, or between about 0.9× and 1.1× the diameter of the vessel.

Figure 25:
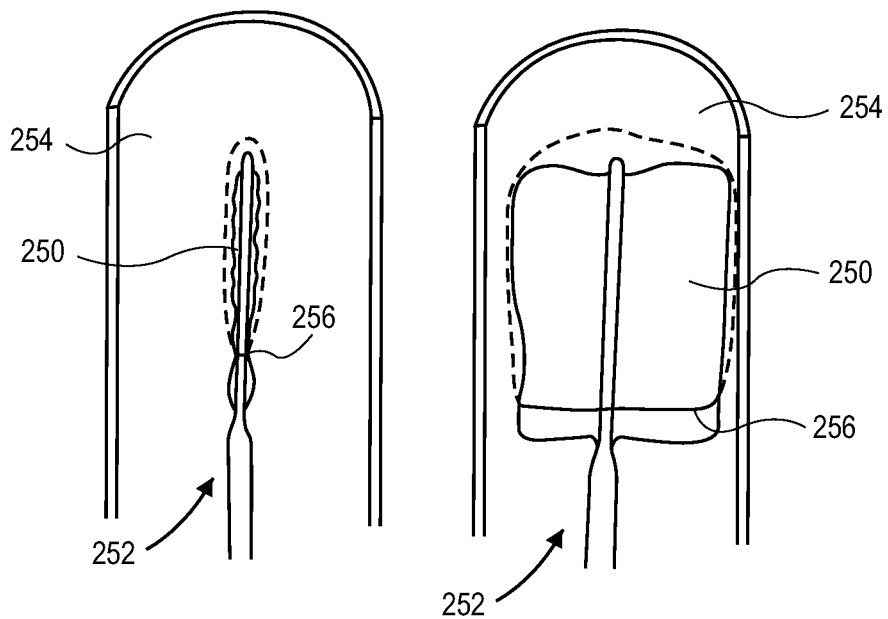
FIG. 25 illustrates a conduit configured with a expandable balloon which is disposed within a narrow intra-mural plane at first, and is then expanded to create a intra-mural pouch and to widen the inlet to form a valve mouth, simultaneously.

In accordance with some embodiments, the inlet widening mechanism is one and the same as the pouch formation mechanism, and both methods are accomplished simultaneously. To give one of many examples, a non-compliant expandable balloon 250 may be present on the tissue dissection device 252, which is advanced distally within a vessel wall 254 to a sufficient depth for valve creation. The balloon 250 is expanded to a shape that creates an appropriate valve sinus and opens the inlet 256 of the valve to an appropriate width simultaneously (FIG. 25). All previously described pouch formation mechanisms therefore may apply to the inlet widening mechanism as well. In a similar embodiment, this expansion mechanism may be comprised of a semi-compliant or a complaint balloon. In this description, a non-compliant balloon is known as a balloon that expands less than an additional 2 mm when increased from 60% of its max rated pressure, to 100% of its max rated pressure. A semi-compliant balloon is known as a balloon that expands between an additional 2 mm and an additional 8 mm when increased from 60% of its max rated pressure, to 100% of its max rated pressure. A compliant balloon is known as a balloon that expands more than an additional 8 mm when increased from 60% of its max rated pressure, to 100% of its max rated pressure.

Figure 26:
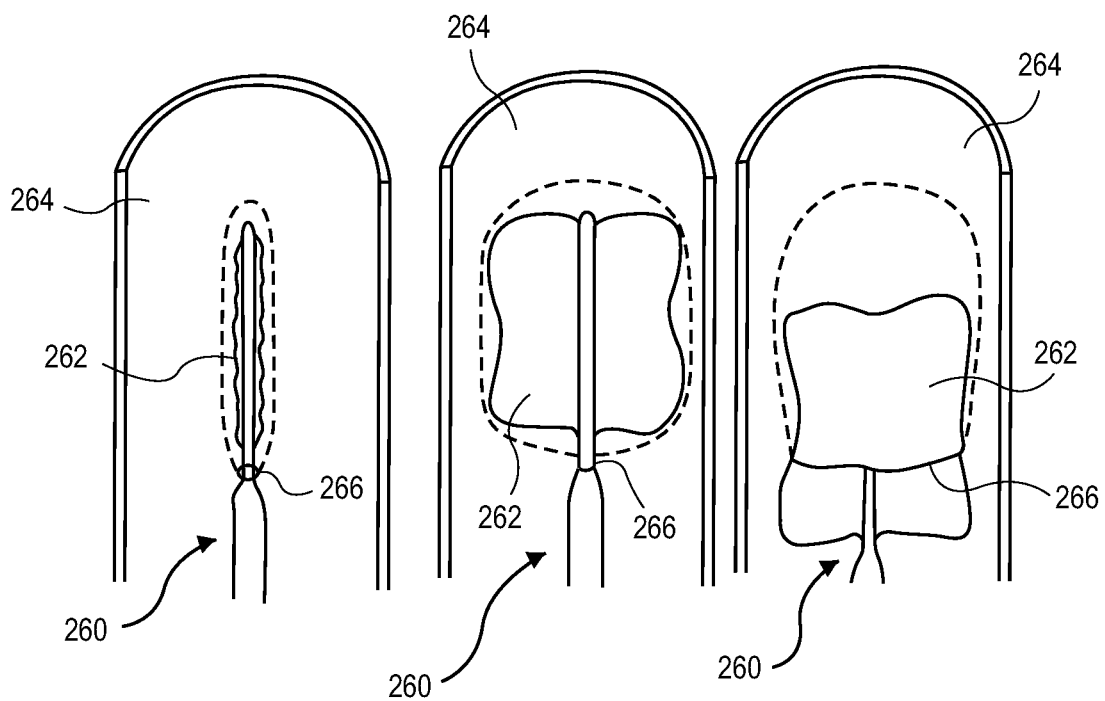
FIG. 26 illustrates the use of a balloon with a self-centering mechanism which is used within an intra-mural plane to create a pouch, and is then later used with a self-centering method to widen the inlet to form a valve mouth.

In accordance with some embodiments, the inlet widening mechanism is one and the same as the pouch formation mechanism, but both methods are accomplished at different times. To give one of many examples, a non-compliant expandable balloon 260 may be present on the tissue dissection device 262, which is advanced distally within a vessel wall 264 to a sufficient depth for valve creation. The balloon 260 has a length shorter than that of the pocket depth, and therefore is expanded to a shape that creates an appropriate valve sinus but does not open the valve sinus. The balloon 260 is then deflated, retracted slightly, and then re-inflated to widen the inlet 266 to the now fully created pouch. In the embodiment shown, the expandable balloon 260 has a self-centering mechanism due to its bowed in shape, which helps the balloon in the inlet widening phase of the procedure (FIG. 26). In a similar embodiment, this expansion mechanism may be comprised of a semi-compliant or a complaint balloon.

In accordance with some embodiments, the inlet widening mechanism is distinct from the pouch formation mechanism.

In one such embodiment, a cylindrical non-complaint expansion mechanism or balloon is present some distance proximal from the distal end (5-15 mm) of the tissue dissection mechanism. This is used to open the inlet. In one particular embodiment, this inlet widening mechanism is paired with a compliant expansion mechanism or balloon, which is located more distally on the tissue separating mechanism.

In another such embodiment similar to the one just described, the non-complaint balloon housed on the tissue dissection mechanism has a bowed in shape in the middle, to insure that the balloon remains fixed about the inlet as it inflates.

Figure 27A:
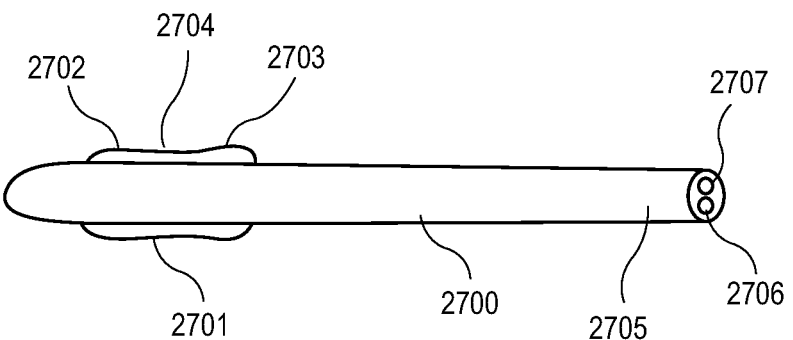
FIGS. 27A-27E illustrate a method for reliably widening an inlet in a vessel wall with side views in cross-section. The method utilizes a conduit with double inflating balloon with saddle geometry.
Figure 27B:
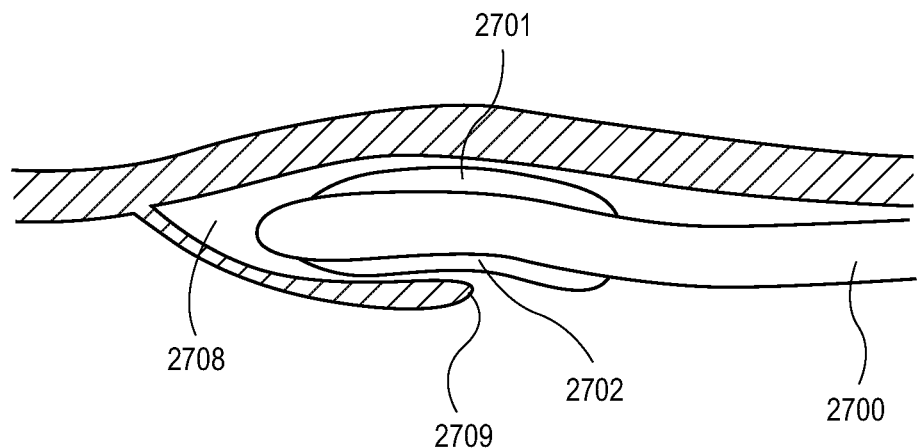
Figure 27C:
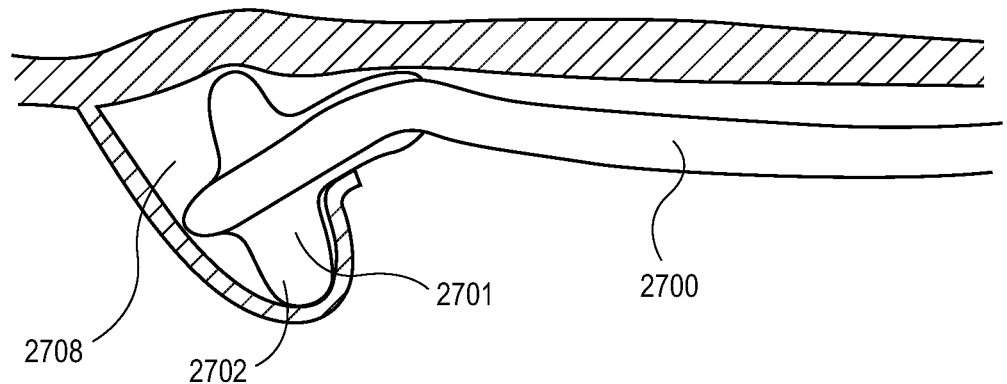
Figure 27D:
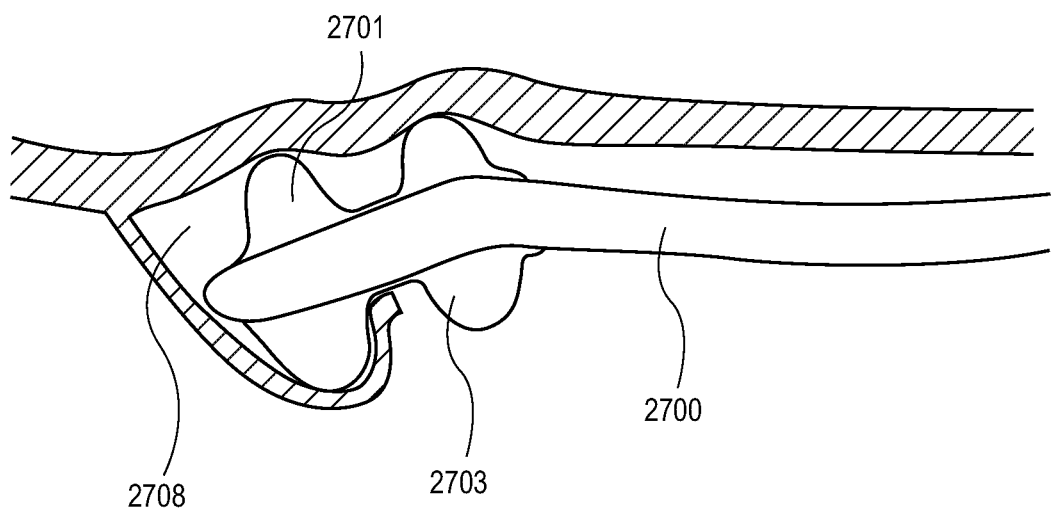
Figure 27E:
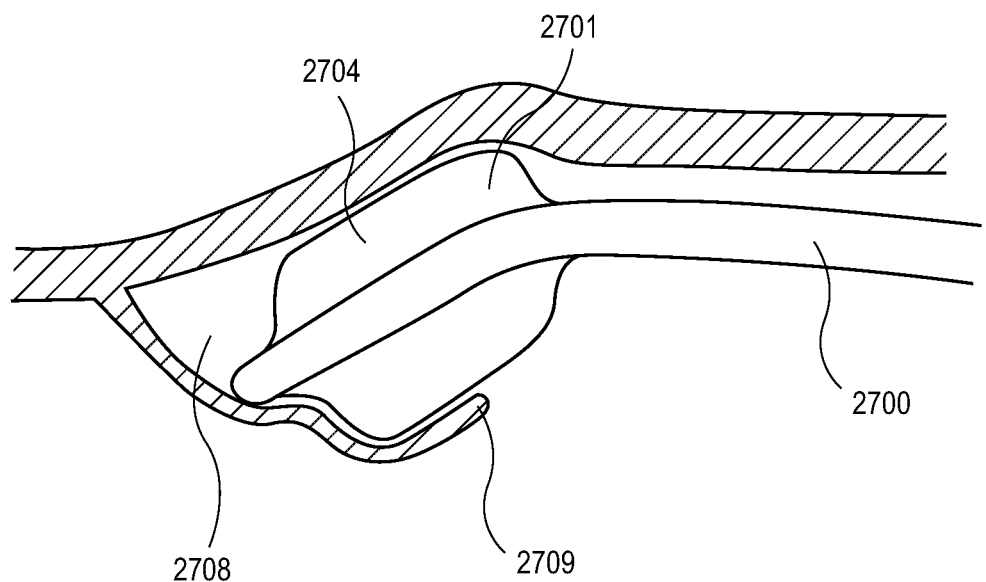

FIG. 27A depicts an embodiment of the inlet widening mechanism 2700 with a non-compliant or semi-compliant deflated balloon 2701, that inflates in a distinct sequence beginning with the distal end 2702, followed by the proximal end 2703, and followed by the middle section 2704. The balloon is bonded to the distal end of a tubular structure 2705 that has an inflation lumen 2706 through-lumen 2707 for injecting radio opaque contrast solution (not depicted). One of the previously disclosed techniques is employed to insert and advance the valve creation mechanism 2700 into the intramural space 2708 until the middle section 2704 of the balloon 2701 is aligned with intimal inlet 2709 leading to the intramural space 2708 (as shown in FIG. 27B). All structures used for the insertion are then retracted from the intramural space and from the balloon. The balloon 2701 is then pressurized through the inflation lumen 2706. The distal end 2702 of the balloon 2701 is inflated first, anchoring the valve creation mechanism 2700 in the intramural space 2708 (as shown in FIG. 27C). This action may be utilized to force the separation of tissue layers, enlarging the intramural space 2708, or is carried out after the intramural pocket 2708 is already fully created by a separate pouch formation mechanism. The proximal end 2703 of the balloon 2701 is inflated next, fully constraining axial translation of the balloon 2701 (as shown in FIG. 27D). The middle section 2704 is inflated last, and this action opens up the intimal hole 2709 at the top of the intramural space 2708 (as shown in FIG. 27E).

In another similar embodiment, the distal anchoring mechanism may be accomplished with an expanding metal cage, and the mouth is then widened with a more proximal noncompliant balloon.

Figure 32A:
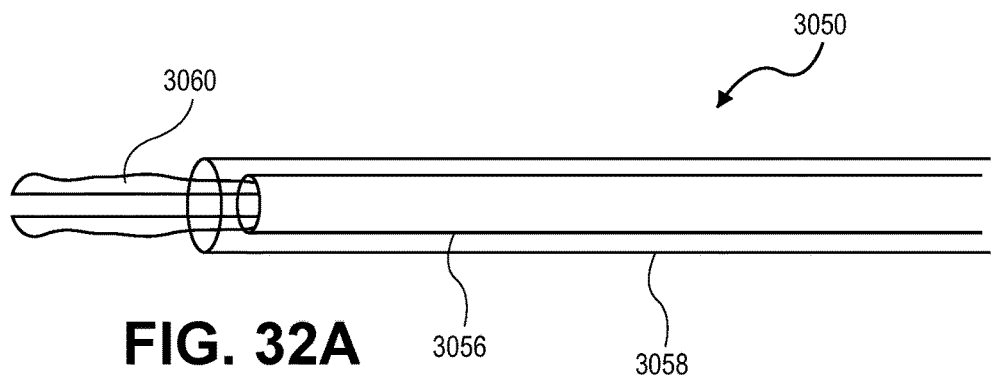
FIGS. 32A-32C illustrate a device for manipulating tissue at a vessel.
Figure 32B:
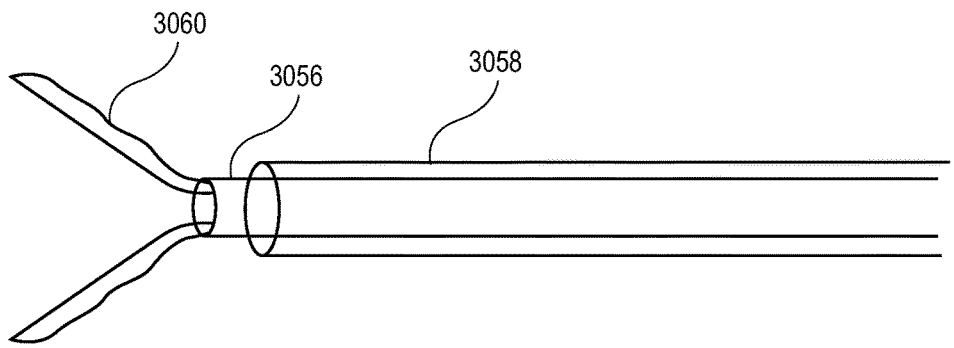
Figure 32C:
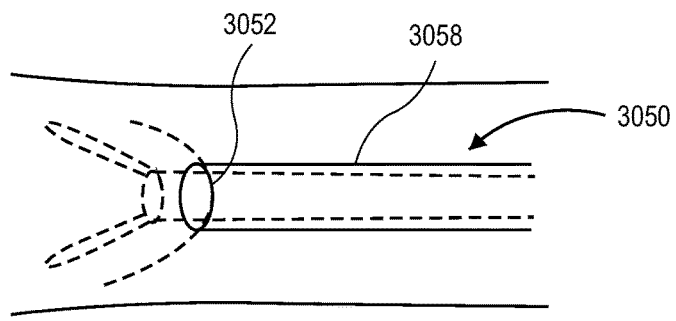

In accordance with some embodiments as illustrated in FIGS. 32A-32C, a device 3050 for manipulating tissue at a vessel is described, which has the ability to transition the inlet 3054 of a newly created autologous pocket 3052 from a narrow hole to a wide mouth (see FIGS. 20 and 21 respectively). A wide mouth at the top of a tissue pocket 3052 insures sufficient blood is able to enter and exit the tissue pocket 3052, which will benefit the pocket's ability to serve as a one way valve. In some embodiments, such a device 3050 includes two hollow, tubular members 3056, 3058. The inner member 3056 is made of Nitinol or another material that has the ability to be shape set. The inner tube 3056 is manufactured with one, two, or more sharpened tabs 3060 at the distal end, constructed out of the tube wall itself, which have been shape set to extend outward at an angle non parallel to the axis of the tube 3056 itself. The outer tube 3058, which can be constructed from stainless steel, plastic or another hard material, is sized to slide over the inner tube 3056 as a sheath. In one orientation, depicted in FIG. 32A, the tabs 3060 of the inner tube 3056 are constrained by the outer tube 3058 such that they rest close to parallel with the axis of both tubes. In another orientation, depicted in FIG. 32B when the outer tube 3058 is retracted or the inner tube 3056 is advanced, the tabs 3060 are free to extend outward until they contact tissue or until they reach their natural outward orientation.

In accordance with some embodiments, this cutting device 3050 is fed through the tool lumen 3004 of the conduit 3002 and into the narrow inlet of the tissue pocket 3052 following hydrodissection. Upon extending through the narrow mouth, the sharpened tabs 3060 are actuated as described above and the cutting device 3050 is retracted. Upon leaving the narrow inlet, the sharpened tabs 3060 impart an outward force on the bodily tissue and act to cut the narrow inlet open to a wider orientation.

In accordance with some embodiments, this cutting device 3050 is fed over the shaft of the pocket creation balloon and into the inlet of the tissue pocket 3052 so that it may be actuated in the same way as previously described.

In accordance with some embodiments, as depicted in FIG. 32C, this cutting device 3050 is fed over the shaft of the tissue engagement mechanism or hydrodissecting probe and into the inlet of the tissue pocket 3052 so that it may be actuated in the same way as previously described.

In accordance with some embodiments, the sharpened tabs 3060 are twisted about their own axis so that they can present the tissue with a thinner and therefore sharper geometry.

In accordance with some embodiments, the tabs 3060 have a curved orientation so that they may form a specific geometry of the inlet mouth.

Figure 33:
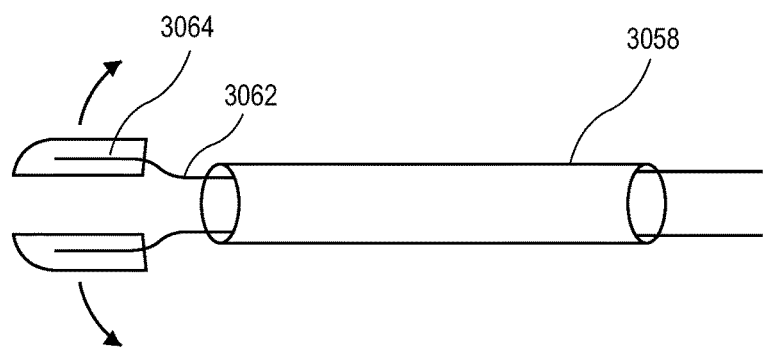
FIG. 33 illustrates a cutting mechanism.
Figure 34A:
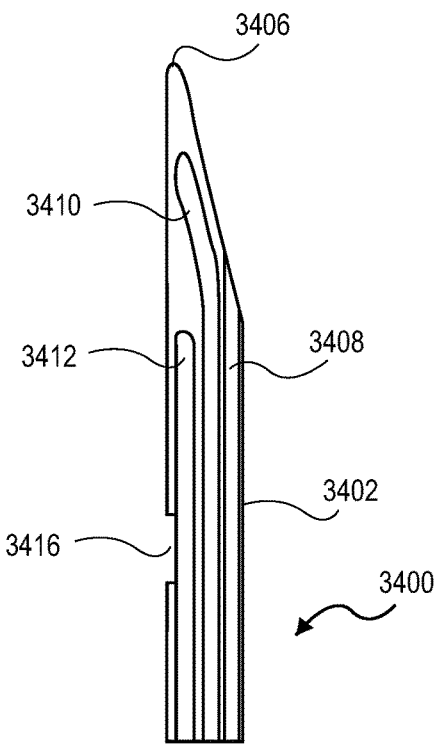
FIGS. 34A-34B illustrate a side cross-section view and a bottom cross-section view of a three lumen conduit configured to accept a balloon, suction, and tools.
Figure 34B:
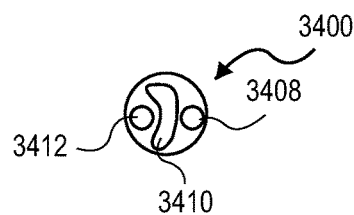

In accordance with some embodiments, as depicted in FIG. 33, the cutting mechanism is comprised of a single hollow or non-hollow tubular member with actuating arms 3062 near the distal end. Outward facing blades 3064 are attached to the actuating arms 3062, as shown in FIG. 33.

In accordance with some embodiments, a device for manipulating tissue at a vessel is described, which has the ability to transition the inlet of a newly created autologous pocket from a narrow hole to a wide mouth. A wide mouth at the top of a tissue pocket insures sufficient blood is able to enter and exit the tissue pocket, which will benefit the pocket's ability to serve as a one-way valve. In the following situations distal refers to further from the operator along the axis of the device.

In many types of embodiments to be described, a conduit with an expandable member is inserted into a tissue pocket between the layers of a vascular lumen and expanded to form an even larger pocket. This conduit and expandable member (often pictured as a balloon) can be utilized to help add tension to the tissue inlet and to help direct a inlet-opening tool to the correct location. In some embodiments, the expandable member, such as a balloon, can be used to enlarge or widen the size of the inlet.

FIGS. 45A-C depict the use of an expandable cutting blade 4500 that is attached to a hollow conduit 4501, which can be slid over the conduit 4504 of the expandable member 4506 that is already in the tissue pocket. In this embodiment, the blade 4500 is inserted over the conduit 4504 in non-expanded form (shown in FIG. 45A here as spiraled around its central axis). Once the expandable cutting blade 4500 is pushed through the tool lumen of the main conduit and out into the lumen of the vessel, it is actuated and the blade 4500 expands such that the blades 4500 stretch out proximal to the inlet (FIG. 45B) into the tissue pocket, and in a curved orientation to closely match that of the lumen wall (FIG. 45C). The upward facing blade 4500 can then be used in conjunction with the expanded expandable member 4506 (shown here as a balloon), to sandwich the intima by moving the two members relative to each other (in a direction that forces them together) so as to cut the mouth of the intima into a larger inlet.

Figure 46:
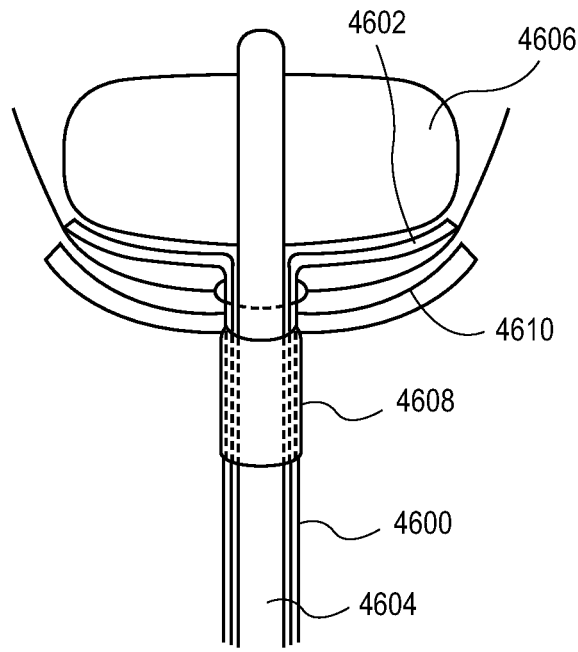
FIG. 46 illustrates a mechanism configured to widen the inlet of an intra-mural pocket with use of a spirally expanding blade and a hard stopper to protect the intra-mural balloon and to provide the necessary counter-traction for tissue cutting.

FIG. 46 depicts a similar embodiment in which a conduit 4600 with an expandable hard stopper 4602 is tubular shaft, which can be slid over the conduit 4604 of the expandable member 4606 that is already in the tissue pocket. The hard stopper 4602 is actuated once it is itself within the inlet of the tissue pocket to support the bottom of the expandable member 4606 (here a balloon). A third parascoping conduit 4608 with an expandable upward facing blade 4610 is then slid over the conduit of the hard stopper. This blade 4610 is actuated as before proximal to the inlet of the tissue pocket. Now the tissue inlet can be cut in the same fashion as the embodiment described in FIGS. 45A-C but with the use of a hard backstop 4602 below the potentially delicate expandable member 4606 within the pocket, so as to help provide a hard surface with, which to facilitate the cut (like a chopping block) and to protect the expandable member 4606.

In another similar embodiment (not pictured) the expandable member itself may have a hard bottom surface, which is revealed upon expansion within the tissue pocket.

Figure 47A:
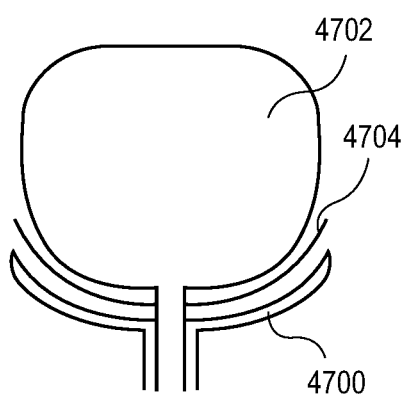
FIGS. 47A-47B illustrate two embodiments of mechanisms configured to widen the inlet of an intra-mural pocket with use of rotationally expanding and hinged blades.

As for the expandable blade described in the past few embodiments, in one type of embodiment (shown in FIG. 47A), the blade 4700 takes a longitudinal curvature to match the bottom of the expandable member 4702 within the pocket (or the hard stopper 4704), so as to cut open the inlet in all places at once.

Figure 47B:
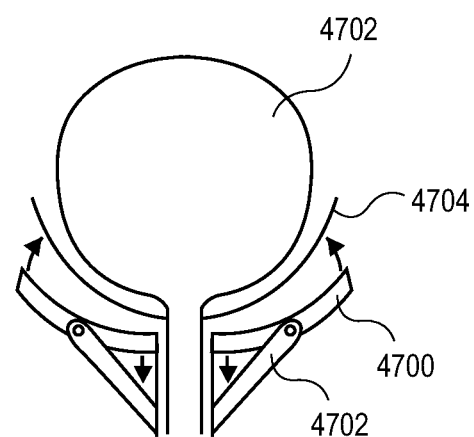

FIG. 47B shows another embodiment of this blade 4700, where the blade 4700 is on a hinge 4702 to allow it to slightly rotate so as to cut the inlet sequentially from a small radial distance from the central axis of the conduit, to a large on. This is much more like the cutting motion of scissors.

Figure 48D:
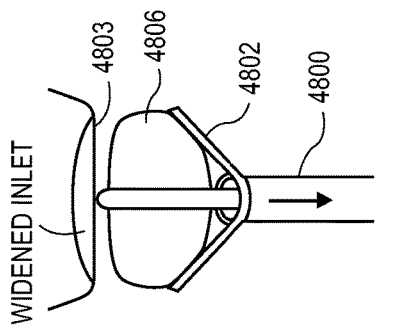
FIGS. 48A-48D illustrate a mechanism configured to widen the inlet of an intra-mural pocket with use of expanding blades, which are fed into an intra-mural space, actuated, and removed from the space to cut the necessary tissue.
Figure 48C:
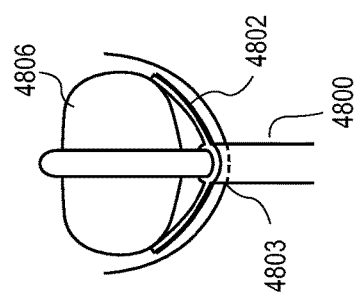
Figures 48A, 48B:
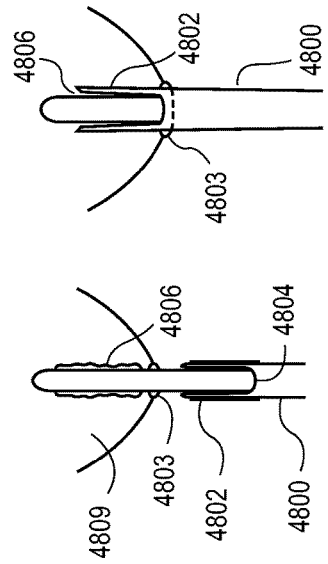

FIGS. 48A-D depict an embodiment in which a conduit 4800 with expanding blades 4802 is slid over the conduit 4804 with expanding member 4806 (FIG. 48A) until the actuatable blades 4802 are slid through the tissue inlet 4803 and into the tissue pocket. In this embodiment, the expandable member 4806 is not expanded at this point. The un-actuated blades 4802 are slid over the non-expanded expandable member 4806 (FIG. 48B). The blades 4802 are actuated by the expansion of the expandable member 4806 (here a balloon) (FIG. 48C), while the blades 4802 are still within the tissue pocket 4809. Both conduits are then pulled proximally together to cut open the tissue inlet into a widened inlet or mouth to the sub-intimal pocket (FIG. 48D). As with all of these embodiments, the tissue inlet does NOT constitute a hole in the lumen wall that extends through all tissue layers.

In a similar embodiment (not pictured), the expansion of the balloon (or expandable member) occurs when the actuatable blades are across the tissue inlet, so that the expansion of the balloon itself provides the cutting force as the blades open up, cutting the inlet.

Figure 49C:
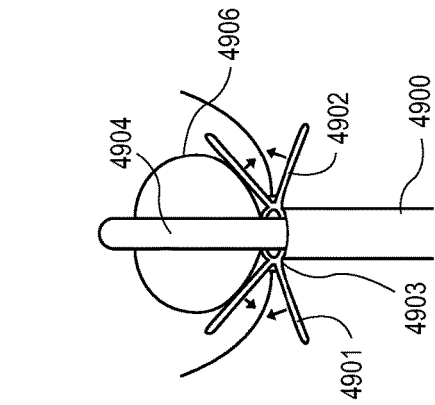
FIGS. 49A-49C illustrate a mechanism configured to widen the inlet of an intra-mural pocket with use of hinged scissor-like blades.
Figure 49B:
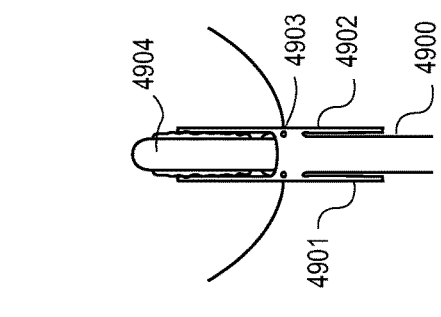
Figure 49A:
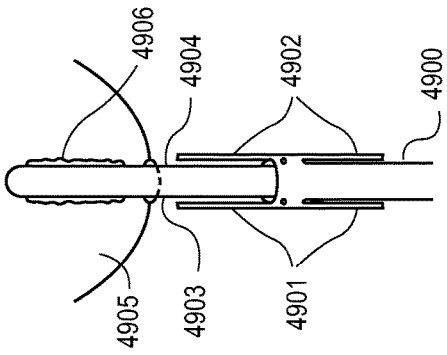

FIGS. 49A-C depict an embodiment in which a conduit 4900 housing a hinged pair of blades 4901, 4902 can be advanced over the conduit 4904 (FIG. 49A) with expandable member 4906 such that the distal blades 4902 extend into the pocket 4905 (through the inlet 4903), but the proximal blades 4901 remain outside the inlet (FIG. 49B). Upon expansion of the expansion member 4906, the blades 4901, 4902 are forced together (a linking mechanism between the blades 4901, 4902 forces the proximal blades 4901 to move upward in conjunction with the downward motion of the distal blades 4902 as provided by the expansion of the expandable member 4906 itself (FIG. 49C). In this way the blades 4901, 4902 slice past each other like scissors to provide a cutting force along the inlet 4903, until a sufficiently large inlet mouth has been created (not pictured).

In one variation on this embodiment, only one of the hinged mechanisms is a cutting blade and the other is simply a hard back stop on a hinge. This could be accomplished with blades on the distal hinged mechanism OR on the proximal hinged mechanism.

In another variation on this embodiment, the hinge can be actuated by an internal mechanism different from the expansion of the expandable member.

In some variations of this embodiment, this scissor like cutting mechanism can be utilized with removal of the inner conduit with expandable member, although the inner conduit may first be utilized to help guide the scissor mechanism to the correct location.

Also not pictured, but the expandable member within the pocket may be inflated during advancement of any cutting mechanism to help align the cutting mechanism longitudinally against, about or past the inlet to the tissue pocket.

In other embodiments not pictured, a perforating mechanism is used to score the tissue along the narrow inlet, so that when an expandable member (such as a balloon) that is within the tissue pocket is forced through the inlet by pulling proximally, the tissue can more easily tear along a preferred path to create a wider mouth to the inlet.

In other embodiments as illustrated in FIGS. 50A-B, a hard balloon 5000 (non-compliant or non-elastic) can be expanded while positioned across the inlet 5002 to create a tear in the narrow inlet 5002, which functions to enlarge or widen the inlet 5002. In one such embodiment, the balloon 5000 has a geometry to help it self-align along this inlet 5002. In some embodiments, the self-aligning geometry can be a relatively narrow or constricted waist portion 5004.

In similar embodiments (not pictured) the self-aligning balloon geometry can be used in conjunction with blades housed on the balloon or advanced over the deflated balloon to assist in the cutting of the intima.

FIGS. 51A-B depict an embodiment in which a hinged cutting mechanism 5100 cuts the mouth open with a top hinge 5102 so that the arms open up like human arms outward. Actuation can be done internally (as pictured) or with assistance from the expandable member.

Figure 52:
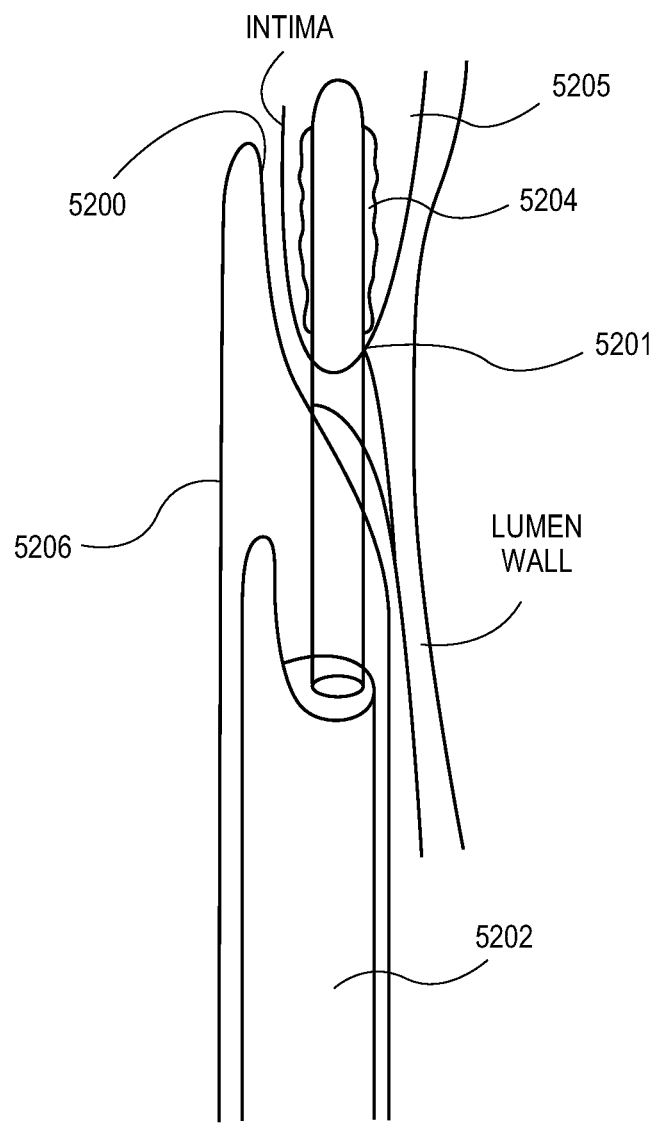
FIG. 52 illustrates a mechanism configured to widen the inlet of an intra-mural pocket with a cutting device that is slid over the main device conduit while the expandable member is within the tissue pocket.

FIG. 52 depicts a type of embodiment in which the cutting mechanism 5200 or a device to assist in cutting the tissue mouth 5201 is slid over the main device conduit 5202 (not through the tool lumen) while the expandable member 5204 (which itself has been passed through the tool lumen) is within the tissue pocket 5205. In this way, the tools can be used in conjunction to help make the cut. Additionally, this outer conduit 5206 can help to assist in the placement of a securement mechanism (potentially a suture or a pin or a clip), through the intimal layer distal to the mouth.

Methods and Mechanisms for Creating Controlled Pocket Geometries within a Vessel Wall (Pouch Formation and/or Inlet Widening)

In accordance with some embodiments, methods and devices for creating a sub-intimal pocket are described. The following embodiments are generally intended to be passed through a tool lumen similar to that pictured in FIGS. 34A and 34B, but may be utilized independent of a conduit such as that or may be utilized in accordance with a different geometry of conduit. In many embodiments, a fluid is ejected from an element for the purpose of mechanically separating tissuel layers. This fluid is referred to as a fluid or sometimes a hydrodissecting fluid. This fluid may be saline, contrast solution, or another fluid.

In many embodiments of methods for using devices described in this description, a puncturing element, such as a hypodermic needle or cannula, is described as being advanced into a lumen wall while ejecting the hydrodissecting fluid. All of the devices described may be used in embodiments of methods in which the puncturing elements are advanced into the lumen wall, at which point the hydrodissecting fluid is then ejected directly into the lumen wall to separate the tissue layers. This method poses the advantage that the fluid being ejected from the puncturing element does not push the vessel wall away from the puncture element as it is advanced (preventing puncture).

In accordance with many such embodiments, a hollow puncturing element is advanced into a luminal wall at some non-parallel relative angle so as to penetrate into the thickness of the wall. In many such embodiments, the puncturing element does so while ejecting a fluid with some significant flow rate sufficient to separate the individual layers of a lumen wall.

FIGS. 39A-C depict one such embodiment in which the hollow puncturing element 3900 houses an expandable member 3902 such as a balloon. Other similar embodiments may use a shape-memory expanding cage in place of a balloon. In these embodiments, the hollow puncturing element 3900 with expandable member 3902 is advanced into a wall while ejecting a hydrodissecting fluid 3904. Once advanced sufficiently into a sub-intimal pocket, the expandable member 3902 can be actuated to further separate tissue layers to an intended geometry and/or to enlarge or expand the size of the inlet to the sub-intimal pocket.

FIGS. 40A-C depict similar embodiments, in which the hollow puncturing element 4000 with expandable member 4002 can be transitioned to a blunt tipped element with expandable member. FIG. 40A depicts one such embodiment in which a stylet 4004 can be advanced out of the distal port 4006 of the hollow puncturing element 4000. As depicted, the distal tip 4008 of the stylet 4004 can be formed from an expandable material that has been confined to a smaller diameter than its natural diameter within the lumen of the puncturing element 4000. This material may be a type of foam, expandable plastic, shape memory metal, or other expandable materials. FIG. 40B depicts a similar embodiment in which the stylet 4004 has a simple cylindrical shape to cancel out the bevel of the puncturing element 4000. In both embodiments just described, the device 4000 would be used to puncture the inner wall of a lumen while ejecting a fluid to separate tissue layers, before the stylet 4004 is inserted into the lumen of the puncturing device 4000. Once safely inside a sub-intimal pocket a small amount, the stylet 4004 can be advanced to transition the device to a blunt tipped element. At this point, the device can be advanced further into the pocket until the entirety of the expandable member 4002 is within the sub-intimal pocket. At this point, the expandable member 4002 can be actuated to form the sub-intimal pocket geometry intended and/or to widen the inlet of the pocket. FIG. 40C depicts an embodiment in which the blunt-tipped stylet 4004 is itself hollow with a through lumen 4010 so that hydrodissection can continue during advancement of the blunt orientation of the device into the sub-intimal pocket.

FIG. 55A depicts an embodiment in which the element that first enters the inner vessel wall 5500 has no sharp tip and is not considered a puncturing element or probe, but a tissue dissection element or probe 5501. In one such embodiment, this element 5501 is hollow and is fluidly connected to a fluid source 5502 and a source of pressure 5503 and is therefore configured to eject a narrow stream of fluid 5504 from a distal nozzle 5505. The tissue dissection element has on it more proximal to the distal nozzle 5505, an expandable member such as a balloon 5506. In this embodiment, the pressure of the ejected fluid can itself be utilized to open a hole 5507 in the inner wall of the vessel 5500, but not through the entire lumen wall 5508 (by using the correct flow-rate and pressure), as shown in FIG. 55B. From here, the element 5501 may be advanced into the wall 5508 to further dissect apart the wall layers with the ejection of fluid 5504, as shown in FIG. 55C. This concept may be utilized in conjunction with any other embodiment listed, such as with the use of separate parascoping expandable members.

FIGS. 41A-E depict another type of embodiment in which a hollow puncturing element 4100 with a gradual taper 4102 is used to enter into a lumen wall while ejecting a hydrodissecting fluid 4104. In some embodiments, an outer hollow sheath 4106, also with a gradual taper 4108 is advanced in tandem with the inner hollow puncturing element 4100 and the tapers can be approximately matched. Once a sub-intimal pocket is initiated due to the hydrodissection, both elements 4100, 4106 are advanced through the vessel wall inlet 4105 into the space. The tapered nature of the elements 4100, 4106 helps to open up the inlet to the subintimal pocket during advancement. Once both elements 4100, 4106 are advanced to a point where the inlet to the sub-intimal pocket is proximal to the distal end 4110 of the outer hollow tapered sheath (FIG. 41A), the inner hollow puncturing element 4100 is removed (FIG. 41B), the outer blunt sheath 4106 can be advanced further into the pocket to insure placement in the pocket. At this point a conduit 4112 with an expandable member 4114 (depicted here as a balloon) can be advanced within the lumen 4107 of the outer sheath 4106 until the distal tip 4116 of the conduit with expandable member 4114 is near the distal tip 4110 of the outer sheath 4106 (FIG. 41C). At this point, the outer sheath 4106 can be retracted out of the sub-intimal pocket, leaving the conduit 4112 and expandable member 4114 within the sub-intimal pocket (FIG. 41D). Now that the expandable member 4114 is fully within the confines of the sub-intimal pocket, FIG. 41E depicts how it can be actuated or expanded to further separate tissue layers to create the desired geometry and/or enlarge or widen the inlet 4105 to the sub-intimal pocket (not depicted).

In a similar embodiment to that previously described, not pictured, the puncturing element is not tapered, but has a nearly constant diameter, which matches more or less the inner diameter of the outer hollow sheath which is tapered. In the same way, the inner puncturing element can be removed for insertion of an element with an expandable member.

FIG. 42 depicts a similar embodiment that has an inner puncturing element 4200 that has a nearly constant diameter, and an outer sheath 4202 that is tapered gradually and houses an expandable member 4204 (displayed here as a balloon). The inner puncturing element 4200 can be advanced while ejecting a hydrodissecting fluid 4206 until it punctures the inner lumen wall and creates a sub-intimal pocket. At this point, the outer tapered sheath 4202 can be passed through the opening created by the puncture element 4200 until the expansion mechanism 4204 is within the sub-intimal pocket. At this point the expansion element 4204 can be actuated to further separate the tissue layers and/or enlarge or widen the inlet (not pictured).

FIGS. 43A-C depict an embodiment in which the inner puncturing element 4300 is tapered 4302 and has a sharp distal tip 4304. This embodiment also has an outer sheath 4306 with relatively constant wall thickness, which has a distal tip 4308 that constricts to a narrower inner and outer diameter due to the shape memory of the material. This distal tip 4308 is elastic in that it can be easily stretched out to the inner and outer diameter of the more proximal shaft of the sheath 4306 if it is slid over a larger inner member 4300 (as shown in FIG. 43A). In this embodiment, as with many others, the inner puncturing element 4300 can be advanced while ejecting a hydrodissecting fluid 4310 into the lumen wall to create a sub-intimal pocket. At this point, the outer sheath 4306 can be advanced distally along the inner tapered puncture element 4300 shaft so that the distal tip 4308 of the outer sheath 4306 is allowed to constrict more and more. Once the distal tip 4308 of the outer sheath 4306 is passed through the inlet into the sub-intimal space it is advanced further until it is securely within the sub-intimal pocket (FIG. 43B). At this point the inner puncturing element 4300 can be removed and a conduit 4312 with an expandable member 4314 can be inserted into the sheath 4306 (FIG. 43C). At this point the outer sheath 4306 can be removed and the expandable member 4314 can be actuated (not pictured).

In other similar embodiments not pictured, this same type of outer sheath can itself contain an expandable member, so that once securely in the sub-intimal pocket, the expandable member can be actuated to create a larger pocket and/or enlarge or widen the inlet.

In other similar embodiments not pictured, this same type of outer sheath can be utilized with a non-tapered inner puncture element.

FIGS. 44A-C depict the utilization of a hollow puncturing element 4400 with a stopper mechanism 4402. FIG. 44A depicts how this stopping mechanism is achieved. The distal tip 4404 of the puncturing element 4400 has a sharp side 4406 (a half bevel), which transitions across a saddle geometry 4407 into a more blunt opposing side 4408. The blunt side 4408 of the element 4400 extends to its blunt distal tip 4410 at a longitudinal distance that is proximal to the sharp distal tip 4412 of the sharp side 4406. In some embodiments (as depicted) this hollow puncturing element 4000 is utilized by being advanced into a lumen wall while ejecting a hydrodissecting fluid 4414 (FIG. 44A). Once a pocket is formed, a conduit 4416 with expandable member 4418 (such as a balloon as depicted) and a blunt, off-center biased tapered tip 4420, is advanced through the hollow puncturing element 4400 such that the narrow part of the blunt tapered tip 4420 matches with the sharp side 4406 of the puncturing element 4400 in terms of radial orientation (FIG. 44B). This allows the inner conduit 4416 to find the inlet created in the lumen wall and dialate it open upon advancement of the tapered tip 4420. Once advanced into the sub-intimal pocket, the expandable member 4418 can be actuated (FIG. 44C). In other embodiments, not pictured, the blunt distal tip 4420 extends to a longitudinal distance approximately equal to that of the sharp distal tip 4412. In other embodiments, not pictured, the blunt distal tip 4420 extends to a longitudinal distance more distal than that of the sharp distal tip 4412.

In a very similar embodiment (not pictured), the inner conduit with expandable member and blunt distal tip, is itself hollow and therefore ejection of the hydrodissecting fluid can be initiated through that lumen so that the inner conduit can be pre-loaded into the hollow puncturing element such that the blunt distal tip of the inner conduit is just proximal to the sharp distal tip of the puncturing element.
Methods and Mechanisms for Creating Controlled Pocket Geometries within a Vessel Wall (Valve Flap Expansion)

After a monocuspid valve flap is created within a vessel, it may be advantageous to further propagate the dissection between the valve flap and the vessel wall, to expand the angle subtended by the valve flap past 180 degrees, thereby enabling the valve flap to fully occlude the vessel when it is closed.

Figure 28A:
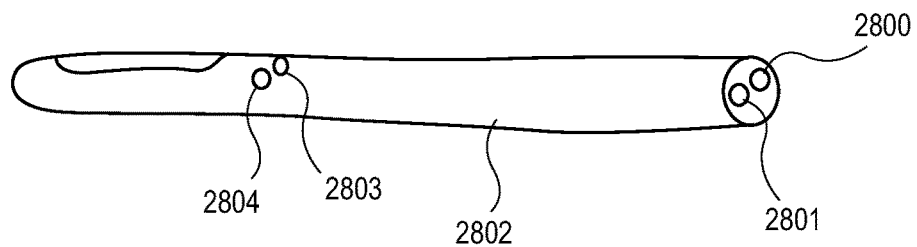
FIGS. 28A-28F illustrate a method for expanding a dissection flap to more than 180 degrees by utilizing a conduit assembly comprised of two expanding elements and a tensioning element.

FIG. 28A depicts an embodiment of a valve flap expansion device and method. The embodiment includes two tool lumens 2800/2801, which extend through the main tubular shaft 2802. Both tool lumens 2800/2801 terminate in exit ports 2803/2804 near the distal end of the main tubular shaft 2802, separated by a radial offset. Two expandable dissection elements 2805/2806 are advanced, one through each exit port 2803/2804, into the intramural pocket 2807 until the full depth of the pocket is reached (as shown in FIGS. 28B-28C).

Figure 28B:
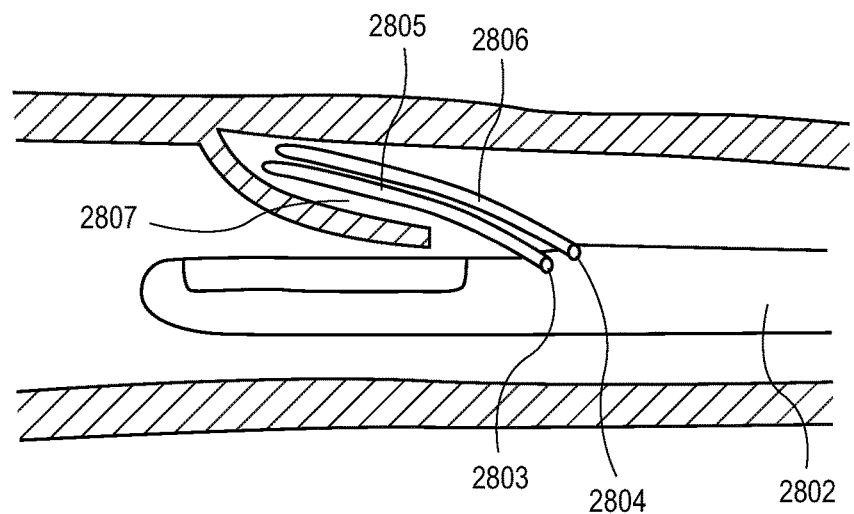
Figure 28C:
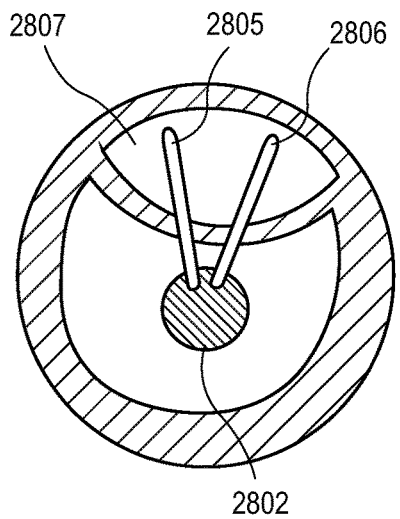

In some embodiments, the expandable dissection elements 2805/2806 are non-compliant balloons, such as non-compliant balloons that upon inflation have a cross-section wherein the length of the major axis is substantially greater than the length of the minor axis (as shown in FIGS. 28B-28C). In embodiments in which the expandable dissection elements are balloons, each balloon is connected to an inflation lumen (not depicted).

In some embodiments, the expandable dissection elements 2805/2806 are metal cages made from a shape memory metal such as Nitinol.

In the main lumen of the vessel, the expansion window 2808 is rotated to line up between the two expandable dissection elements 2805/2806. The expandable tensioning element 2809 is activated, travels outwards through the expansion window, and forces the vessel wall to comply and elongate along the axis of expansion. This action will press the flap 2810 against the vessel wall 2811 between the two expandable dissection elements 2805/2806, temporarily dividing the intramural pocket into two sections 2812/2813, with each section containing an expandable dissection element 2805/2806 (as shown in FIGS. 28D-28E).

The two expandable dissecting elements 2805/2806 the intramural pocket are activated. During activation of the expandable dissecting elements 2805/2806, the expandable tensioning element 2809 continues to press the center of the flap 2010 against the vessel wall 2011, maintaining an acute angle between corners of the flap and site of attachment to the vessel wall. FIG. 28F depicts further activation of the expandable dissecting elements 2805/2806 propagates the dissection between the valve flap and the vessel wall, until the angle subtended by the flap is sufficiently large for occlusion of the vessel.

Figure 28D:
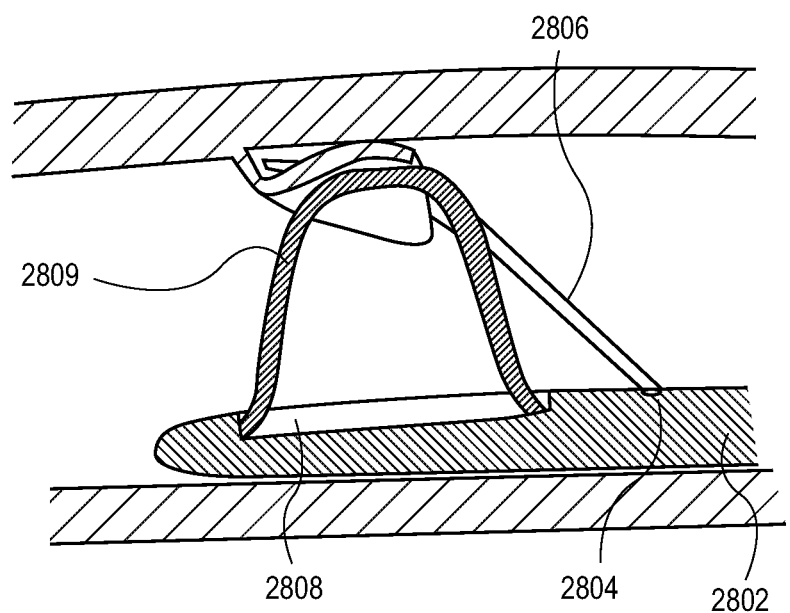
Figure 28E:
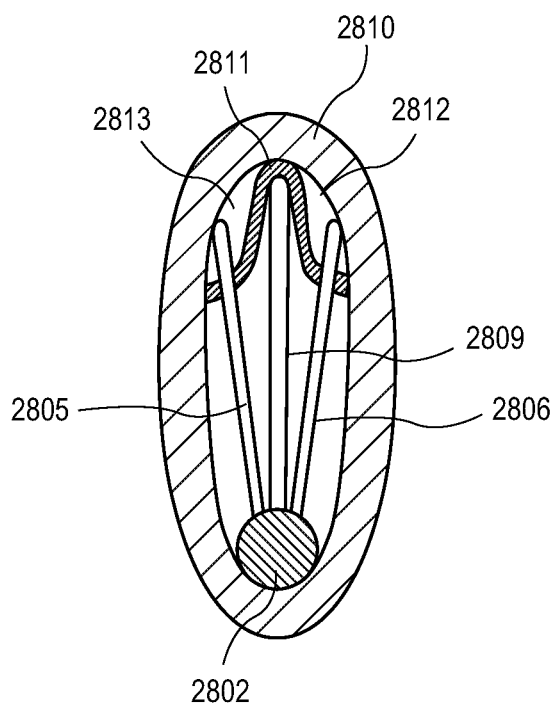
Figure 28F:
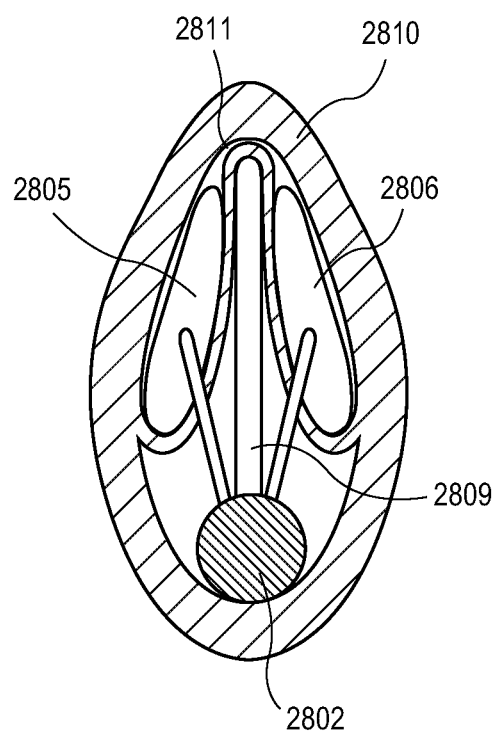

In some embodiments, the expandable tensioning element 2809 is a metal cage made from a shape memory metal such as Nitinol (as shown in FIGS. 28D-28E).

In some embodiments, the expandable tensioning element 2809 is a non-compliant balloon.

In some embodiments, both expandable dissection elements 2805/2806 of the valve flap creation mechanism utilize a single shared tool lumen 2800 and exit port 2803.
Methods and Mechanisms for Creating Controlled Pocket Geometries within a Vessel Wall (Valve Flap Securement)

Figure 56B:
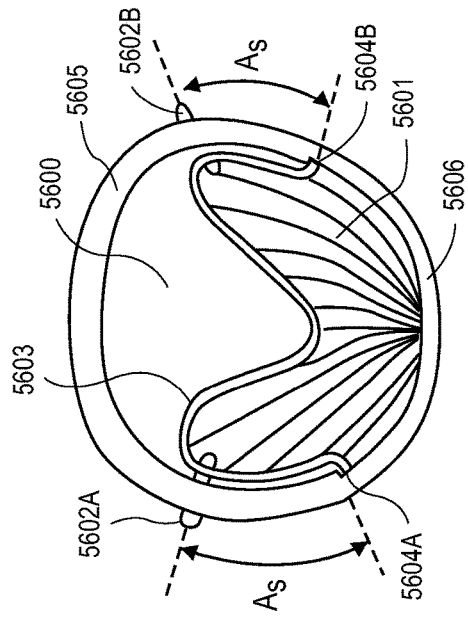
FIGS. 56A-56B illustrate top views of autologous monocuspid valves in the open configuration (blood flowing up), configured with alternate embodiments of securement.
Figure 56D:
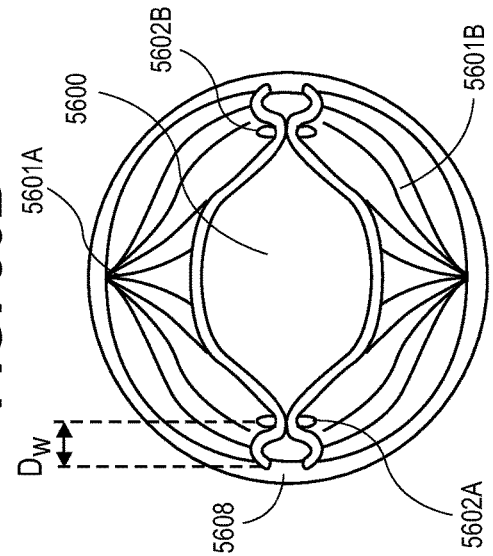
FIGS. 56C-56D illustrate top views of autologous bicuspid valves in the open configuration (blood flowing up), configured with alternate embodiments of securement.
Figure 56A:
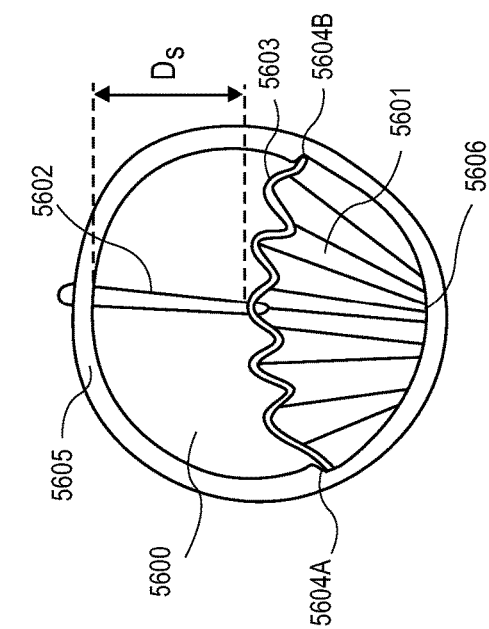
Figure 56C:
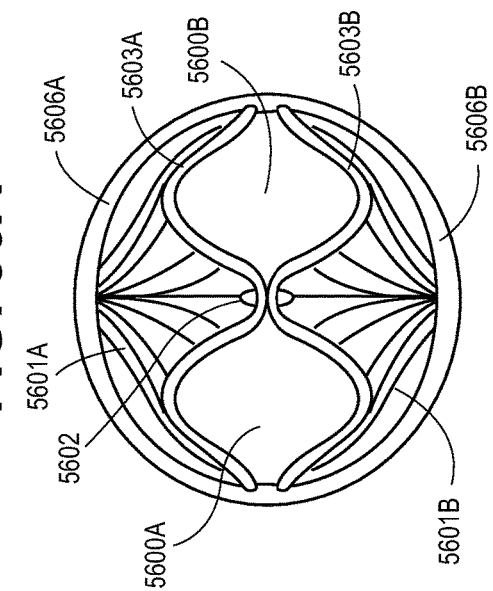

After a valve pocket has been created it is necessary to secure the valve flap in place to prevent it from re-adhering to the wall and to control other hemodynamic properties associated with flow through the valve and the mechanics of the valve itself. FIGS. 56A and 56B depict stitching methods for monocuspid valves (greater than 180°), depicted in the open position, from a top down view, where the non-shaded region represents the true lumen 5600, and the shaded region represents the valve pockets 5601. FIG. 56A depicts a method embodiment in which a stitch 5602 or other securement mechanism (such as a clip or a T tag) is placed at the center portion of the valve flap 5603 (equidistant from both edges 5604a,b of the dissected flap 5603), and is connected on the other end to the fully thickness of the opposing vessel wall 5605. The stitch 5602 is maintained in a loose configuration (a long length before becoming taut), which allows blood to flow upward (out of the page) through the true lumen 5600, forcing the valve flap 5603 to open as much as is permitted by the stitch 5602. The stitch length ($D_s$) should be chosen to ensure the flap 5603 cannot re-adhere to the other vessel wall 5606 from which it first came. In some embodiments, the $D_s$ should be between 20% and 95% of the vessel diameter. In some embodiments, the $D_s$ should be between 50% and 90% of the vessel diameter. In some embodiments, the $D_s$ should be between 70% and 80% of the vessel diameter. FIG. 56B depicts a different stitching method, which includes placing two stitches 5602a, 5602b, substantially symmetrically about the central axis of the vessel. In this embodiment, both stitches are placed a specific angle ($A_s$) from the edge of the tissue dissection flap 5604a,b. In some embodiments, $A_s$ is chosen to be between 5° and 80°. In some embodiments, $A_s$ is chosen to be between 10° and 45°. In some embodiments, $A_s$ is chosen to be between 15° and 30°. FIGS. 56C and 56D depict stitching methods for bicuspid autologous or natural valves. Valves are depicted in the open position, from a top down view, as blood is pumping upward (out of the page) through the true lumen 5600, to then later close the valves by flowing downward (into the page) into the valve pockets 5601. FIG. 56C depicts an embodiment in which a single tight stitch 5602 is placed along the center-line of the vessel lumen, bisecting each valve cusp 5603a,b. This allows fluid to flow through two separate true lumen orifices 5600a,b during the valve open phase. FIG. 56D depicts an embodiment in which two tight stitches 5602a,b are placed symmetrically about the center-line of the vessel to permit only one major true lumen orifice 5600 for blood to flow through during the valve open phase. The stitches 5602a,b are placed a certain distance from the vessel wall 5608 ($D_w$). In some embodiments, $D_w$ is chosen to be between 1% and 40% of the vessel diameter. In some embodiments, $D_w$ is chosen to be between 5% and 25% of the vessel diameter. In some embodiments, $D_w$ is chosen to be between 10% and 20% of the vessel diameter.
Methods and Mechanisms for Creating Controlled Pocket Geometries within a Vessel Wall (Full Integrated Embodiments)

Figure 29D:
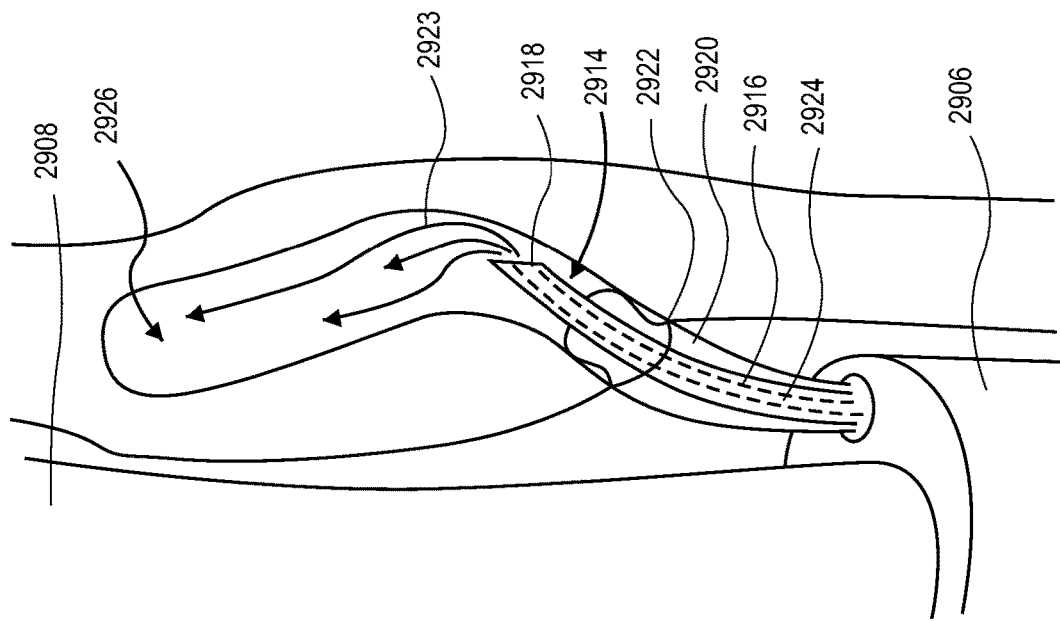
Figure 29C:
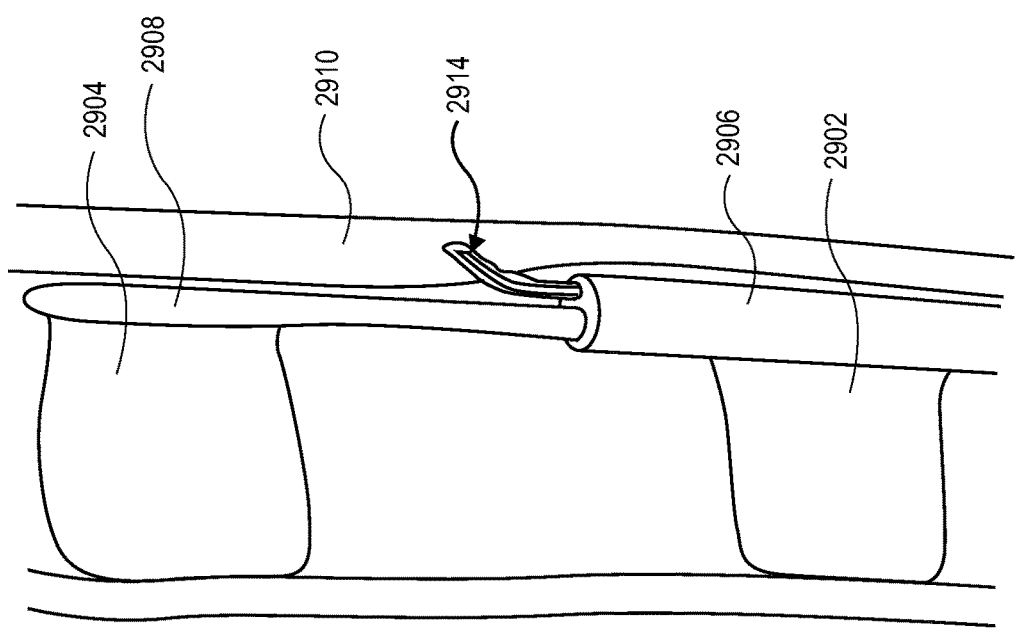
Figure 29F:
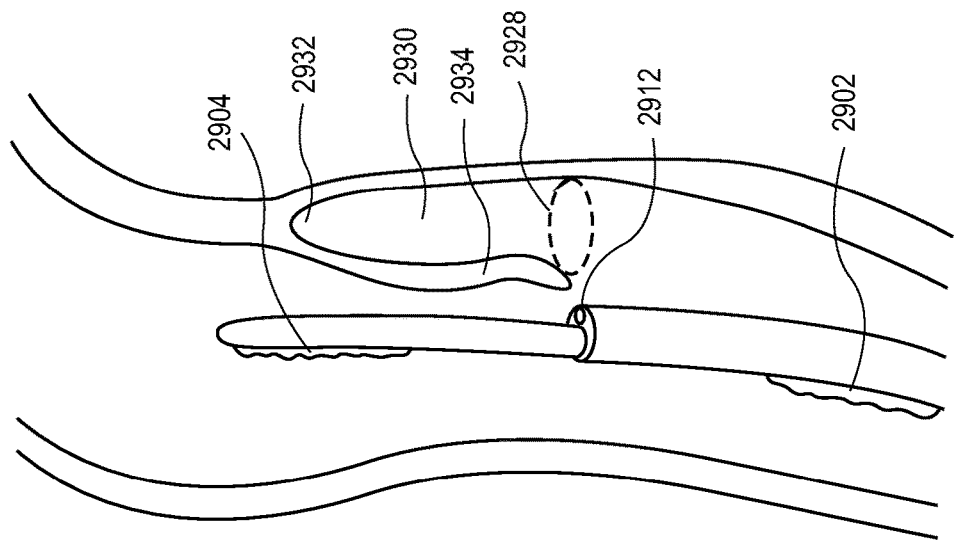
Figure 29E:
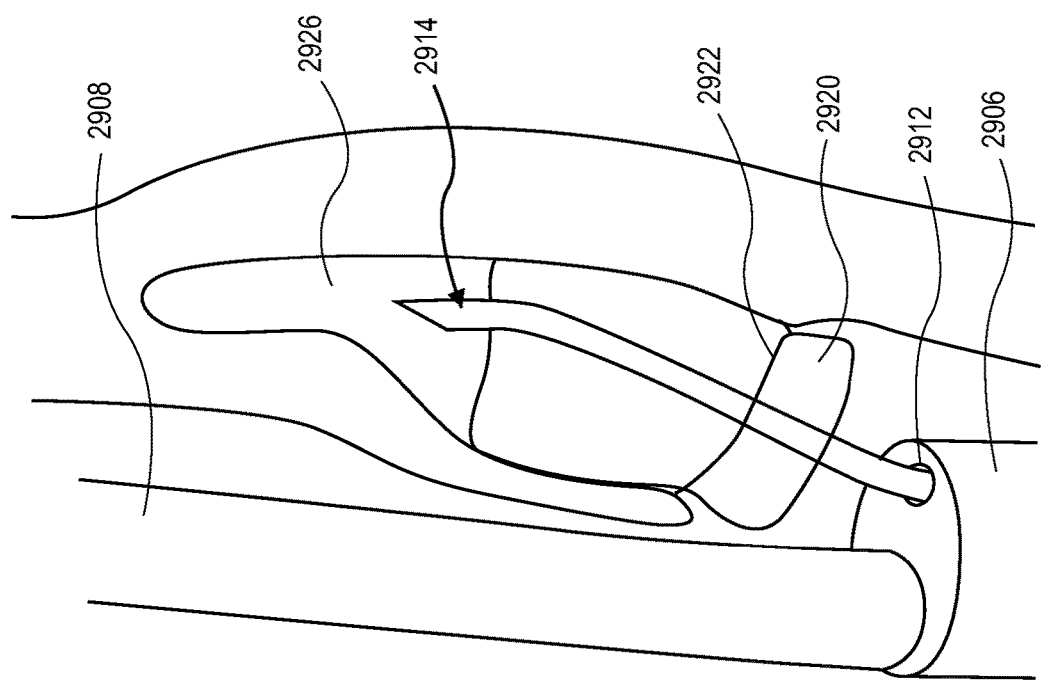

FIGS. 29A-29F depicts one embodiment of a fully integrated valve creation device. The depiction is meant to give one concrete example of how the many different components can be used in combination. This by no means is a complete description of all potential embodiments of the device and method, as the many different embodiments described in this description can be used in any combination. FIG. 29A depicts a parascoping device 2900 which includes a proximal balloon 2902 and a distal balloon 2904, both of which expand off the back of the proximal shaft 2906 and distal shaft 2908, respectively when inflated (FIG. 29B). The distal shaft 2908 is shown after it has been advanced distally with respect to the proximal shaft 2906, which creates a tautness in the vessel wall 2910. A side port 2912 is now positioned at a known distance from the vessel wall 2910, and at a known angle with respect to the vessel wall (depicted here as 90 degrees). FIG. 29C depicts a puncture element 2914, which has been advanced at a specific angle (in this depiction a puncture element with distal bend 2916 and distal bevel 2918 is used) into but not all the way through the vessel wall 2910. FIG. 29D depicts a close view of the puncture element, which comprises a valve creation balloon 2920 on its shaft, terminating a short distance (about 0 mm to 2 mm) from the distal bevel 2918. In this depiction, a seal technique is used, in which the balloon 2920 is inflated slightly just upon entry into the vessel wall 2910, to create a seal around the ostium 2922 of the vessel wall defect (at the puncture location). A hydrodissecting agent 2923 such as saline or contrast is injected through a lumen 2924 within the puncture element 2914. This creates a separation of tissue layers, or a pouch 2926 within the vessel wall 2910. FIG. 29E depicts how the puncture element 2914 has been rotated 180-degrees and advanced further into the newly created tissue layer pouch 2926. At this point, the valve creation balloon 2920 is inflated to open up the ostium 2922 within the vessel wall, which will serve as the top-most mouth of the valve sinus. FIG. 29F depicts the fully formed valve with valve sinus 2930, valve opening 2928, valve cusp 2932, and valve leaflet 2934 in 2 dimensions, after the valve creation balloon 2920 has been retracted, and the sideways-facing expansion balloons 2902, 2904 have been deflated. The created valve can then be adhered to the opposing walls in a way to prevent re-adherence of that flap to its original native location (not depicted). In some embodiments this is accomplished with a single stitch or clip with loose securement in a central location (sufficiently equally spaced from both edges of the valve mouth). In some embodiments, this is accomplished with two stitches or clips with tight securement, both located some distance close to (between 1 and 6 mm) from the edges of the valve mouth.

Figure 57B:
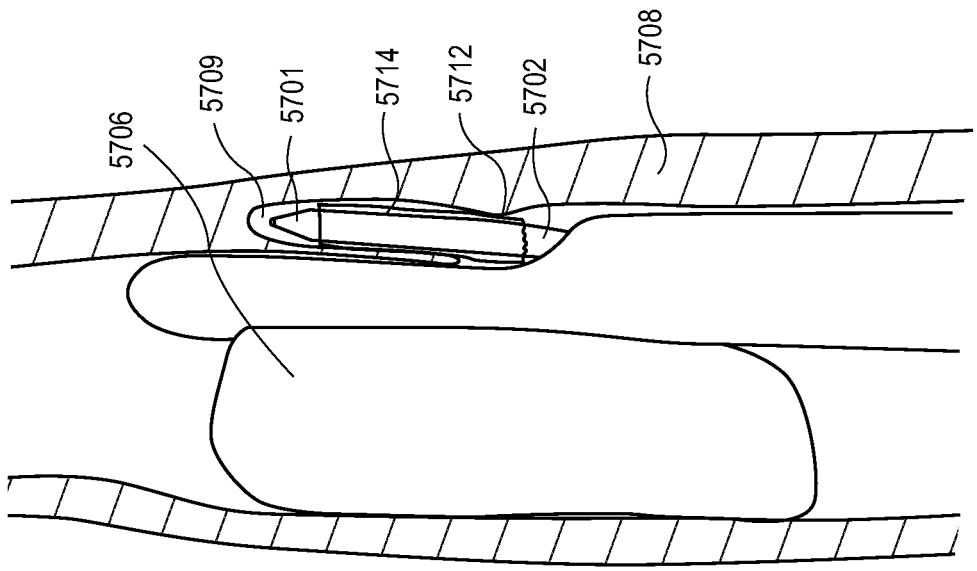
Figure 57A:
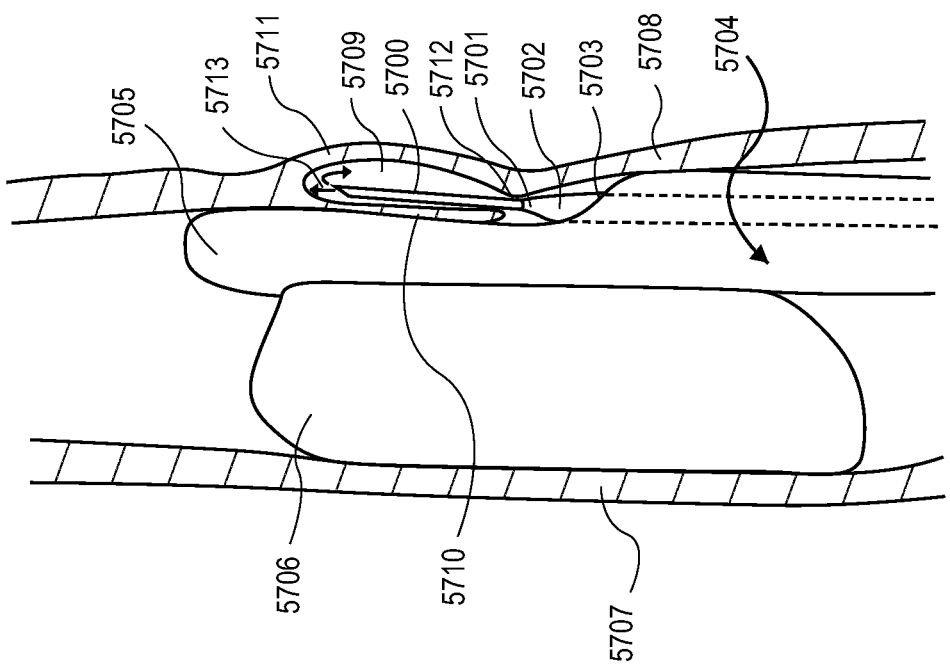

FIGS. 57A-D depict an embodiment, which includes all aspects of a valve creation procedure utilizing aspects of previously described sub-embodiments. This is by no means all-inclusive, but serves to give an example of one way in which these mechanisms and methods can be used together. In the embodiment, depicted in FIG. 57A, the puncture element 5700 extends from the distal end 5701 of a tissue dissection probe 5702 (as depicted internally in FIG. 7). The puncture element 5700 and probe 5702 can both extend from a side port 5703 of a support device 5704, which is near the distal end of the support device 5705. The support device includes in this embodiment a single expansion mechanism 5706 to create the necessary wall straightness, tautness, and apposition along and near the side port 5703 of the support structure 5704. The expansion mechanism 5706 is shown directly opposite this side port 5703 in the longitudinal axis. The geometry of the support structure is such that, upon expansion of an expansion mechanism 5706 (here a balloon) into one side of the vessel wall 5707, the vessel wall on the opposite side 5708 is forced to take an offset around the support structure 5704, which allows the puncture element 5700 and probe 5702 to approach the wall 5708 at an angle to permit entry, and allows the puncture element 5700 and probe 5702 to enter the vessel wall 5708 sufficiently parallel to it and within a plane 5709 somewhere between the inner most layer 5710 and the outer most layer 5711. The stiffness of the support mechanism is such that, upon expansion of the balloon 5706, the distal portion of the support structure 5705 does not bend significantly along any axis. FIG. 57A depicts the system after wall apposition has been accomplished, and the puncture element 5700 has been advanced distally through the distal end 5701 of the stationary probe 5702 (which helps to hold the correct orientation of the puncture element 5700), until it punctures the vessel wall 5708. Upon entry into the wall 5708, the puncture element 5700 itself holds a seal around the inlet 5712 into the wall sufficiently to create a hydrodissection, and is advanced within the planes of the vessel wall along a distance sufficient to create a valve, while injecting a hydrodissection agent 5713 with sufficient flow. FIG. 57B depicts the probe 5702 with a tapered distal end 5701 as it is advanced over the needle 5700 and into the inter-mural plane 5709 that has been created. The probe 5702 is comprised of a balloon 5714 just proximal to the tapered distal end 5701, extending long enough so that it can be fully advanced within the pocket, but still extends proximally somewhat outside the inlet 5712 to the pocket. In an alternate embodiment, the wall apposition balloon 5706 may be deflated prior to advancement of the probe into the wall 5708. FIG. 57C depicts removal of the support mechanism, leaving the balloon 5714 and supporting probe 5702 within the vessel wall 5708. FIG. 57D depicts inflation of the intra-mural balloon 5714 to open the inlet 5712 in the wall significantly to form a valve mouth. The expansion of the balloon has created a competent valve flap 5715. A mechanism for placement of appropriate securement would then follow (not depicted).

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the claims appended hereto. Any feature described in any one embodiment described herein can be combined with any other feature of any of the other embodiment whether preferred or not.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A method of controlled dissection of a blood vessel wall, the method comprising:
    positioning a tubular assembly at a treatment site within a blood vessel lumen, the tubular assembly having a longitudinal axis, wherein a distal portion of the tubular assembly includes a supporting surface substantially parallel to the longitudinal axis, a transition surface proximal the supporting surface, an exit port positioned along the transition surface, and an expandable member coupled to the distal portion of the tubular assembly along a length that coincides with at least a portion of the supporting surface and at least a portion of the transition surface, and wherein the coinciding portions of the tubular assembly are sufficiently stiff such that they resist bending when the expandable member is in an expanded state;

conforming a portion of the blood vessel wall at the treatment site to the supporting surface and the transition surface such that (i) a first length of the conformed portion of the blood vessel wall is in apposition with the supporting surface, and (ii) a second length of the portion of the blood vessel wall is in apposition with a region of the transition surface, wherein conforming the portion of the blood vessel wall includes expanding the expandable member against the blood vessel wall;

while the first and second lengths of the blood vessel wall are in apposition with the supporting surface and the transition surface, respectively:

advancing a puncture element distally through the exit port in a direction that is substantially parallel to a longitudinal axis of the blood vessel wall along the first length, and penetrating an inner surface of the blood vessel wall along the conformed portion of the blood vessel wall (i) in a direction that is substantially parallel to a longitudinal axis of the blood vessel wall along the first length, and (ii) at a penetration depth measured along the thickness of the blood vessel wall; and after penetrating the blood vessel wall, advancing the puncture element within the blood vessel wall substantially parallel to a longitudinal axis of the first length while substantially maintaining the puncture element at the penetration depth along the full length of the puncture element travelling within the blood vessel wall, thereby separating a first layer of tissue from a second layer of tissue to create an intramural space within the blood vessel wall between the first layer and the second layer.

2. The method of claim 1, further comprising ejecting fluid into the intramural space via the puncture element, thereby enlarging the space.

3. The method of claim 1, further comprising ejecting fluid into the intramural space via the puncture element while advancing the puncture element within the blood vessel wall, thereby enlarging the space.

4. The method of claim 1 wherein the portion of the blood vessel wall is a first portion and wherein the expandable member is expanded against a second portion of the blood vessel wall circumferentially opposite the first portion of the blood vessel wall.

5. The method of claim 1, further comprising holding the first length of the blood vessel wall in tension across the width of the supporting surface.

6. The method of claim 1, wherein the expandable member is a first expandable member and the method further comprises:

advancing a second expandable member through the exit port and positioning the second expandable member within the intramural space; and expanding the second expandable member within the intramural space to enlarge the intramural space, thereby creating an intramural pocket.

7. The method of claim 1 wherein penetrating the inner surface of the blood vessel wall creates an opening at the inner surface of the blood vessel wall, and wherein the method further comprises widening the opening in a circumferential direction.

8. The method of claim 1 wherein the puncture element enters the blood vessel wall substantially parallel to the supporting surface.

9. The method of claim 1 wherein advancing the puncture element further includes separating the first tissue layer from the second tissue layer along a length of the blood vessel wall, wherein the length is at least as great as the diameter of the blood vessel at the treatment site.

10. A method for gaining controlled entry into a blood vessel wall, the method comprising:

positioning a tubular assembly at a treatment site within a blood vessel lumen, wherein a distal region of the tubular assembly includes a transition surface, an opening along the transition surface, a supporting surface extending distally from the transition surface, and an expandable member coupled to the distal region of the tubular assembly along a length that coincides with at least a portion of the supporting surface and at least a portion of the transition surface, and wherein the coinciding portions of the tubular assembly are sufficiently stiff such that they resist bending when the expandable member is in an expanded state;

conforming the blood vessel wall at the treatment site to a portion of the distal region, wherein conforming the blood vessel wall (i) places a first length of the blood vessel wall in apposition with the supporting surface, and (ii) urges a second length of the blood vessel wall towards the transition surface, wherein conforming the blood vessel wall includes expanding the expandable member; and holding the first length in tension across a width of the supporting surface; and while holding the first length in tension, inserting a puncture element into the blood vessel wall at a location along the conformed portion of the blood vessel wall, wherein the puncture element extends distally through the opening substantially parallel to a longitudinal axis of the blood vessel wall, and wherein the puncture element is inserted at a predetermined depth along a thickness of the blood vessel wall and in a direction that is substantially parallel to a longitudinal axis of the first length of the blood vessel wall.

11. The method of claim 10 wherein the expandable element is disposed circumferentially opposite the supporting surface at the distal portion.

12. The method of claim 10, further comprising advancing the puncture element distally within the first length of the blood vessel wall along a longitudinal axis of the first length.

13. The method of claim 10, further comprising advancing the puncture element within the blood vessel wall substantially parallel to a longitudinal axis of the first length of the blood vessel wall while maintaining the puncture element at the predetermined depth along the full length of the puncture element travelling within the blood vessel wall.

14. The method of claim 13, further comprising ejecting a fluid from the puncture element into an interior portion of the blood vessel wall while advancing the puncture element.

15. The method of claim 10 wherein inserting the puncture element creates an opening at an inner surface of the blood vessel wall at a location along the conformed portion of the blood vessel wall, and wherein the method further comprises widening the opening in a circumferential direction to about 180 degrees or less around the circumference of the blood vessel.

16. The method of claim 10 wherein inserting the puncture element creates an opening at an inner surface of the blood vessel wall at a location along the conformed portion of the blood vessel wall, and wherein the method further comprises widening the opening by positioning a cutting element through the opening into an interior portion of the blood vessel wall and expanding the cutting element.

17. The method of claim 10 wherein inserting the puncture element creates an opening at an inner surface of the blood vessel wall at a location along the conformed portion of the blood vessel wall, and wherein the method further comprises widening the opening by positioning a cutting element through the opening into an interior portion of the blood vessel wall, expanding the cutting element, and pulling the cutting element proximally.

18. The method of claim 10 wherein advancing the puncture element separates a first layer of the blood vessel wall from a second layer of the blood vessel wall, thereby creating a space within the vessel wall, wherein a length of the space is at least as great as the diameter of the blood vessel at the treatment site.

19. A method of controlled dissection of a blood vessel wall, the method comprising:
    positioning a tubular assembly at a treatment site within a blood vessel lumen, the tubular assembly having a longitudinal axis, wherein a distal portion of the tubular assembly includes a supporting surface substantially parallel to the longitudinal axis, a transition surface proximal the supporting surface, an exit port positioned along the transition surface, and an expandable member coupled to the distal portion of the tubular assembly along a length that coincides with at least a portion of the supporting surface and at least a portion of the transition surface, and wherein the coinciding portions of the tubular assembly are sufficiently stiff such that they resist bending when the expandable member is in an expanded state;
    conforming a portion of the blood vessel wall at the treatment site to the supporting surface and the transition surface such that (i) a first length of the conformed portion of the blood vessel wall is in apposition with the supporting surface, and (ii) a second length of the conformed portion of the blood vessel wall is in apposition with the transition surface; and
    while the first and second lengths of the blood vessel wall are in apposition with the supporting surface and the transition surface, respectively, advancing a puncture element distally through the exit port in a direction that is substantially parallel to a longitudinal axis of the blood vessel wall along the first length, wherein the puncture element is advanced distally such that a distal-most edge of the puncture element remains within a plane that is spaced apart from the supporting surface by a distance that is of from about 0.005 inches to about 0.105 inches.

* * * * *

UNITED STATES PATENT AND TRADEMARK OFFICE
CERTIFICATE OF CORRECTION

| | | |
|---|---|---|
| PATENT NO. | : 9,827,005 B2 | Page 1 of 1 |
| APPLICATION NO. | : 15/235127 | |
| DATED | : November 28, 2017 | |
| INVENTOR(S) | : Wilson et al. | |

It is certified that error appears in the above-identified patent and that said Letters Patent is hereby corrected as shown below:

In the Specification

On Column 1, Line 20, before the "TECHNICAL FIELD," please insert the following paragraph:
--STATEMENT REGARDING FEDERALLY SPONSORED RESEARCH AND DEVELOPMENT
This invention was made with Government support under Contract RR025742 awarded by the National Institutes of Health. The Government has certain rights in the invention.--

Signed and Sealed this
Second Day of December, 2025

John A. Squires
*Director of the United States Patent and Trademark Office*